(12) United States Patent
Rodriguez

(10) Patent No.: US 6,919,291 B2
(45) Date of Patent: Jul. 19, 2005

(54) FLUORINATED ZWITTERIONIC COCATALYST ACTIVATORS FOR OLEFIN POLYMERIZATION

(75) Inventor: George Rodriguez, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 209 days.

(21) Appl. No.: 10/415,158

(22) PCT Filed: Oct. 31, 2001

(86) PCT No.: PCT/US01/46187

§ 371 (c)(1),
(2), (4) Date: Apr. 24, 2003

(87) PCT Pub. No.: WO02/36639

PCT Pub. Date: May 10, 2002

(65) Prior Publication Data

US 2004/0110631 A1 Jun. 10, 2004

Related U.S. Application Data

(60) Provisional application No. 60/246,302, filed on Nov. 6, 2000, and provisional application No. 60/274,788, filed on Mar. 9, 2001.

(51) Int. Cl.[7] .......................... B01J 31/00; B01J 37/00; C08F 4/44; C08F 5/06; C08F 9/02
(52) U.S. Cl. ...................... 502/103; 502/117; 502/155; 502/167; 526/134; 526/163; 556/170; 556/174; 568/9; 568/16
(58) Field of Search .................. 502/103, 117, 502/155, 167; 526/134, 163; 556/170, 174; 568/1, 16

(56) References Cited

U.S. PATENT DOCUMENTS

| | | | |
|---|---|---|---|
| 5,198,401 A | 3/1993 | Turner et al. | 502/155 |
| 5,278,119 A | 1/1994 | Turner et al. | 502/155 |
| 5,296,433 A | 3/1994 | Siedle et al. | 502/117 |
| 5,447,895 A | 9/1995 | Marks et al. | 502/117 |
| 5,502,017 A | 3/1996 | Marks et al. | 502/103 |
| 6,124,231 A | 9/2000 | Fritze et al. | 502/152 |
| 6,255,531 B1 | 7/2001 | Fritz et al. | 568/3 |
| 6,329,313 B1 | 12/2001 | Fritze et al. | 502/202 |
| 6,344,529 B1 | 2/2002 | Carnahan et al. | 526/134 |

FOREIGN PATENT DOCUMENTS

| | | | |
|---|---|---|---|
| DE | 19622207 | 12/1997 | C07F/5/02 |
| EP | 0 277 003 | 1/1988 | C08F/4/64 |
| WO | WO 99/06449 | 2/1999 | C08F/4/643 |
| WO | WO 99/42467 | 8/1999 | C07F/5/02 |

OTHER PUBLICATIONS

S.H. Strauss, "The Search for Larger and More Weakly Coordinating Anions," *Chem. Rev.*, 93, 927–942 (1993).
Baird, Michael C., et al, "$\eta^5$–$C_5Me_5TiMe_3B(C_6F_5)_3$: A Carbocationic Olefin Polymerization Initiator Masquerading as a Ziegler–Natta Catalyst," *J. Am. Chem. Soc.* 1994, 116, 6435–6436.

*Primary Examiner*—Mark L. Bell
*Assistant Examiner*—J. Pasterczyk

(57) ABSTRACT

Zwitterionic compositions of matter comprising cations [Ct]⁺ and anions connected together with substantially rigid fluorinated linking groups are described. These zwitterionic compositions serve as cocatalysts. They activate olefin polymerization catalysts, and can dissolve in aliphatic solvents. Synthesis and polymerization are illustrated.

33 Claims, No Drawings

FLUORINATED ZWITTERIONIC COCATALYST ACTIVATORS FOR OLEFIN POLYMERIZATION

RELATED CASES

This application claims the priority benefit of U.S. Provisional applications, 60/246,302 and 60/274,788, filed on Nov. 6, 2000 and Mar. 9, 2001 respectively.

FIELD OF INVENTION

This invention relates to polymerization cocatalyst compounds containing weakly coordinating Group-13-element anions and to the preparation of olefin polymers using ionic catalyst systems based on organometallic transition-metal cationic compounds stabilized by these anions.

BACKGROUND OF THE INVENTION

The term "noncoordinating anion" (NCA) is now accepted terminology in the field of olefin and vinyl molecule, coordination, insertion, and carbocationic polymerization. See, for example, EP 0 277 003, EP 0 277 004, U.S. Pat. Nos. 5,198,401, 5,278,119, and Baird, Michael C., et al, *J. Am. Chem. Soc.* 1994, 116, 6435–6436. The noncoordinating anions are described to function as electronic stabilizing cocatalysts, or counterions, for active, cationic metallocene polymerization catalysts. The term noncoordinating anion applies both to truly noncoordinating anions and to coordinating anions that are labile enough to undergo replacement by olefinically or acetylenically unsaturated molecules at the insertion site. These noncoordinating anions can be effectively introduced into a polymerization medium as Bronsted acid salts containing charge-balancing countercations, as ionic cocatalyst compounds, or mixed with an organometallic catalyst before adding it to the polymerization medium. See also, the review articles by S. H. Strauss, "The Search for Larger and More Weakly Coordinating Anions," *Chem. Rev.,* 93, 927–942 (1993).

U.S. Pat. No. 5,502,017, to Marks et al., addresses ionic metallocene catalysts for olefin polymerization containing a weakly coordinating anion comprising boron substituted with halogenated aryl substituents preferably containing silylalkyl substitution, such as a t-butyldimethyl-silyl substitution. Marks et al. disclose the weakly coordinating anion as the cocatalyst. The silylalkyl substitution is said to increase the solubility and thermal stability of the resulting metallocene salts. Examples 3–5 describe synthesis of and polymerization with the cocatalyst compound triphenylcarbenium tetrakis (4-dimethyl-t-butylsilyl-2,3,5,6-tetrafluorophenyl) borate.

In view of the above, there is a continuing need for olefin polymerization activators both to improve the industrial economics of solution polymerization and to provide alternative activating compounds for ionic, olefin polymerization catalyst systems.

SUMMARY OF THE INVENTION

The invention provides zwitterionic cocatalyst compounds that can be combined with catalyst precursor compounds to form active catalysts for olefin insertion, coordination, or carbocationic polymerization, as well as catalyst systems containing such cocatalyst and catalyst precursor compounds. (For purposes of this document, "cocatalyst compound" is interchangeable with "cocatalyst activator compound" and "activator"). Olefin polymerization can proceed by catalyst formation followed by, or in situ catalyst formation essentially concurrent with, contacting the catalyst with appropriate molecules: those having accessible, olefinic or acetylenic unsaturation or having olefinic unsaturation capable of cationic polymerization. More generally, an appropriate molecule is one that is polymerizable by a catalyst system that uses the invention zwitterionic cocatalyst compounds. Invention catalysts are suitable for preparing polymers and copolymers from olefinically and acetylenically unsaturated molecules. These zwitterionic cocatalyst compounds contain both an anion and a cation within the same molecule. The cocatalyst's anionic portion contains a Group-13 element bound to fluoroaryl ligands in which at least one fluoroaryl ligand is substituted with at least one cationic ammonium group. The proton from the cationic ammonium group can extract an alkyl group from, or break a carbon-metal bond in, an organometallic compound (i.e., the catalyst precursor) upon contact with the compound. This process leaves a cationic catalyst and a neutral amine substitution on at least one fluoroaryl ligand of the Group-13-based noncoordinating anion (the 'formerly' zwitterionic, cocatalyst compound).

An invention cocatalyst activator compound can be represented by the following formula:

$(ArF)_3 MC_n F_{n-2} NR_2 H$

Where —$NR_2H$ is a cationic moiety or pendant group. This moiety can abstract an alkyl group, or break a carbon-metal bond of the catalyst precursor (to activate it). M is a Group-13 element; some embodiments select boron or aluminum; ArF is a fluorinated aryl group; and each R is independently selected from $C_1$–$C_{30}$ hydrocarbyl or hydrocarbylsilyl substituents. Some embodiments attach R to the silicon atom through a secondary or tertiary carbon atom.

DETAILED DESCRIPTION OF THE INVENTION

Schematically, the zwitterionic cocatalyst can be represented as

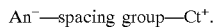

$An^-$—spacing group—$Ct^+$.

$An^-$ represents an anionic portion, $Ct^+$ represents a cationic portion, and 'spacing group' represents a molecular portion that connects between $An^-$ and $Ct^+$.

$An^-$ is a molecular anionic portion that is capable of stabilizing or charge balancing the active catalyst when combined with 'spacing group' and neutralized $Ct^+$ and is otherwise stable in the desired polymerization process. Selecting $An^-$ with a Group-13 central atom is useful. Group-13 elements are sometimes referred to as triels, abbreviated Tr. Some embodiments select the triel to be B or Al. Fluorinated aryl ligands, Arf, sometimes serve as the ligands of $An^-$. For instance, exemplary molecular anionic portions are $(ArF)_3B^-$— and $(ArF)_3Al^-$—.

The ligands around the Group-13 atom serve to stabilize the charge on the ion. Furthermore, the ligands control the degree of contact between the catalyst and cocatalyst. With appropriate $An^-$, these two effects diminish the ionic attraction between the catalyst and cocatalyst. Alternatively, $An^-$ can be an assembly in which the anionic charge spreads out over the molecule making the charge more diffuse. After catalyst activation, the cocatalyst should either be completely non-coordinating or coordinate weakly enough so that the anion does not substantially impede the monomer's access to the catalyst.

Phenyl, biphenyl, naphthyl, indenyl, anthracyl, fluorenyl, azulenyl, phenanthrenyl, and pyrenyl are suitable aryl radicals. Some embodiments select phenyl, biphenyl, or naphthyl as the aryl radicals. Exemplary invention ArF ligands specifically include the listed aryl radicals as fluorinated aryl groups. Perfluorinated aryl groups also function and include substituted ArF groups having substituents in addition to fluorine, such as fluorinated hydrocarbyl groups. The disclosures of U.S. Pat. Nos. 5,198,401, 5,296,433, 5,278,119, 5,447,895, 5,688,634, 5,895,771, WO 93/02099, WO 97/29845, WO 99/43717, WO 99/42467 and copending U.S. application Ser. Number 09/261,627, filed 3 Mar. 1999, and its equivalent WO 99/45042 teach suitable ArF groups. Some embodiments replace at least one-third of the hydrogen atoms connected to aromatic ligands with fluorine; some embodiments select perfluorinated aryl ligands. Perfluorinated means that each aryl hydrogen atom is substituted with fluorine or fluorcarbyl substituents, e.g., trifluoromethyl, pentafluoroethyl, heptafluoroisopropyl, tris(trifluoromethyl) silyltetrafluoroethyl, and bis(trifluoroethyl) (heptafluoropropyl)silyltetrafluoroethyl. The goal of fluorination is to remove abstractable hydrogen from the NCA. Therefore, any ligand choice or substitution pattern that minimizes the number of abstractable hydrogen is useful in this invention's practice. When the number of abstractable hydrogen has been minimized (that is when the competing hydrogen abstraction reaction is small enough that the polymerization reaction proceeds in a commercially reasonable manner), the NCA is referred to as substantially fluorinated. Thus, suitable ligand choices and substitution patterns will depend somewhat on the selected catalyst. Not all hydrogen substituents must be fluorine-replaced as long as the remaining hydrogen substituents are substantially non-abstractable by the specific catalyst of the system. Substantially non-abstractable means that the hydrogen may be extractable but at levels low enough so that the degree of chain termination and catalyst poisoning remains below that which is commercially reasonable. Some embodiments target lesser levels of abstractability.

'Spacing group' or 'spacer,' the bridge between An⁻ and Ct⁺, is any organic group that is large enough and rigid enough to maintain separation between An⁻ and Ct⁺. In most cases, the spacing group is a fluorinated aryl ring connected at one end to the cation and at the other end to the anion. Some embodiments select spacing groups that limit the quantity of activated-catalyst-abstractable hydrogen on the cocatalyst. To the extent that hydrogen atoms on the spacing group are abstractable by the activated catalyst, these hydrogen atoms will be fluorine substituted in some embodiments. Perfluorinated spacing groups are useful. Additionally, fluorine substitutions on the spacing group allow the anion's electron density to spread over more atoms, which makes the electron density more diffuse. Increased anion diffuseness causes weakened anion coordination to the catalyst after activation. Thus, fluorine substitution on the spacing group is believed to improve the catalyst's activity. Finally, fluorine substitution on the spacing group improves the robustness or thermal stability of the resulting NCA.

Representative spacing group radicals include, but are not limited to, fluorobenzyl, difluorobenzyl, difluoronaphthyl, hexafluoroanthracyl, hexafluorofluorenyl, hexafluoroindenyl, hexafluorophenathracyl, hexafluoropyrenyl, nonafluoroanthracyl, nonafluorophenathracyl, nonafluoropyrenyl, octafluoroanthracyl, octafluorofluorenyl, octafluorophenathracyl, octafluoropyrenyl, pentafluoroanthracyl, pentafluorofluorenyl, pentafluoroindenyl, pentafluoronaphthyl, pentafluorophenathracyl, pentafluoropyrenyl, perfluoroanthracyl, perfluorobenzyl, perfluorofluorenyl, perfluoroindenyl, perfluoronaphthyl, perfluorophenathracyl, perfluoropyrenyl, heptafluoroanthracyl, heptafluorofluorenyl, heptafluoroindenyl, heptafluorophenathracyl, heptafluoropyrenyl, tetrafluoroanthracyl, tetrafluorofluorenyl, tetrafluoroindenyl, tetrafluoronaphthyl, tetrafluorophenathracyl, tetrafluoropyrenyl, trifluoroanthracyl, trifluorobenzyl, trifluorofluorenyl, trifluoroindenyl, trifluoronaphthyl, trifluorophenathracyl, and trifluoropyrenyl radicals.

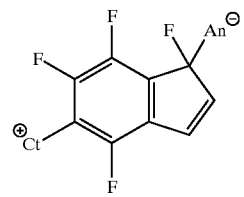

1,4,6,7-tetrafluoro-indenyl Serving as a Spacing Group

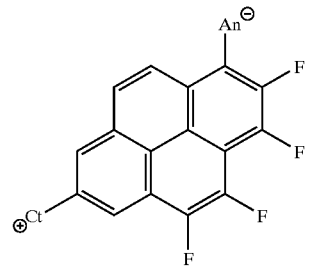

2,3,4,5-tetrafluoropyryl Serving as a Spacer

Effective cationic groups (—Ct⁺) are those known to abstract a ligand (Q), such as monoanionic hydride, alkyl, or other hydrocarbyl or hydrocarbylsilyl ligands, from organometallic catalyst precursor compounds leaving active catalysts. After abstraction, the Ct portion of the cocatalyst is substantially neutral. In some embodiments, —Ct is chosen so that it doesn't interfere with polymerization. Useful cationic groups include, but are not limited to, nitrogen-containing groups such as the ammonium salts of U.S. Pat. No. 5,198,401, and WO 97/35893, the trityl carbenium groups of US Pat. No. 5,387,568, the silylium cationic groups of WO 96/08519. Additionally, suitable cations include nitrogen- and carbon-based cations described in WO 97/35893, and in copending U.S. Applications Serial Nos. 60/160,942, filed 22 Oct. 1999, and 60/169,768, filed 9 Dec. 1999. A useful cationic moiety is —NR₂H.

Essentially any of the defined R groups will be effective for zwitterionic cocatalyst activator use. The cocatalyst activators can effectively activate catalysts for solution, bulk, slurry, and gas phase polymerization processes. Exemplary R groups include methyl, ethyl, n-propyl, iso-propyl, n-butyl, butyl, cyclohexyl, benzyl, methyltrimethylsilyl, methyltriethylsilyl, pyrrolidinyl, piperidinyl, 2,6-dimethyl piperidinyl, etc. The R groups may be the same or different, in other words mixed alkyl groups may be located on the Group-15 atom. An exemplary, but non-inclusive, list of —Ct⁺ are provided in the list below. The listings show a cationic central atom with two substituents. In most cases, the —Ct⁺ moiety additionally connects to the spacing group and to a proton; thus the central atom has four ligands.

Ammonium Cation Moieties (3-methylpentyl) (ethyl(triethylsilyl)) ammonium; (3-methylpentyl)-1,2-difluorohexyl-ammonium; (3-methylpentyl)-2,3,5-trifluorophenyl-ammonium; (3-methylpentyl)butyl ammonium; (3-methylpentyl)hexyl ammonium; (3-methylpentyl)octyl ammonium; (3-methylpentyl)perfluorobutyl ammonium; (3-methylpentyl)perfluoroheptyl ammonium; (3-methylpentyl)perfluoropropyl ammonium; (3-methylpentyl)phenyl ammonium; (ethyl(triethylsilyl)) (ethyl(triethylsilyl)) ammonium; (ethyl(triethylsilyl)) (methyl(trimethylsilyl)) ammonium; (ethyl(triethylsilyl)) isohexyl ammonium; (ethyl(triethylsilyl))isopropyl ammonium; (ethyl(triethylsilyl))perfluoroethyl ammonium; (ethyl (triethylsilyl))perfluoropentyl ammonium; (ethyl (triethylsilyl))perfluorophenyl ammonium; (ethyl (trimethylsilyl))-2,3,5-trifluorophenyl-ammonium; (ethyl (trimethylsilyl))-2,3,5-trifluorophenyl-ammonium; (ethyl (trimethylsilyl))hexyl ammonium; (ethyl(trimethylsilyl)) isohexyl ammonium; (methyl(triethylsilyl))butyl ammonium; (methyl(triethylsilyl))isopentyl ammonium; (methyl(triethylsilyl))perfluoroheptyl ammonium; (methyl (triethylsilyl))perfluoromethyl ammonium; (methyl (triethylsilyl))perfluorooctyl ammonium; (methyl (triethylsilyl))perfluorophenyl ammonium; (methyl (triethylsilyl))perfluoropropyl ammonium; (methyl (triethylsilyl))perfluoropropyl ammonium; (methyl (triethylsilyl))phenyl ammonium; (methyl(trimethylsityl)) (3-methylpentyl) ammonium; (methyl(trimethyl-silyl)) (methyl(trimethylsilyl)) ammonium; (methyl (trimethylsilyl))-1,2-difluorohexyl-ammonium; (methyl (trimethylsilyl))ethyl ammonium; (methyl(trimethylsilyl)) perfluorobutyl ammonium; (methyl(trimethylsilyl)) perfluoroheptyl ammonium; (methyl(trimethylsilyl)) perfluorohexyl ammonium; (methyl(trimethylsilyl))propyl ammonium; 1,2-difluorohexyl(methyl(triethylsilyl)) ammonium; 1,2-difluorohexyl(methyl(triethylsilyl)) ammonium; 1,2-difluorohexyl(methyl(trimethylsilyl)) ammonium; 1,2-difluorohexyl-2,3,4,5-tetrafluorophenyl-ammonium; 1,2-difluorohexylperfluoro-t-butyl ammonium; 1,6-difluorohexyl(methyl(trimethylsilyl)) ammonium; 1,6-difluorohexyl-2,3,6,7-tetrafluorooctyl-ammonium; 1,6-difluorohexyl-2,3,6,7-tetrafluorooctyl-ammonium; 1,6-difluorohexylisohexyl ammonium; 1,6-difluorohexylperfluoroethyl ammonium; 1,6-difluorohexylperfluoroheptyl ammonium; 1,6-difluorohexylphenyl ammonium; 1,6-difluorohexylpropyl ammonium; 2,3,4,5-tetrafluorophenyl(3-methylpentyl) ammonium; 2,3,4,5-tetrafluorophenyl(ethyl(triethylsilyl)) ammonium; 2,3,4,5-tetra-fluorophenyl-1,6-difluorohexyl-ammonium; 2,3,4,5-tetrafluorophenyl-2,3,5-trifluorophenyl-ammonium; 2,3,4,5-tetrafluorophenyl-2,3,6,7-tetrafluorooctyl-ammonium; 2,3,4,5-tetrafluorophenylbutyl ammonium; 2,3,4,5-tetrafluorophenylethyl ammonium; 2,3,4,5-tetrafluorophenylisopentyl ammonium; 2,3,4,5-tetrafluorophenylisopropyl ammonium; 2,3,4,5-tetrafluorophenylperfluoroisopentyl ammonium; 2,3,4,5-tetrafluorophenylperfluoroisopentyl ammonium; 2,3,5-trifluorophenyl-1,2-difluorohexyl-ammonium; 2,3,5-trifuorophenyl-1,6-difluorohexyl-ammonium; 2,3,5-trifluorophenyl-2,3,4,5-tetrafluorophenyl-ammonium; 2,3,5-trifluorophenyl-2,3,6,7-tetrafluorooctyl-ammonium; 2,3,5-trifluorophenylmethyl ammonium; 2,3,5-trifluorophenylpentyl ammonium; 2,3,5-trifluorophenylperfluoropropyl ammonium; 2,3,5-trifluorophenylphenyl ammonium; 2,3,5-trifluorophenylphenyl ammonium; 2,3,6,7-tetrafluorooctyl (3-methylpentyl) ammonium; 2,3,6,7-tetrafluorooctylbutyl ammonium; 2,3,6,7-tetrafluorooctylisohexyl ammonium; 2,3,6,7-tetrafluorooctylisopropyl ammonium; 2,3,6,7-tetrafluorooctylpentyl ammonium; butyl-1,2-difluorohexyl-ammonium; butyl-2,3,5-trifluorophenyl-ammonium; butylperfluorohexyl ammonium; butylperfluorophenyl ammonium; butylpropyl ammonium; ethyl(methyl (triethylsilyl)) ammonium; ethylperfluoropropyl ammonium; heptyl(3-methylpentyl) ammonium; heptyl(3-methylpentyl) ammonium; heptylisohexyl ammonium; heptylisopentyl ammonium; heptylmethyl ammonium; heptylpentyl ammonium; heptylperfluorobutyl ammonium; hexyl-1,2-difluorohexyl-ammonium; hexyloctyl ammonium; hexyl-t-butyl ammonium; isohexyl(ethyl (triethylsilyl)) ammonium; isohexyl(ethyl(trimethylsilyl)) ammonium; isohexyl(methyl(trimethylsilyl)) ammonium; isohexyl-2,3,4,5-tetrafluorophenyl-ammonium; bis (isohexyl) ammonium; isohexylisohexyl ammonium; isohexylisopropyl ammonium; isohexylmethyl ammonium; isohexylperfluoroheptyl ammonium; isohexylperfluoropentyl ammonium; isohexylphenyl ammonium; isopentyl(ethyl (trimethylsilyl)) ammonium; isopentylheptyl ammonium; isopentylmethyl ammonium; isopentylperfluorohexyl ammonium; isopropyl(ethyl(triethylsilyl)) ammonium; isopropyl(methyl(triethylsilyl)) ammonium; isopropyl (methyl(triethylsilyl)) ammonium; isopropylheptyl ammonium; isopropylheptyl ammonium; isopropylisohexyl ammonium; isopropylperfluorobutyl ammonium; isopropylperfluorophenyl ammonium; isopropyl-t-butyl ammonium; isopropyl-t-butyl ammonium; methyl(ethyl(triethylsilyl)) ammonium; methyl(ethyl(triethylsilyl)) ammonium; methylperfluoroethyl ammonium; octylperfluoroethyl ammonium; octylperfluoroheptyl ammonium; octylpropyl ammonium; pentyl-1,6-difluorohexyl-ammonium; pentylisohexyl ammonium; pentylperfluorophenyl ammonium; perfluorobutyloctyl ammonium; perfluorobutylperfluoropropyl ammonium; perfluoroethyl(ethyl(triethylsilyl)) ammonium; perfluoroethyl(methyl(trimethylsilyl)) ammonium; perfluoroethyl-1,6-difluorohexyl-ammonium; perfluoroethylethyl ammonium; perfluoroheptyl(ethyl(triethylsilyl)) ammonium; perfluoroheptyl(methyl(triethylsilyl)) ammonium; perfluoroheptylbutyl ammonium; perfluoroheptylisohexyl ammonium; perfluoroheptylperfluorobutyl ammonium; perfluoroheptylperfluorohexyl ammonium; perfluoroheptylperfluoroisopropyl ammonium; perfluoroheptylperfluoromethyl ammonium; perluorohexyl(ethyl (triethylsilyl)) ammonium; perfluorohexyl(ethyl (triethylsilyl)) ammonium; perfluorohexyl(methyl (triethylsilyl)) ammonium; perfluorohexylethyl ammonium; perfluorohexylperfluoroheptyl ammonium; perfluorohexylperfluoromethyl ammonium; perfluorohexylperfluoropentyl ammonium; perfluorohexylperfluoropentyl ammonium; perfluoroisopentylisohexyl ammonium; perfluoroisopentylisohexyl ammonium; perfluoroisopentylpentyl ammonium; perfluoroisopentylpropyl ammonium; perfluoroisopropyl(3-methylpentyl) ammonium; perfluoroisopropyl(ethyl (triethylsilyl)) ammonium; perfluoroisopropyl-2,3,4,5-tetrafluorophenyl-ammonium; perfluoroisopropylhexyl ammonium; perfluoroisopropyloctyl ammonium; perfluoroisopropylperfluoroheptyl ammonium; perfluoroisopropylperfluorohexyl ammonium; perfluoroisopropylperfluoroisopentyl ammonium; perfluoromethyl-1,2-difluorohexyl-ammonium; perfluoromethylperfluoroisopropyl ammonium; perfluoromethylperfluorooctyl ammonium; perfluoromethylperfluoro-t-butyl ammonium; perfluoromethylphenyl ammonium; perfluoromethylpropyl ammonium; perfluorooctyl(methyl(triethylsilyl)) ammonium; perfluorooctyl(methyl(trimethylsilyl)) ammonium; perfluorooctyl-1,6-difluorohexyl-ammonium; perfluorooctylethyl ammonium; perfluorooctylpentyl ammonium; perfluorooctylperfluorooctyl ammonium; perfluoropentyl(ethyl (triethylsilyl)) ammonium; perfluoropentyl(ethyl (trimethylsilyl)) ammonium; perfluoropentylmethyl ammonium; perfluoropentylmethyl ammonium; perfluoropentylperluorobutyt ammonium; perfluoropentylperfluoroethyl ammonium; perfluoropentylphenyl ammonium; perfluoropentylpropyl ammonium; perfluorophenyl(methyl (triethylsilyl)) ammonium; perfluorophenyl-1,2-difluorohexyl-ammonium; perfluorophenyl-1,6-difluorohexyl-ammonium; perfluorophenylethyl ammonium; perfluorophenylhexyl ammonium; perfluorophenylperfluoroheptyl ammonium; perfluorophenylperfluoromethyl ammonium; perfluorophenyl-t-butyl ammonium; perfluoropropyl(methyl(triethylsilyl)) ammonium; perfluoropropyl-2,3,5-trifluorophenyl-ammonium; perfluoropropyl-2,3,5-trifluorophenyl-ammonium; perfluoropropyl-2,3,6,7-tetrafluorooctyl-ammonium; perfluoropropylphenyl ammonium; perfluoro-t-butylhexyl ammonium.

Phosphonium Cation Moieties di(3-methylpentyl) phosphonium; (3-methylpentyl)-1,6-difluorohexyl-phosphonium; (3-methylpentyl)-2,3,6,7-tetrafluorooctyl-phosphonium; (3-methylpentyl)hexyl phosphonium; (3-methylpentyl)perfluoro-t-butyl phosphonium; (3-methylpentyl)perfluoro-t-butyl phosphonium; (3-methylpentyl)perfluoro-t-butyl phosphonium; (3-methylpentyl)propyl phosphonium; (ethyl(triethylsilyl)) perfluoromethyl phosphonium; (ethyl(trimethylsilyl)) (methyl(triethylsilyl)) phosphonium; (ethyl(triethylsilyl)) perfluorobutyl phosphonium; (ethyl(trimethylsilyl))propyl phosphonium; (methyl(triethylsilyl))(methyl(triethylsilyl)) phosphonium; (methyl(triethylsilyl)) (methyl (trimethylsilyl)) phosphonium; (methyl(triethylsilyl))octyl phosphonium; (methyl(triethylsilyl))perfluoroisopentyl phosphonium; (methyl(triethylsilyl))perfluoroisopentyl phosphonium; (methyl(trimethylsilyl))perfluoroisopropyl phosphonium; 1,2-difluorohexyl-2,3,5-trifluorophenyl-phosphonium; 1,6-difluorohexyl-2,3,5-trifluoro-phenyl-phosphonium; 1,6-difluorohexylisopentyl phosphonium; 2,3,5-trifluorophenylmethyl phosphonium; butylisohexyl phosphonium; ethylperfluorophenyl phosphonium; diheptyl phosphonium; heptylperfluorohexyl phosphonium; heptylperfluoroisopropyl phosphonium; heptylperfluoropentyl phosphonium; hexylperfluorophenyl phosphonium; isohexyl(3-methylpentyl) phosphonium; isohexylperfluoroisopentyl phosphonium; isopentyl(ethyl(triethylsilyl)) phosphonium; isopentylbutyl phosphonium; methylhexyl phosphonium; methylisopropyl phosphonium; octylbutyl phosphonium; pentyl(methyl(triethylsilyl)) phosphonium; pentyl(methyl(trimethylsilyl)) phosphonium; pentylisohexyl phosphonium; pentylpernluorooctyl phosphonium; perfluorobutylperfluoroethyl phosphonium; perfluoroheptylisopentyl phosphonium; perfluoroheptylperfluoromethyl phosphonium; perfluorohexyl(3-methylpentyl) phosphonium; perfluorohexyl-2,3,5-trifluorophenyl-phosphonium; perfluoroisopentyl(ethyl(trimethylsilyl)) phosphonium; perfluoroisopentylisohexyl phosphonium; perfluoroisopropylperfluorohexyl phosphonium; perfluoromethylisohexyl phosphonium; perfluorooctyl(methyl(trimethylsiiyl)) phosphonium; perfluoropropyl-1,2-difluorohexyl-phosphonium; perfluoropropylperfluoroheptyl phosphonium; perfluoro-t-butylphenyl phosphonium; phenyl(methyl (triethylsilyl))phosphonium; propyloctyl phosphonium; t-butyl(methyl(triethylsilyl)) phosphonium; t-butyl-t-butyl phosphonium.

Arsonium Cation Moieties

Examples of —Ct$^+$ based on arsonium include, but are not limited to (3-methylpentyl)butylarsonium; (ethyl (trimethylsilyl))-t-butylarsonium; (ethyl(trimethylsilyl))-t-butylarsonium; (methyl(triethylsilyl)) (ethyl(triethylsilyl)) arsonium; (methyl(trimethylsilyl))-2,3,5-trifluorophenyl-arsonium; (methyl(trimethylsilyl))-t-butylarsonium; 1,2-difluorohexyl(methyl(trimethylsilyl))arsonium; 2,3,4,5-tetrafluorophenylisopropylarsonium; hexylperfluoromethylarsonium; hexylperfluoropentylarsonium; isohexyl-1,6-difluorohexyl-arsonium; isopentylisopropylarsonium; isopropyl(ethyl(triethylsilyl)) arsonium; methylbutylarsonium; pentylperfluoromethylarsonium; pentylperfluorophenylarsonium; perfluoroheptylperfluoroheptylarsonium; perfluoroheptylperfluoroisopentylarsonium; perfluoroisopentylperfluorohexylarsonium; perfluoroisopropylperfluoroethylarsonium; perfluoromethyl (methyl(trimethylsilyl))arsonium; perfluorooctylperfluoromethylarsonium; perfluoropropylperfluorophenylarsonium; perfluoro-t-butyl-1,6-difluorohexyl-arsonium; perfluoro-t-butylperfluoroisopentylarsonium; phenyl (methyl(triethylsilyl))arsonium; phenylperfluorobutylarsonium; propylisopropylarsonium; t-butyl-2,3,4,5-tetrafluorophenyl-arsonium; t-butylperfluoroheptylarsonium; t-butylperfluoromethylarsonium.

In operation, the zwitterionic cocatalyst reacts with the catalyst precursor leaving an activated cationic catalyst and a weakly coordinating anion. Before activation, the cocatalyst contains a cationic portion. Activation occurs when that cationic portion either abstracts a hydride, alkyl, or substituted alkyl ligand, Q, from the catalyst precursor or cleaves a metal-organic bond in the precursor.

Activation transforms the neutral, but zwitterionic, cocatalyst into an anion; the cationic portion of the cocatalyst is neutralized, typically by loss of a proton. Activation also transforms the neutral catalyst precursor into a cationic catalyst, typically by abstracting a hydride or anionic alkyl, which combines with the proton from the cocatalyst. For example,

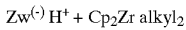
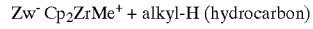

Thus, invention embodiments comprise zwitterionic cocatalysts. Some embodiments are catalyst systems comprising catalyst precursor and zwitterionic cocatalyst. Some embodiments comprise catalysts that are the contact product of a catalyst precursor and a zwitterionic cocatalyst. When the zwitterionic cocatalyst contacts the catalyst precursor, a hydrogen from the cationic moiety abstracts an organic radical from the catalyst precursor. This process transforms the neutral catalyst precursor into a cationic catalyst, in some embodiments an olefin polymerization catalyst; the neutral zwitterionic cocatalyst is transformed into an anionic NCA that can charge balance the NCA. As stated above, inventor zwitterionic cocatalysts are useful in activating olefin polymerization catalyst precursors. Additionally, these cocatalysts can activate olefin polymerization catalysts, ring-opening catalysts, etc., as is know in the art.

Zwitterionic activators or cocatalysts may be prepared as follows. A secondary amine, NR$_2$H is reacted with bromoperfluoroaryl to form N-(bromoperfluoroaryl)NR$_2$. After preparing the aryl amine, butyl lithium and then tris (pentafluoroaryl)borane are added. This reaction produces boron substitution at the aryl amine's para position. (The borane's aryl groups need not be the same; likewise, the borane's aryl groups need not match those of the aryl amine.) Hydrogen chloride gas is then added yielding a zwitterionic cocatalyst. Suitable fluoroaryl substituents on the nitrogen atom can be any of the known, fluorinated $C_6$ to $C_{12}$ aromatic rings, preferably phenyl, naphthyl, or biphenyl. Perfluorinated $C_6$ to $C_{12}$ rings are useful.

A specific synthesis of an invention cocatalyst is set out below. Pyrrolidine is reacted with pentafluorobromobenzene to form N-(4-bromo-2,3,5,6-pentafluorophenyl)pyrrolidene. After preparing the phenyl amine, butyl lithium and then tris(pentafluorophenyl)borane is added to the reaction resulting in boron substitution at the para position of the bromopentafluorophenyl pyrrolidene. Hydrogen chloride gas is added yielding a zwitterion containing an anionic borate portion and a cationic ammonium portion as shown below.

993, 5,491,246, 5,512,693, EP-A-0 418 044, EP-A-0 591 756, WO-A-92/00333, WO-A-94/01471 and WO 97/22635.) Such metallocenes can be described as mono- or biscyclopentadienyl-substituted Group-3, -4, -5, or -6 transition metals. The transition metal ligands may themselves be substituted with one or more groups, and the ligands may bridge to each other or bridge through a heteroatom to the transition metal. The size and constituency of the ligands and bridging elements are not critical to this invention's catalyst systems, but should be chosen in the literature-described manner to enhance activity and to select desired characteristics. Embodiments in which the cyclopentadienyl rings (including substituted, cyclopentadienyl-based, fused-ring systems, such as indenyl, fluorenyl, azulenyl, or their substituted analogs), when bridged to each other, are lower-alkyl substituted ($C_1$–$C_6$) in the 2 position (with or without a similar 4-position substituent in the fused ring are useful). The cyclopentadienyl rings may additionally comprise alkyl, cycloalkyl, aryl, alkylaryl, and arylalkyl substituents, the

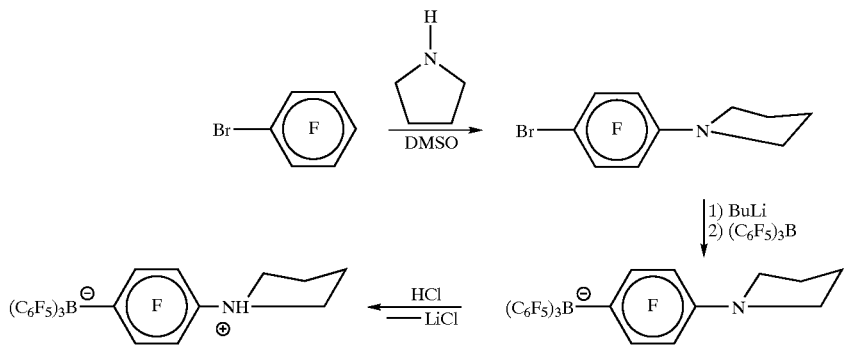

Suitable catalyst precursor compounds for use in this invention include the known organometallic, transition metal compounds useful for traditional Ziegler-Natta polymerization, particularly the metallocenes known to be useful in polymerization. The catalyst precursor must be susceptible to activation by invention cocatalysts. Useful catalyst precursors include Group-3–10 transition metal compounds in which at least one metal ligand can be abstracted by the cocatalysts. Particularly those abstractable ligands include hydride, hydrocarbyl, hydrocarbylsilyl, and their lower-alkyl-substituted ($C_1$–$C_{10}$) derivatives. Examples include hydride, methyl, benzyl, dimethylbutadiene, etc. Abstractable ligands and transition metal compounds comprising them include those metallocenes described in, for example, U.S. Pat. No. 5,198,401 and WO 92/00333. Syntheses of these compounds are well known from the published literature. Additionally, in those cases where the metal ligands include labile halogen, amido, or alkoxy ligands (for example, biscyclopentadienyl zirconium dichloride), which may not allow for ready abstraction with invention cocatalysts, the ligands can be replaced with abstractable ones. This replacement uses known routes such as alkylation with lithium or aluminum hydrides, alkyls, alkylalumoxanes, Grignard reagents, etc. See also EP 0 500 944 and EP 0 570 982 for the reaction of organoaluminum compounds with dihalo-substituted metallocenes prior to catalyst activation.

Additional descriptions of metallocene compounds with, or that can be alkylated to contain, at least one ligand abstractable to form catalytically active transition-metal cations appear in the patent literature. (E.g., EP-A-0 129 368, U.S. Pat. Nos. 4,871,705, 4,937,299, 5,324,800, 5,470, latter as linear, branched, or cyclic structures including multi-ring structures, for example, those of U.S. Pat. Nos. 5,278,264 and 5,304,614. Such substituents should each have essentially hydrocarbyl characteristics and will typically contain up to 30 carbon atoms, but may contain heteroatoms, such as 1 to 5 non-hydrogen or non-carbon atoms, e.g., N, S, O, P, Ge, B and Si.

Invention activators are useful with essentially all known metallocene catalyst that are suitable for preparing polyethylene, polypropylene, or ethylene-containing copolymers (where copolymer means a polymer prepared using at least two different monomers), see again WO-A-92/00333 and U.S. Pat. Nos. 5,001,205, 5,198,401, 5,324, 800, 5,304,614 and 5,308,816, for specific listings. Criteria for selecting suitable metallocene catalysts for making polyethylene and polypropylene are well known in the art, in both patent and academic literature, see for example *Journal of Organometallic Chemistry* 369, 359–370 (1989). Likewise, methods for preparing these metallocenes are also known. Typically, the catalysts are stereorigid, asymmetric, chiral, or bridged chiral, metallocenes. See, for example, U.S. Pat. Nos. 4,892,851, 5,017,714, 5,296,434, 5,278,264, WO-A-(PCT/US92/10066) WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al, *Organometallics* 1994, 13, 954–963, and "ansa-Zirconocene Polymerization Catalysts with Annelated Ring Ligands-Effects on Catalytic Activity and Polymer Chain Lengths", Brinzinger, H., et al, *Organometallics* 1994, 13, 964–970, and documents referred to therein. Though many of these references deal with alumoxane-activated catalyst systems, analogous metallocenes can be activated with invention cocatalysts. In catalyst systems lacking abstractable ligands, at least one non-abstractable ligand must first be replaced with an abstractable one. Replacement by alkylation, as described above, is one example. Additionally, the metallocenes should contain a group into which an ethylene or α-olefin group, —C=C—, may insert, for example, hydride, alkyl, alkenyl, or silyl. See additional description in G. G. Hlatky, "Metallocene catalysts for olefin polymerization Annual review of 1996", *Coordination Chemistry Reviews*, 181, 243–296 (El-sevier Science, 1999).

Representative metallocene compounds can have the formula:

where Mc is a Group-3–10 metal; $L_A$ is a substituted or unsubstituted, cyclopentadienyl or heterocyclopentadienyl ligand, connected to Mc; and $L_B$ is a ligand as defined for $L_A$, or is J, a heteroatom ligand connected to Mc. $L_A$ and $L_B$ may ridge to each other through a Group-13-to-16-element-containing bridge. $L_{Ci}$ is an optional, neutral, non-oxidizing ligand connected to Mc (i equals 0 to 3); and D and E are the same or different labile ligands, optionally bridged to each other, $L_A$, or $L_B$. Each of D and E are connected to Mc.

D and E's identity is functionally constrained. The first constraint is that upon activation, either the D—Mc or the E—Mc connection must break. D and E should be chosen to facilitate this. Another constraint is that a polymerizable molecule must be able to insert between Mc and whichever of D or E remains.

In addition to in-ring and on-ring substituted and unsubstituted cyclopentadienide ion, a cyclopentadienyl also encompasses fused-ring systems including but not limited to indenyl and fluorenyl radicals. Also, the use of heteroatom-containing rings or fused rings, where a non-carbon, Group-13, -14, -15, or -16 atom replaces a ring carbon is within the term "eyclopentadienyl" for this specification. See, for example, the background and illustrations of WO 98/37106, having priority with U.S. Ser. No. 08/999,214, filed Dec. 29, 1997, and WO 98/41530, having priority with U.S. Ser. No. 09/042,378, filed Mar. 13, 1998. Substituted cyclopentadienyl structures are structures in which one or more hydrogen atoms are replaced by a hydrocarbyl, hydrocarbylsilyl, or similar heteroatom-containing structure. Hydrocarbyl structures specifically include $C_1$–$C_{30}$ linear, branched, and cyclic alkyl, and aromatic fused and pendant rings. These rings may also be substituted with ring structures.

Non-limiting representative metallocene compounds include mono-cyclopentadienyl compounds such as pentamethylcyclopentadienyltitanium isopropoxide, pentamethylcyclopentadienyltribenzyl titanium, dimethylsilyltetramethyl-cyclopentadienyl-tert-butylamido titanium dichloride, pentamethylcyclopentadienyl titanium trimethyl, dimethylsilyltetramethylcyclopentadienyl-t-butylamido zirconium dimethyl, dimethylsilyltetramethylcyclopentadienyl-dodecylamido hafnium dihydride, dimethylsilyltetramethylcyclopentadienyl-dodecylamido hafnium dimethyl, unbridged biscyclopentadienyl compounds such as bis(1-methyl, 3-butylcyclopentadienyl) zirconium dimethyl, (pentamethylcyclopentadienyl-cyclopentadienyl) zirconium dimethyl, (tetramethylcyclopentadienyl)(n-propylcyclopentadienyl) zirconium dimethyl; bridged bis-cyclopentadienyl compounds such as dimethylsilylbis(tetrahydroindenyl) zirconium dichloride and silacyclobutyl (tetramethylcyclopentadienyl)(n-propyl-cyclopentadienyl) zirconium dimethyl; bridged bis-indenyl compounds such as dimethylsily (bisindenyl) zirconium dichloride, dimethylsily (bisindenyl) hafnium dimethyl, dimethylsilyl-bis(2-methylbenzindenyl) zirconium dichloride, dimethylsilylbis (2-methylbenzindenyl) zirconium dimethyl; and fluorenyl-ligand-containing compounds, e.g., diphenylmethyl (fluorenyl)(cyclopentadienyl)zirconium dimethyl; and the additional mono- and biscyclopentadienyl compounds such as those listed and described in U.S. Pat. Nos. 5,017,714, 5,324,800, WO 92/00333 and EP-A-0 591 756.

Additional compounds suitable as olefin polymerization catalysts for use in this invention will be any of those Group-3 to -10 compounds that can be converted by ligand abstraction or bond scission into a cationic catalyst and stabilized in that state by a noncoordinating or weakly coordinating anion that is sufficiently labile to be displaced by an olefinically unsaturated molecules such as ethylene.

Exemplary compounds include those described in the patent literature. International patent publications WO 96/23010, WO 97/48735 and Gibson, et al., *Chem. Comm.*, pp. 849–850 (1998), which disclose diimine-based ligands for Group-8 to -10 compounds that undergo ionic activation and polymerize olefins. Polymerization catalyst systems from Group-5–10 metals, in which the active center is highly oxidized and stabilized by low-coordination-number, polyanionic, ligand systems, are described in U.S. Pat. No. 5,502,124 and its divisional U.S. Pat. No. 5,504,049. See also the Group-5 organometallic catalyst compounds of U.S. Pat. No. 5,851,945 and the tridentate-ligand-containing, Group-5–10, organometallic catalysts of copending U.S. application Ser. No. 09/302,243, filed 29 Apr. 1999, and its equivalent PCT/US99/09306. Group-11 catalyst precursor compounds, activable with ionizing cocatalysts, useful for olefin and vinylic polar molecules are described and exemplified in WO 99/30822 and its priority documents, including U.S. patent application Ser. No. 08/991,160, filed 16 Dec. 1997.

U.S. Pat. No. 5,318,935 describes bridged and unbridged, bisamido catalyst compounds of Group-4 metals capable of α-olefin polymerization. Bridged bis(arylamido) Group-4 compounds for olefin polymerization are described by D. H. McConville. et al., in *Orgaionetallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition metal compounds include those described in WO 96/40805. Cationic Group-3- or Lanthanide-metal olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors, which can be activated with this invention's ionic cocatalysts. Also, those compounds disclose in "Living Polymerization of α-Olefins by Chelating Diamide Complexes of Titanium", *J. Am. Chem. Soc.*, 1996, 118, 10008.

Bis amide catalyst precursors are useful with invention cocatalysts. Bisamide catalyst precursors are those precursors that have the following formula:

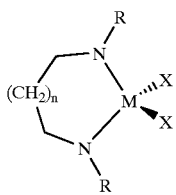

M is Ti, Zr, or Hf. R are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the bisamide catalyst precursor must first be chemically modified to transform X into an abstractable ligand. This can be done by alkylation, for example.

Pyridine bisamide catalyst precursors are also useful with invention co-catalysts. Pyridine bisamide catalyst precursors are those precursors that have the following formula:

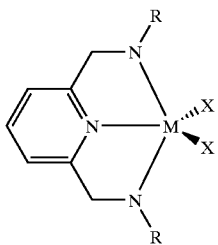

M is Ti, Zr, or Hf. R are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the pyridine bisamide catalyst precursor must first be chemically modified to transform X into an abstractable ligand. This can be done by alkylation, for example.

Amine bisamide catalyst precursors are also useful with invention co-catalysts. Amine bisamide catalyst precursors are those precursors that have the following formula:

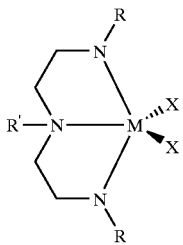

M is Ti, Zr, or Hf. R and R' are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the amine bisamide catalyst precursor must first be chemically modified to transform X into an abstractable ligand. This can be done by alkylation, for example.

The literature contains many additional descriptions of suitable catalyst-precursor compounds. Compounds that contain abstractable ligands or that can be alkylated to contain abstractable ligands are suitable for the practice of this invention. See, for instance, V. C. Gibson, et al; "The Search for New-Generation Olefin Polymerization Catalysts: Life Beyond Metallocenes", Angew. Chem. Int. Ed., 38, 428–447 (1999).

When using the above catalysts, the catalyst system will generally employ one or more scavenging agents to remove polar impurities from the reaction environment and to increase catalyst activity. Any reaction components, particularly solvent, monomer, and catalyst feedstreams, can inadvertently introduce impurities and adversely affect catalyst activity and stability. Impurities decrease or even eliminate catalytic activity, particularly with ionizing-anion-activated catalyst systems. Polar impurities, or catalyst poisons, include water, oxygen, metal impurities, etc. Usually, these impurities are removed from or reduced in the feedstreams before their addition to the reaction vessel. Impurities can be removed by chemically treating the components or by impurity separation steps. Such treatment or separation can occur during or after synthesis of the components. In any case, the polymerization process will normally employ minor amounts of scavenging agent. Typically, these scavengers will be organometallic such as the Group-13 compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, and isobutyl alumoxane. Those compounds having bulky or $C_6$–$C_{20}$ linear hydrocarbyl substituents connected to the metal or metalloid center are useful because they coordinate to the active catalyst more weakly. Examples include triethylaluminum, but more preferably, bulky compounds such as triisobutylaluminum, triisoprenylaluminum, and long-chain, linear-alkyl-substituted aluminum compounds, such as tri-n-hexylaluminum, tri-n-octylaluminum, or tri-n-dodecylaluminum. When alumoxane is used as activator, any excess over that needed to activate the catalyst can act as a scavenger and additional organometallic scavengers may be unnecessary. Alumoxanes also may be used as scavengers with other activators, e.g., methylalumoxane and triisobutylalumoxane with boron-based activators. The scavenger amount is limited to that amount effective to enhance activity (and with that amount necessary for activation when used in a dual role) since excess amounts may act as catalyst poisons.

This invention's catalyst system can polymerize those unsaturated molecules conventionally recognized as polymerizable using metallocenes. Typical conditions include solution, slurry, gas-phase, and high-pressure polymerization. The catalysts may be supported on inorganic or polymeric supports (including inorganic oxide supports) and as such will be particularly useful in those operating modes employing fixed-bed, moving-bed, fluid-bed, slurry, or solution processes conducted in single, series, or parallel reactors. Invention cocatalysts may also function in catalyst pre-polymerization. WO 98/55518, describes a preferred invention support method for gas-phase or slurry polymerization.

Alternative polymerization embodiments employ the catalyst system in liquid phase (solution, slurry, suspension, bulk phase, or combinations thereof), in high-pressure liquid or supercritical fluid phase, or in gas phase. These processes may also be employed in singular, parallel, or series reactors. The liquid processes comprise contacting olefin molecules with the catalyst system described above in a suitable diluent or solvent and allowing those molecules to react long enough to produce the invention polymers. The term polymer encompasses both homo- and co-polymers. Both aliphatic and aromatic hydrocarbyl solvents are suitable: e.g., hexane. In bulk and slurry processes, the supported catalysts typically contact a liquid monomer slurry. Gas-phase processes use a supported catalyst and use any suitable ethylene polymerization process. Illustrative examples may be found in U.S. Pat. Nos. 4,543,399, 4,588,790, 5,028,670, 5,382, 638, 5352,749, 5,408,017, 5,436,304, 5,453,471, and 5,463, 999, 5,767,208 and WO 95/07942.

The minimum reaction temperature is 40° C., although some embodiments select the minimum temperature to be 60° C. The temperature can go as high as 250° C., but some embodiments use temperatures of up to 220° C. The minimum reaction pressure is 1 mm Hg. But some embodiments choose minimum pressures of 0.1 bar or 1.0 bar. The maximum pressure is less than or equal to 2500 bar. Some embodiments select the maximum pressure to be 1600 other embodiments select the maximum pressure to be 500 bar.

Invention catalysts can produce several linear polyethylene types including high- and ultra-high-molecular-weight polyethylenes, including both homo- and copolymers with other alpha-olefins or alpha-olefinic or non-conjugated diolefins, e.g. $C_3$–$C_{20}$ olefins, diolefins, or cyclic olefins. The polyethylenes are produced by adding ethylene, and optionally one or more other monomers, along with invention activated catalysts that have been slurried with a solvent, such as hexane or toluene, to a low pressure reaction vessel (typically <50 bar). The temperature is usually within the 40–250 ° C. range. Cooling removes polymerization heat. Gas-phase polymerization can be conducted, for example, in a continuous fluid-bed, gas-phase reactor operated at a minimum of 2000 kPa and up to 3000 kPa. The minimum temperature is 60° C.; the maximum temperature is 160° C. The gas-phase reaction uses hydrogen as a reaction modifier at a concentration of no less than 100 PPM. The hydrogen gas concentration should not exceed 200 PPM. The reaction employs a $C_4$–$C_8$ comonomer feedstream and a $C_2$ feedstream. The $C_4$–$C_8$ feedstream goes down to 0.5 mol %. It also may go up to 1.2 mol %. Finally, the $C_2$ feedstream has a minimum concentration of 25 mol %. Its maximum concentration is 35 mol %. See, U.S. Pat. Nos. 4,543,399, 4,588,790, 5,028,670 and 5,405,922 and 5,462,999.

High-molecular-weight, low-crystallinity, ethylene-α-olefin elastomers (including ethylene-cyclic-olefin and ethylene-α-olefin-diolefin elastomers) can be prepared using catalysts activated by invention activators under traditional solution processes or by introducing ethylene into invention catalyst slurries with α-olefin, cyclic olefin, or either or both mixed with other polymerizable and non-polymerizable diluents. Typical ethylene pressures range from 10 to 1000 psig (69–6895 kPa) and the diluent temperature typically remains between 40 and 160° C. The process can occur in one or more stirred tank reactors, operated individually, in series, or in parallel. The general disclosure of U.S. Pat. No. 5,001,205 illustrates general process conditions. See also, international application WO 96/33227 and WO 97/22639.

Besides those specifically described above, other molecules may be polymerized using catalysts precursors activated by invention activators. Some examples of these include styrene, alkyl-substituted styrenes, isobutylene and other geminally disubstituted olefins, ethylidene norbornene, norbornadiene, dicyclopentadiene, and other olefinically unsaturated molecules, including other cyclic olefins, such as cyclopentene, norbornene, alkyl-substituted norbornenes, and vinylic polar, polymerizable molecules. See, for example, U.S. Pat. Nos. 5,635,573, 5,763,556, and WO 99/30822. Additionally, α-olefin macromers of up to 1000 mer units or more may be copolymerized yielding branched olefin polymers. Additionally, activated cation catalysts for oligomerization, dimerization, hydrogenation, olefin/carbon-monoxide copolymerization, hydroformulation, hydrosilation, hydroamination, and related reactions can be activated with invention co-catalysts.

The invention cocatalysts can activate individual catalysts or can activate catalyst mixtures for polymer blends. Adept monomer and catalyst selection yields polymer blends analogous to those using individual catalyst compositions. Polymers having increased MWD (for improved processing) and other benefits available from mixed-catalyst-system polymers can be achieved using invention cocatalysts.

Blended polymer formation can be achieved ex situ through mechanical blending or in situ through using mixed catalyst systems. It is generally believed that in situ blending provides a more homogeneous product and allows the blend to be produced in one step. In-situ blending with mixed catalyst systems involves combining more than one catalyst in the same reactor to simultaneously produce multiple, distinct polymer products. This method requires additional catalyst synthesis, and the various catalyst components must be matched for their activities, the polymer products they generate at specific conditions, and their response to changes in polymerization conditions. Invention cocatalysts can activate mixed catalyst systems.

Exemplary Cocatalysts Embodiments that are Within the Scope of this Invention

Exemplary Boron-based Zwitterionic Cocatalyst Activators

[((methyl (triethylsilyl))) (methyl (triethylsilyl)) ammonium]$^+$--tetrafluoroindenyl--[(perfluorobiphenyl (perfluoroindenyl) (perfluorofluorenyl) borate]$^-$; [((methyl (triethylsilyl))) (methyl) ammonium]$^+$--2,4-difluorophenyl--[(perfluoropyrenyl (perfluoroindenyl) (2,3,5-trifluorophenyl) borate]$^-$; [((methyl (triethylsilyl))) (ethyl) phosphonium]$^+$--perfluorobiphenyl--[(perfluorofluorenyl (perfluorophenyl) (3,4-difluorophenyl) borate]$^-$; [((methyl (triethylsilyl))) (ethyl (triethylsilyl))phosphonium]$^+$--tetrafluoroindenyl--[(perfluorofluorenyl (tetrafluoronaphthyl) (2,4-difluorophenyl) borate]$^-$; [((methyl (triethylsilyl))) (perfluoropropyl) ammonium]$^+$--2,4-difluorophenyl--[(perfluorofluorenyl (perfluorofluorenyl) (pentafluoronaphthyl)borate]$^-$; [((methyl (triethylsilyl))) (ethyl (trimethylsilyl)) ammonium]$^+$--2,3-difluorophenyl--[(perfluoropyrenyl (pentafluoronaphthyl) (perfluorophenyl) borate]$^-$; [((methyl (triethylsilyl))) (isopentyl) ammonium]$^+$--perfluorobiphenyl--[(perfluorophenyl (2,4-difluorophenyl) (3,4-difluorophenyl) borate]$^-$; [((methyl (triethylsilyl))) (isohexyl) ammonium]$^+$--tetrafluoroindenyl--[(perfluorobiphenyl (tetrafluoroindenyl) (perfluoronapthyl) borate]$^-$; [((methyl (triethylsilyl))) (1,6-difluorohexyl) ammonium]$^+$--perfluoroindenyl--[(perfluorophenyl (perfluoronapthyl) (perfluoropyrenyl) borate]$^-$; [((methyl (triethylsilyl))) (methyl (triethylsilyl)) ammonium]$^+$--pentafluorofluorenyl--[(tetrafluoronaphthyl (perfluorobiphenyl) (perfluorofluorenyl) borate]$^-$; [((methyl (triethylsilyl))) (octyl) phosphonium]$^+$--2,3,4-trifluorophenyl--[bis(2,4-difluorophenyl) (2,5-difluorophenyl) borate]$^-$; [(1,2-difluorohexyl) (3-methylpentyl) phosphonium]$^+$--tetrafluoroindenyl--[(tetrafluoronaphthyl (3,4-difluorophenyl) (2,3-difluorophenyl) borate]$^-$; [(1,2-difluorohexyl) (methyl (trimethylsilyl))phosphonium]$^+$--perfluoroindenyl--[(tetrafluoroindenyl (perfluoropyrenyl) (pentafluoronaphthyl) borate]$^-$; [(1,2-difluorohexyl) (methyl (triethylsilyl)) ammonium]⁺--2,5-difluorophenyl--[(2,3-difluorophenyl (perfluoroindenyl) (perfluorofluorenyl) borate]⁻; [(1,2-difluorohexyl) (perfluorobutyl) phosphonium]⁺--2,5-difluorophenyl--[(2,3,4-trifluorophenyl (2,3-difluorophenyl) (tetrafluoroindenyl) borate]⁻; [(1,2-difluorohexyl) (ethyl) arsonium]⁺--2,3,5-trifluorophenyl--[(perfluoroindenyl (perfluorofluorenyl) (2,3,5-trifluorophenyl) borate]⁻; [(1,2-difluorohexyl) (ethyl (trimethylsilyl)) ammonium]⁺--tetrafluoronaphthyl--[bis (perfluorofluorenyl) (tetrafluoroindenyl) borate]⁻; [(1,2-difluorohexyl) (phenyl) ammonium]⁺--perfluoroindenyl--[(perfluorofluorenyl) (perfluoronapthyl) (trifluoroindenyl) borate]⁻; [(1,2-difluorohexyl) (ethyl) ammonium]⁺--perfluoronapthyl--[(perfluorobiphenyl (2,4-difluorophenyl) (perfluorofluorenyl) borate]⁻; [(1,2-difluorohexyl) (perfluoropentyl) ammonium]⁺--perfluoropyrenyl--[(perfluoropyrenyl (2,4-difluorophenyl) (perfluorofluorenyl) borate]⁻; [(1,2-difluorohexyl) (methyl (trimethylsilyl)) ammonium]⁺--perfluoronapthyl--[(perfluoronapthyl (pentafluorofluorenyl) (2,3,4-trifluorophenyl) borate]⁻; [(1,6-difluorohexyl) (perfluorohexyl) arsonium]⁺--perfluorobiphenyl--[(tetrafluoroindenyl (trifluoroindenyl) (perfluorobiphenyl) borate]⁻; [(1,6-difluorohexyl) (perfluoroheptyl)ammonium]⁺--trifluoroindenyl--[bis (pentafluoronaphthyl) (tetrafluoroindenyl) borate]⁻; [(1,6-difluorohexyl) (perfluoroisopropyl) ammonium]⁺--2,3,5-trifluorophenyl--[(tetrafluoronaphthyl (perfluoronapthyl) (2,3,5-trifluorophenyl) borate]⁻; [(1,6-difluorohexyl) (3-methylpentyl) ammonium]⁺--2,3,5-trifluorophenyl--[bis (perfluoroindenyl) (3,4-difluorophenyl) borate]⁻; [(1,6-difluorohexyl) (ethyl (trimethylsilyl)) ammonium]⁺--perfluorofluorenyl--[(perfluorobiphenyl (perfluoroindenyl) (tetrafluoroindenyl) borate]⁻; [(1,6-difluorohexyl) (butyl) ammonium]⁺--perfluorobiphenyl--[bis(tetrafluoronaphthyl) (2,4-difluorophenyl) borate]⁻; [(1,6-difluorohexyl) (perfluoromethyl) ammonium]⁺--2,4-difluorophenyl--[(perfluoroindenyl) (perfluoropyrenyl) (perfluorobiphenyl) borate]⁻; [(1,6-difluorohexyl) (methyl (trimethylsilyl)) phosphonium]⁺--perfluoronapthyl--[(perfluoroindenyl (perfluorobiphenyl) (trifluoroindenyl) borate]⁻; [(1,6-difluorohexyl) (ethyl (trimethylsilyl)) ammonium]⁺--2,3-difluorophenyl--[(pentafluorofluorenyl (2,3,4-trifluorophenyl) (perfluoronapthyl) borate]⁻; [(1,6-difluorohexyl) (1,2-difluorohexyl) ammonium]⁺--pentafluoronapthyl--[(perfluoronapthyl (perfluoropyrenyl) (perfluoropyrenyl) borate]⁻; [(1,6-difluorohexyl) (ethyl (trimethylsilyl)) ammonium]⁺--perfluoronapthyl--[(2,3,4-trifluorophenyl (perfluorobiphenyl) (perfluorofluorenyl) borate]⁻; [(1,6-difluorohexyl) (isohexyl) ammonium]⁺--perfluoroindenyl--[(perfluorobiphenyl (perfluoronapthyl) (perfluoropyrenyl) borate]⁻; [(1,6-difluorohexyl) (ethyl (triethylsilyl)) ammonium]⁺--perfluorofluorenyl--[(perfluorobiphenyl (perfluorophenyl) (perfluoroindenyl) borate]⁻; [(1,6-difluorohexyl) (methyl (trimethylsilyl)) ammonium]⁺--perfluoronapthyl--[(perfluorobiphenyl (perfluorofluorenyl) (perfluoroindenyl) borate]⁻; [(2,3,4,5-tetrafluorophenyl) (hexyl) phosphonium]⁺--2,3-difluorophenyl-[bis(perfluoroindenyl) (2,4-difluorophenyl) borate]⁻; [(2,3,4,5-tetrafluorophenyl) (perfluorophenyl) phosphonium]⁺--tetrafluoronaphthyl--[(perfluorobiphenyl (perfluoroindenyl) (perfluorofluorenyl) borate]⁻; [(2,3,4,5-tetrafluorophenyl) (ethyl (triethylsilyl)) ammonium]⁺--perfluoronapthyl--[(pentafluoronaphthyl (3,4-difluorophenyl) (2,4-difluorophenyl) borate]⁻; [(2,3,4,5-tetrafluorophenyl) (perfluoroethyl) ammonium]⁺--perfluorofluorenyl--[(perfluoronapthyl (perfluorobiphenyl) (2,3,5-trifluorophenyl) borate]⁻; [(2,3,4,5-tetrafluorophenyl) (perfluoro-t-butyl) phosphonium]⁺--perfluorobiphenyl--[(perfluoronapthyl (2,4-difluorophenyl) (perfluorophenyl) borate]⁻; [(2,3,4,5-tetrafluorophenyl) (methyl (trimethylsilyl)) ammonium]⁺--perfluorofluorenyl--[(2,3-difluorophenyl (perfluoroindenyl) (perfluorophenyl) borate]⁻; [(2,3,4,5-tetrafluorophenyl) (propyl) ammonium]⁺--trifluoroindenyl--[(tetrafluoroindenyl (tetrafluoronaphthyl) (perfluoroindenyl) borate]⁻; [(2,3,4,5-tetrafluorophenyl) (1,2-difluorohexyl) phosphonium]⁺--tetrafluoronaphthyl--[(perfluorofluorenyl (perfluoroindenyl) (trifluoroindenyl) borate]⁻; [(2,3,4,5-tetrafluorophenyl) (1,2-difluorohexyl) ammonium]⁺--perfluorophenyl--[bis (perfluorobiphenyl) (2,5-difluorophenyl) borate]⁻; [(2,3,4,5-tetrafluorophenyl) (perfluoropentyl) ammonium]⁺--perfluorophenyl--[(3,4-difluorophenyl (trifluoroindenyl) (perfluoropyrenyl) borate]⁻; [(2,3,4,5-tetrafluorophenyl) (perfluorooctyl) ammonium]⁺--2,3-difluorophenyl--[bis (perfluoroindenyl) (3,4-difluorophenyl) borate]⁻; [(2,3,4,5-tetrafluorophenyl) (perfluoroheptyl) ammonium]⁺--perfluorobiphenyl--[(perfluoroindenyl (2,5-difluorophenyl) (perfluorobiphenyl) borate]⁻; [(2,3,5-trifluorophenyl) (methyl (trimethylsilyl)) ammonium]⁺--perfluorofluorenyl--[bis(perfluoronapthyl) (perfluorobiphenyl) borate]⁻; [(2,3,5-trifluorophenyl) (methyl (triethylsilyl)) ammonium]⁺--trifluoroindenyl--[(tetrafluoroindenyl (2,5-difluorophenyl) (perfluoronapthyl) borate]⁻; [(2,3,5-trifluorophenyl) (perfluorobutyl) ammonium]⁺--perfluoroindenyl--[bis (perfluoronapthyl) (3,4-difluorophenyl) borate]⁻; [(2,3,5-trifluorophenyl) (3-methylpentyl) ammonium]⁺--2,4-difluorophenyl--[(tetrafluoronaphthyl (2,5-difluorophenyl) (perfluoroindenyl) borate]⁻; [(2,3,5-trifluorophenyl) (perfluorooctyl) phosphonium]⁺--perfluorophenyl--[(perfluorobiphenyl (perfluoroindenyl) (perfluoronapthyl) borate]⁻; [(2,3,5-trifluorophenyl) (1,2-difluorohexyl) phosphonium]⁺--3,4-difluorophenyl--[(2,3,5-trifluorophenyl (perfluorobiphenyl) (2,4-difluorophenyl) borate]⁻; [(2,3,5-trifluorophenyl) (ethyl (triethylsilyl)) arsonium]⁺--perfluoropyrenyl--[(2,5-difluorophenyl (perfluorofluorenyl) (tetrafluoroindenyl) borate]⁻; [(2,3,6,7-tetrafluorooctyl) (methyl) phosphonium]⁺--3,4-difluorophenyl--[bis(perfluoronapthyl) (2,5-difluorophenyl) borate]⁻; [(2,3,6,7-tetrafluorooctyl) ((methyl (triethylsilyl))) arsonium]⁺--3,4-difluorophenyl--[(perfluorophenyl (perfluoroindenyl) (perfluoronapthyl) borate]⁻; [(2,3,6,7-tetrafluorooctyl) (perfluoroisopentyl) arsonium]⁺--tetrafluoronaphthyl--[(2,4-difluorophenyl (2,3-difluorophenyl) (perfluorofluorenyl) borate]⁻; [(2,3,6,7-tetrafluorooctyl) (perfluoroisopentyl) arsonium]⁺--perfluorophenyl--[(perfluoronapthyl (perfluorofluorenyl) (tetrafluoroindenyl) borate]⁻; [(2,3,6,7-tetrafluorooctyl) (2,3,4,5-tetrafluorophenyl) phosphonium]⁺--2,4-difluorophenyl--[(2,4-difluorophenyl (perfluorophenyl) (perfluorofluorenyl) borate]⁻; [(2,3,6,7-tetrafluorooctyl) (heptyl) phosphonium]⁺--perfluoroindenyl--[(2,5-difluorophenyl (perfluoronapthyl) (tetrafluoroindenyl) borate]⁻; [(2,3,6,7-tetrafluorooctyl) (isopentyl) ammonium]⁺--perfluorophenyl--[(perfluorofluorenyl (2,4-difluorophenyl) (perfluorophenyl) borate]⁻; [(2,3,6,7-tetrafluorooctyl) (perfluoromethyl) ammonium]⁺--pentafluorofluorenyl--[(perfluoropyrenyl (2,5-difluorophenyl) (perfluoronapthyl) borate]⁻; [(2,3,6,7-tetrafluorooctyl) (perfluoroisopentyl) phosphonium]⁺--2,3-difluorophenyl--[bis(perfluorophenyl) (2,3-difluorophenyl) borate]⁻; [(2,3,6,7-tetrafluorooctyl) (perfluoroisopentyl) ammonium]⁺--perfluorobiphenyl--[(perfluoroindenyl (2,3,4-trifluorophenyl) (perfluorophenyl) borate]⁻; [(2,3,6,7-tetrafluorooctyl) (perfluorobutyl) ammonium]⁺-- perfluorophenyl--[(perfluorofluorenyl (2,5-difluorophenyl) (perfluorobiphenyl) borate]⁻; [(2,3,6,7-tetrafluorooctyl) (1,2-difluorohexyl) ammonium]⁺--trifluoroindenyl--[(2,5-difluorophenyl (2,4-difluorophenyl) (perfluoronapthyl) borate]⁻; [(2,3,6,7-tetrafluorooctyl) (phenyl) phosphonium]⁺--2,3,5-trifluorophenyl--[bis(perfluoronapthyl) (perfluorofluorenyl) borate]⁻; [(2,3,6,7-tetrafluorooctyl) (perfluoroheptyl) ammonium]⁻--tetrafluoronaphthyl--[(perfluoroindenyl (2,3-difluorophenyl) (perfluorofluorenyl) borate]⁻; [(3-methylpentyl) (ethyl (triethylsilyl))arsonium]⁺--perfluorobiphenyl--[(2,3,5-trifluorophenyl (2,3,4-trifluorophenyl) (perfluoroindenyl) borate]⁻; [(3-methylpentyl) (perfluorooctyl) phosphonium]⁺--2,4-difluorophenyl--[bis(perfluorobiphenyl) (2,3-difluorophenyl) borate]⁻; [(3-methylpentyl) (perfluoropropyl) ammonium]⁺--perfluorofluorenyl--[(2,3,5-trifluorophenyl (perfluoronapthyl) (pentafluorofluorenyl) borate]⁻; [(3-methylpentyl) (isohexyl) phosphonium]⁺--perfluoroindenyl--[tris(perfluorofluorenyl) borate]⁻; [(3-methylpentyl) (ethyl (trimethylsilyl))arsonium]⁺--2,3,4-trifluorophenyl--[(perfluoroindenyl (perfluorophenyl) (perfluorofluorenyl) borate]⁻; [(3-methylpentyl) (perfluoropropyl) ammonium]⁺--perfluorobiphenyl--[(perfluorofluorenyl (perfluoroindenyl) (pentafluoronaphthyl) borate]⁻; [(3-methylpentyl) (isopentyl) ammonium]⁺--perfluorofluorenyl--[bis(perfluoronapthyl) (trifluoroindenyl) borate]⁻; [(3-methylpentyl) (1,6-difluorohexyl) phosphonium]⁺--perfluorophenyl--[(pentafluorofluorenyl (perfluorofluorenyl) (perfluorophenyl) borate]⁻; [(3-methylpentyl) (perfluorohexyl) ammonium]⁺--perfluoroindenyl--[(trifluoroindenyl (perfluoronapthyl) (tetrafluoroindenyl) borate]⁻; [(3-methylpentyl) (t-butyl) ammonium]⁺--perfluoroindenyl--[(trifluoroindenyl (tetrafluoroindenyl) (perfluorobiphenyl) borate]⁻; [(3-methylpentyl) (perfluoroheptyl) ammonium]⁺--perfluorofluorenyl--[bis(perfluorophenyl) (perfluoroindenyl) borate]⁻; [(3-methylpentyl) (perfluoropentyl) phosphonium]⁺--2,3,5-trifluorophenyl--[bis(perfluorobiphenyl) (perfluorophenyl) borate]⁻; [(3-methylpentyl) (methyl (trimethylsilyl))phosphonium]⁺--perfluoroindenyl--[(perfluoronapthyl (perfluoropyrenyl) (2,5-difluorophenyl) borate]⁻; [(3-methylpentyl) (perfluoroheptyl) ammonium]⁺--perfluorobiphenyl--[(perfluoronapthyl (pentafluoronaphthyl) (2,3,4-trifluorophenyl) borate]⁻; [(3-methylpentyl) (perfluoromethyl) ammonium]⁺--2,4-difluorophenyl--[(2,3,4-trifluorophenyl (perfluorophenyl) (2,5-difluorophenyl) borate]⁻; [(3-methylpentyl) (isohexyl) ammonium]⁺--perfluorobiphenyl--[(perfluorophenyl (pentafluoronaphthyl) (2,5-difluorophenyl) borate]⁻; [(3-methylpentyl) (hexyl) arsonium]⁺--perfluorofluorenyl--[bis(perfluorobiphenyl) (perfluoroindenyl) borate]⁻; [(3-methylpentyl) (perfluoroethyl) ammonium]⁺--perfluorophenyl--[(pentafluoronaphthyl (perfluorofluorenyl) (perfluorophenyl) borate]⁻; [(butyl) (methyl) phosphonium]⁺--perfluoronapthyl--[(perfluoropyrenyl) (perfluorofluorenyl) (perfluoroindenyl) borate]⁻; [(butyl) (perfluoromethyl) ammonium]⁺--2,4-difluorophenyl--[(trifluoroindenyl) (perfluorofluorenyl) (perfluorobiphenyl) borate]⁻; [(butyl) (perfluorooctyl) ammonium]⁺--trifluoroindenyl--[bis(perfluorophenyl) (perfluoroindenyl) borate]⁻; [(butyl) (perfluoropropyl) ammonium]⁺--3,4-difluorophenyl--[(2,5-difluorophenyl) (perfluoronapthyl) (perfluorobiphenyl) borate]⁻; [(butyl) (2,3,6,7-tetrafluorooctyl) ammonium]⁺--2,3,5-trifluorophenyl--[(pentafluoronaphthyl (pentafluorofluorenyl) (3,4-difluorophenyl) borate]⁻; [(butyl) (perfluoropropyl) ammonium]⁺--perfluoroindenyl--[(perfluorobiphenyl (perfluoronapthyl) (perfluorofluorenyl) borate]⁻; [(butyl) (ethyl (trimethylsilyl)) ammonium]⁺--trifluoroindenyl--[(perfluoroindenyl (perfluorobiphenyl) (trifluoroindenyl) borate]⁻; [(butyl) (isohexyl) phosphonium]⁺--tetrafluoroindenyl--[(2,3,4-trifluorophenyl (perfluorofluorenyl) (perfluorobiphenyl) borate]⁻; [(butyl) (perfluoromethyl) ammonium]⁺--2,3,4-trifluorophenyl--[(2,3,5-trifluorophenyl (2,5-difluorophenyl) (perfluorobiphenyl) borate]⁻; [(butyl) (perfluoromethyl) ammonium]⁺--perfluorophenyl--[(pentafluorofluorenyl (perfluoronapthyl) (perfluorophenyl) borate]⁻; [(butyl) (t-butyl) phosphonium]⁺--perfluorobiphenyl--[(perfluorophenyl (tetrafluoronaphthyl) (perfluorofluorenyl) borate]⁻; [(ethyl) (phenyl) ammonium]⁺--perfluoroindenyl--[(2,5-difluorophenyl (pentafluorofluorenyl) (perfluorophenyl) borate]⁻; [(ethyl) (pentyl) ammonium]⁺--tetrafluoroindenyl--[bis(perfluoroindenyl) (perfluorobiphenyl) borate]⁻; [(ethyl) (1,2-difluorohexyl) phosphonium]⁺--tetrafluoroindenyl--[(2,3,5-trifluorophenyl (2,5-difluorophenyl) (2,3-difluorophenyl) borate]⁻; [(ethyl) (perfluoroisopropyl) arsonium]⁺--perfluorobiphenyl--[(perfluorobiphenyl (tetrafluoronaphthyl) (2,3,4-trifluorophenyl) borate]⁻; [(ethyl) (octyl) ammonium]⁺--2,5-difluorophenyl--[(perfluorobiphenyl (perfluoronapthyl) (perfluorofluorenyl) borate]⁻; [(ethyl) (perfluorophenyl) ammonium]⁺--perfluorofluorenyl--[(perfluoroindenyl (2,3,5-trifluorophenyl) (perfluorobiphenyl) borate]⁻; [(ethyl) (hexyl) ammonium]⁺--2,3,4-trifluorophenyl--[(perfluorobiphenyl (perfluoronapthyl) (perfluoropyrenyl) borate]⁻; (bis(ethyl) ammonium]⁺--pentafluorofluorenyl--[(perfluoronapthyl (3,4-difluorophenyl) (2,3,4-trifluorophenyl) borate]⁻; [(ethyl) (perfluoroisopropyl) ammonium]⁺--pentafluoronaphthyl--[(perfluorofluorenyl (2,5-difluorophenyl) (perfluoronapthyl) borate]⁻; [(ethyl (triethylsilyl)) (methyl (trimethylsilyl))phosphonium]⁺--perfluorobiphenyl--[(perfluorobiphenyl (perfluoronapthyl) (perfluorofluorenyl) borate]⁻; [(ethyl (triethylsilyl)) (methyl) ammonium]⁺--perfluoroindenyl--[bis(trifluoroindenyl) (perfluorobiphenyl) borate]⁻; [(ethyl (triethylsilyl)) (1,6-difluorohexyl) ammonium]⁺--perfluoropyrenyl--[(perfluorobiphenyl (perfluorophenyl) (tetrafluoronaphthyl) borate]⁻; [(ethyl (triethylsilyl)) ((methyl (triethylsilyl))) ammonium]⁺--perfluoroindenyl--[bis(perfluoronapthyl) (pentafluoronaphthyl) borate]⁻; [(ethyl (triethylsilyl)) (methyl (trimethylsilyl)) ammonium]⁺--2,4-difluorophenyl--[(2,4-difluorophenyl (tetrafluoroindenyl) (perfluorobiphenyl) borate]⁻; [(ethyl (triethylsilyl)) (isohexyl) arsonium]⁺--trifluoroindenyl--[(2,3,4-trifluorophenyl (perfluoropyrenyl) (tetrafluoronaphthyl) borate]⁻; [(ethyl (triethylsilyl)) (phenyl) ammonium]⁺--2,3,4-trifluorophenyl--[(2,4-difluorophenyl (perfluoronapthyl) (2,3,5-trifluorophenyl) borate]⁻; [(ethyl (triethylsilyl)) (octyl) ammonium]⁺--pentafluorofluorenyl--[(2,3,5-trifluorophenyl (tetrafluoronaphthyl) (perfluoronapthyl) borate]⁻; [(ethyl (triethylsilyl)) (isohexyl) phosphonium]⁺--perfluorofluorenyl--[(tetrafluoronaphthyl (perfluoroindenyl) (2,3,5-trifluorophenyl) borate]⁻; [(ethyl (triethylsilyl)) (perfluoromethyl) ammonium]⁺--perfluoroindenyl--[(perfluoroindenyl (perfluorophenyl) (perfluorofluorenyl) borate]⁻; [(ethyl (triethylsilyl)) (methyl (triethylsilyl)) ammonium]⁺--2,3,5-trifluorophenyl--[(pentafluoronaphthyl (perfluoroindenyl) (pentafluorofluorenyl) borate]⁻; [(ethyl (triethylsilyl)) (methyl (triethylsilyl)) ammonium]⁺--perfluorophenyl--[(perfluoronapthyl (perfluorophenyl)

(trifluoroindenyl) borate]⁻; (bis(ethyl (triethylsilyl)) ammonium]⁺--trifluoroindenyl--[(perfluorobiphenyl (perfluorophenyl) (2,3-difluorophenyl) borate]⁻; [(ethyl (triethylsilyl)) (2,3,4,5-tetrafluorophenyl) ammonium]⁺--perfluoroindenyl--[bis(perfluoropyrenyl) (tetrafluoroindenyl) borate]⁻; [(ethyl (triethylsilyl)) (perfluoro-t-butyl) ammonium]⁺--perfluoroindenyl--[(perfluoroindenyl (perfluorobiphenyl) (perfluorofluorenyl) borate]⁻; [(ethyl (triethylsilyl)) (3-methylpentyl) phosphonium]⁺--perfluoronapthyl--[(2,4-difluorophenyl (perfluorofluorenyl) (2,3-difluorophenyl) borate]⁻; [(ethyl (triethylsilyl)) (isopropyl) ammonium]⁺--perfluoronapthyl--[(perfluoronapthyl (perfluorofluorenyl) (trifluoroindenyl) borate]⁻; [(ethyl (triethylsilyl)) (perfluoroethyl) arsonium]⁺--perfluoronapthyl--[(tetrafluoronaphthyl (perfluorofluorenyl) (trifluoroindenyl) borate]⁻; [(ethyl (triethylsilyl)) (hexyl) phosphonium]⁺--2,3,4-trifluorophenyl--[(pentafluorofluorenyl (perfluorophenyl) (pentafluoronaphthyl) borate]⁻; [(ethyl (triethylsilyl)) (isopropyl) phosphonium]⁺--2,4-difluorophenyl--[(perfluoropyrenyl (tetrafluoroindenyl) (perfluoronapthyl) borate]⁺; [(ethyl (triethylsilyl)) (perfluoroisopropyl) arsonium]⁺--perfluorofluorenyl--[(2,3,5-trifluorophenyl (pentafluoronaphthyl) (perfluorobiphenyl) borate]⁻; [(ethyl (triethylsilyl)) (ethyl (trimethylsilyl))phosphonium]⁺--perfluorophenyl--[(pentafluoronaphthyl (perfluorofluorenyl) (perfluorobiphenyl) borate]⁻; [(ethyl (triethylsilyl)) (perfluoroethyl) phosphonium]⁺--perfluorofluorenyl--[(perfluorofluorenyl (perfluoropyrenyl) (2,3,5-trifluorophenyl) borate]⁻; [(ethyl (triethylsilyl)) (ethyl (trimethylsilyl)) ammonium]⁺--perfluoronapthyl--[(perfluorofluorenyl (2,3,5-trifluorophenyl) (perfluoronapthyl) borate]⁻; [(ethyl (trimethylsilyl)) (perfluorooctyl) phosphonium]⁺--perfluorobiphenyl--[(perfluorophenyl (perfluoronapthyl) (trifluoroindenyl) borate]⁻; [(ethyl (trimethylsilyl)) (phenyl) ammonium]⁺--2,5-difluorophenyl--[(perfluorophenyl (2,3,5-trifluorophenyl) (pentafluoronaphthyl) borate]⁻; [(ethyl (trimethylsilyl)) (butyl) ammonium]⁺--2,3,5-trifluorophenyl--[(perfluorophenyl (3,4-difluorophenyl) (perfluorobiphenyl) borate]⁻; [(ethyl (trimethylsilyl)) (octyl) arsonium]⁺--2,3-difluorophenyl--[(perfluoroindenyl (perfluorophenyl) (perfluoronapthyl) borate]⁻; [(ethyl (trimethylsilyl)) (methyl (trimethylsilyl)) ammonium]⁺--tetrafluoroindenyl [(perfluorofluorenyl (perfluorobiphenyl) (perfluorophenyl) borate]⁻; [(ethyl (trimethylsilyl)) (perfluorooctyl) phosphonium]⁺--2,3-difluorophenyl--[bis (perfluorofluorenyl) (perfluorobiphenyl) borate]⁻; [(ethyl (trimethylsilyl)) (perfluoroisopentyl) phosphonium]⁺--perfluorofluorenyl--[(tetrafluoronaphthyl (2,5-difluorophenyl) (perfluorofluorenyl) borate]⁻; [(ethyl (trimethylsilyl)) (2,3,5-trifluorophenyl) ammonium]⁺--perfluoroindenyl--[bis(perfluorophenyl) (2,3,5-trifluorophenyl) borate]⁻; [(ethyl (trimethylsilyl)) (perfluoro-t-butyl) ammonium]⁺--pentafluoronaphthyl--[bis (perfluoroindenyl) (perfluorophenyl) borate]⁻; [(ethyl (trimethylsilyl)) (isopropyl) ammonium]⁺--tetrafluoronaphthyl--[(tetrafluoronaphthyl (perfluorofluorenyl) (perfluoroindenyl) borate]⁻; [(ethyl (trimethylsilyl)) (ethyl) ammonium]⁺--perfluoronapthyl--[(perfluorobiphenyl (2,4-difluorophenyl) (perfluorofluorenyl) borate]⁻; [(ethyl (trimethylsilyl)) (perfluoro-t-butyl) ammonium]⁺--perfluoronapthyl--[(3,4-difluorophenyl (perfluorofluorenyl) (pentafluorofluorenyl) borate]⁻; [(ethyl (trimethylsilyl)) (phenyl) phosphonium]⁺--perfluoronapthyl--[(2,3,5-trifluorophenyl (perfluorobiphenyl) (perfluoropyrenyl) borate]⁻; [(ethyl (trimethylsilyl)) (isohexyl) ammonium]⁺--perfluoroindenyl--[bis(perfluorobiphenyl) (perfluorofluorenyl) borate]⁻; (bis(ethyl (trimethylsilyl)) ammonium]⁺--perfluoronapthyl--[bis(perfluorobiphenyl) (2,4-difluorophenyl) borate]⁻; [(ethyl (trimethylsilyl)) (perfluoroisopropyl) ammonium]⁺--3,4-difluorophenyl--[(tetrafluoroindenyl (2,4-difluorophenyl) (2,5-difluorophenyl) borate]⁻; [(ethyl (trimethylsilyl)) (methyl (triethylsilyl))arsonium]⁺--perfluorophenyl--[(pentafluorofluorenyl (pentafluoronaphthyl) (perfluorofluorenyl) borate]⁻; [(heptyl) (perfluorophenyl) ammonium]⁺--perfluorobiphenyl--[bis(2,3,4-trifluorophenyl) (perfluorofluorenyl) borate]⁻; [(heptyl) (perfluoropropyl) ammonium]⁺--trifluoroindenyl--[(tetrafluoroindenyl (perfluorophenyl) (2,3,4-trifluorophenyl) borate]⁻; [(heptyl) (phenyl) phosphonium]⁺--perfluorofluorenyl--[(perfluorophenyl (perfluorofluorenyl) (perfluoropyrenyl) borate]⁻; [(heptyl) (perfluorophenyl) phosphonium]⁺--perfluoronapthyl--[(perfluorophenyl (perfluoronapthyl) (perfluorobiphenyl) borate]⁻; [(heptyl) (propyl) phosphonium]⁺--perfluoronapthyl--[(2,3,4-trifluorophenyl (3,4-difluorophenyl) (pentafluorofluorenyl) borate]⁻; [(heptyl) (methyl (triethylsilyl)) ammonium]⁺--perfluorobiphenyl--[(perfluoronapthyl (pentafluorofluorenyl) (perfluorobiphenyl) borate]⁻; [(heptyl) (3-methylpentyl) ammonium]⁺--tetrafluoronaphthyl--[(perfluoronapthyl (pentafluoronaphthyl) (perfluorofluorenyl) borate]⁻; [(heptyl) (perfluorohexyl) ammonium]⁺--perfluoronapthyl--[(perfluoronapthyl (trifluoroindenyl) (perfluoroindenyl) borate]⁻; [(heptyl) (perfluorohexyl) ammonium]⁺--pentafluorofluorenyl--[bis(perfluorophenyl) (2,3,4-trifluorophenyl) borate]⁻; [(heptyl) (octyl) phosphonium]⁺--perfluoroindenyl--[(perfluoroindenyl (2,3,5-trifluorophenyl) (perfluorofluorenyl) borate]⁻; [(hexyl) (perfluoroisopropyl) ammonium]⁺--perfluorofluorenyl--[(2,4-difluorophenyl (pentafluoronaphthyl) (perfluorofluorenyl) borate]⁻; [(hexyl) (octyl) ammonium]⁺--2,3,4-trifluorophenyl--[bis (perfluorophenyl) (2,5-difluorophenyl) borate]⁻; [(hexyl) (isopentyl) ammonium]⁺--perfluorophenyl--[bis (pentafluoronaphthyl) (2,3,4-trifluorophenyl) borate]⁻; [(hexyl) (perfluorophenyl) ammonium]⁺--perfluoronapthyl--[(perfluoronapthyl (perfluoroindenyl) (perfluorobiphenyl) borate]⁻; [(hexyl) (perfluoroheptyl) ammonium]⁺--trifluoroindenyl--[(perfluorophenyl (perfluorobiphenyl) (perfluoropyrenyl) borate]⁻; [(hexyl) (2,3,6,7-tetrafluorooctyl) ammonium]⁺--perfluoroindenyl--[(pentafluorofluorenyl (trifluoroindenyl) (2,4-difluorophenyl) borate]⁻; [(hexyl) (isopentyl) ammonium]⁺--perluorophenyl--[(3,4-difluorophenyl (perfluorobiphenyl) (perfluorophenyl) borate]⁻; [(isohexyl) (perfluorophenyl) phosphonium]⁺--perfluorofluorenyl--[(perfluorofluorenyl (perfluoronapthyl) (perfluorophenyl) borate]⁻; [(isohexyl) (1,6-difluorohexyl) arsonium]⁺--perfluoropyrenyl--[(perfluorofluorenyl (perfluorophenyl) (perfluoroindenyl) borate]⁻; [(isohexyl) (3-methylpentyl) ammonium]⁺--perfluorofluorenyl--[(perfluorofluorenyl (perfluoronapthyl) (tetrafluoronaphthyl) borate]⁻; [(isohexyl) (ethyl) ammonium]⁺--perfluoroindenyl--[(perfluorophenyl (2,3,4-trifluorophenyl) (perfluorofluorenyl) borate]⁻; [(isohexyl) (perfluorobutyl) phosphonium]⁺--perfluorobiphenyl--[(2,5-difluorophenyl (pentafluoronaphthyl) (2,3-difluorophenyl) borate]⁻; [(isohexyl) (2,3,4,5-tetrafluorophenyl) ammonium]⁺--perfluorofluorenyl--[bis(perfluoronapthyl) (perfluorophenyl) borate]⁻; [(isohexyl) (methyl (trimethylsilyl))arsonium]⁺--perfluorobiphenyl--

[(tetrafluoronapthyl (perfluorophenyl) (perfluoropyrenyl) borate]⁻; [(isohexyl) (perfluoro-t-butyl) ammonium]⁺--pentafluorofluorenyl--[bis(perfluorobiphenyl) (2,5-difluorophenyl) borate]⁻; [(isohexyl) (perfluoroethyl) ammonium]⁺--2,5-difluorophenyl--[(tetrafluoroindenyl (2,3,5-trifluorophenyl) (perfluorobiphenyl) borate]⁻; (bis (isohexyl) ammonium]⁺--trifluoroindenyl--[bis (perfluorofluorenyl) (perfluoronapthyl) borate]⁻; (bis (isohexyl) phosphonium]⁺--perfluoroindenyl--[(perfluorobiphenyl (2,3-difluorophenyl) (perfluoroindenyl) borate]⁻; [(isohexyl) (3-methylpentyl) ammonium]⁺--perfluorofluorenyl--[(tetrafluoronaphthyl (perfluorofluorenyl) (perfluorophenyl) borate]⁻; [(isohexyl) (perfluoro-t-butyl) ammonium]⁺--perfluoroindenyl--[(trifluoroindenyl) (perfluorophenyl) (pentafluorofluorenyl) borate]⁻; [(isohexyl) (butyl) ammonium]⁺--perfluoroindenyl--[(perfluorophenyl (trifluoroindenyl) (2,3-difluorophenyl) borate]⁻; [(isohexyl) (perfluorohexyl) ammonium]⁺--tetrafluoroindenyl--[bis(perfluoroindenyl) (2,5-difluorophenyl) borate]⁻; [(isohexyl) (3-methylpentyl) arsonium]⁺--2,3,5-trifluorophenyl--[(perfluoropyrenyl (perfluorophenyl) (perfluoroindenyl) borate]⁻; [(isohexyl) (1,2-difluorohexyl) phosphonium]⁺--perfluoroindenyl--[(perfluoronapthyl (perfluoropyrenyl) (2,3,4-trifluorophenyl) borate]⁻; [(isohexyl) (2,3,6,7-tetrafluorooctyl) phosphonium]⁺--perfluoronapthyl--[(perfluorobiphenyl (2,3-difluorophenyl) (perfluoronapthyl) borate]⁻; [(isohexyl) (perfluoroethyl) ammonium]⁺--trifluoroindenyl--[(perfluorophenyl (tetrafluoronaphthyl) (2,3-difluorophenyl) borate]⁻; [(isohexyl) (methyl (trimethylsilyl)) ammonium]⁺--tetrafluoronaphthyl--[bis (perfluoronapthyl) (perfluorofluorenyl) borate]⁻; [(isopentyl) (perfluoromethyl) arsonium]⁺--tetrafluoronaphthyl--[(perfluoronapthyl (trifluoroindenyl) (2,3,5-trifluorophenyl) borate]⁻; [(isopentyl) (perfluoropropyl) ammonium]⁺--2,3,4-trifluorophenyl--[(perfluorofluorenyl (perfluorophenyl) (perfluoronapthyl) borate]⁻; [(isopentyl) (methyl (trimethylsilyl)) ammonium]⁺--perfluoronapthyl--[bis(3,4-difluorophenyl) (perfluorofluorenyl) borate]⁻; [(isopentyl) (butyl) ammonium]⁺--perfluoroindenyl--[(tetrafluoroindenyl (perfluoronapthyl) (perfluorofluorenyl) borate]⁻; (bis (isopentyl) ammonium]⁺--perfluoronapthyl--[(perfluoropyrenyl (perfluorobiphenyl) (perfluorophenyl) borate]⁻; [(isopentyl) (1,6-difluorohexyl) ammonium]⁺--2,3,4-trifluorophenyl--[bis(perfluorophenyl) (perfluorofluorenyl) borate]⁻; [(isopentyl) (perfluoroheptyl) phosphonium]⁺--perfluorophenyl--[(pentafluoronaphthyl (2,4-difluorophenyl) (perfluorophenyl) borate]⁻; [(isopentyl) (perfluoropropyl) ammonium]⁺--perfluoronapthyl--[(perfluoroindenyl (pentafluoronaphthyl) (tetrafluoroindenyl) borate]⁻; [(isopropyl) (1,2-difluorohexyl) phosphonium]⁺--2,3,5-trifluorophenyl--[(2,3-difluorophenyl (perfluorobiphenyl) (perfluorofluorenyl) borate]⁻; [(isopropyl) (heptyl) ammonium]⁺--2,3,4-trifluorophenyl--[(2,3,4-trifluorophenyl (perfluorofluorenyl) (2,4-difluorophenyl) borate]⁻; [(isopropyl) (3-methylpentyl) ammonium]⁺--perfluoronapthyl--[(pentafluorofluorenyl (perfluorobiphenyl) (2,5-difluorophenyl) borate]⁻; [(isopropyl) (propyl) ammonium]⁺--2,3,5-trifluorophenyl--[(2,5-difluorophenyl (pentafluorofluorenyl) (perfluorofluorenyl) borate]⁻; [(isopropyl) (perfluorohexyl) phosphonium]⁺--perfluorobiphenyl--[(perfluoroindenyl) (perfluorofluorenyl) (perfluoropyrenyl) borate]⁻; [(methyl) (perfluoropentyl) phosphonium]⁺--pentafluoronaphthyl--[bis(perfluorophenyl) (tetrafluoroindenyl) borate]⁻; [(methyl) (phenyl) phosphonium]⁺--perfluoroindenyl--[(perfluoronapthyl (2,3-difluorophenyl) (3,4-difluorophenyl) borate]⁻; [(methyl) (1,2-difluorohexyl) phosphonium]⁺--2,3-difluorophenyl--[(perfluoroindenyl (perfluorophenyl) (perfluorobiphenyl) borate]⁻; [(methyl) (heptyl) ammonium]⁺--perfluoropyrenyl--[(perfluoroindenyl (trifluoroindenyl) (perfluorophenyl) borate]⁻; [(methyl) (isopropyl) phosphonium]⁺-perfluorofluorenyl--[(2,5-difluorophenyl (perfluoroindenyl) (3,4-difluorophenyl) borate]⁻; [(methyl) (methyl (triethylsilyl)) ammonium]⁺--perfluoropyrenyl--[bis (perfluorophenyl) (tetrafluoroindenyl) borate]⁻; [(methyl) (methyl (trimethylsilyl)) ammonium]⁺--3,4-difluorophenyl-[(2,5-difluorophenyl (perfluorobiphenyl) (trifluoroindenyl) borate]⁻; [(methyl) (heptyl) ammonium]⁺--perfluorophenyl--[(perfluorophenyl (2,3,5-trifluorophenyl) (perfluorofluorenyl) borate]⁻; [(methyl) (perfluoroisopropyl) ammonium]⁺--perfluoroindenyl--[(perfluoronapthyl (2,3,5-trifluorophenyl) (trifluoroindenyl) borate]⁻; [(methyl) (ethyl (triethylsilyl)) ammonium]⁺--perfluoronapthyl--[bis (perfluoronapthyl) (perfluorophenyl) borate]⁻; [(methyl) (t-butyl) ammonium]⁺--perfluoroindenyl--[(perfluorophenyl (perfluorofluorenyl) (tetrafluoroindenyl) borate]⁻; [(methyl) (propyl) ammonium]⁺--perfluorofluorenyl--[(pentafluorofluorenyl (pentafluoronaphthyl) (perfluorobiphenyl) borate]⁻; [(methyl) (pentyl) ammonium]⁺--2,3-difluorophenyl--[(perfluoronapthyl (perfluorofluorenyl) (2,4-difluorophenyl) borate]⁻; [(methyl (triethylsilyl)) (perfluoroheptyl) ammonium]⁺--perfluorophenyl--[(perfluorofluorenyl (pentafluorofluorenyl) (perfluoroindenyl) borate]⁻; [(methyl) (triethylsilyl)) (perluorobutyl) ammonium]⁺--pentafluoronaphthyl--[(perfluoronapthyl (perfluorobiphenyl) (trifluoroindenyl) borate]⁻; [(methyl) (triethylsilyl)) (pernluoropentyl) ammonium]⁺--2,3,5-trifluorophenyl--[(perfluorophenyl (perfluorofluorenyl) (perfluoroindenyl) borate]⁻; [(methyl (triethylsilyl)) (2,3,5-trifluorophenyl) phosphonium]⁺--perfluoronapthyl--[(perfluoronapthyl (perfluoroindenyl) (perfluorophenyl) borate]⁻; [(methyl (triethylsilyl)) (ethyl (triethylsilyl)) phosphonium]⁺--perfluoroindenyl--[(2,3,4-trifluorophenyl (2,3-difluorophenyl) (perfluoronapthyl) borate]⁻; [(methyl (triethylsilyl)) (perfluoromethyl) ammonium]⁺--2,5-difluorophenyl--[(perfluoronapthyl (perfluorobiphenyl) (2,3,4-trifluorophenyl) borate]⁻; [(methyl (triethylsilyl)) (perfluorooctyl) ammonium]⁺--perfluoroindenyl--[tris (perluoronapthyl) borate]⁻; [(methyl (triethylsilyl)) (pentyl) ammonium]⁺--perfluorofluorenyl--[bis(perfluorophenyl) (tetrafluoronaphthyl) borate]⁻; [(methyl (triethylsilyl)) (perfluorooctyl) ammonium]⁺--perfluoronapthyl--[(perfluoroindenyl (perfluorofluorenyl) (perfluorobiphenyl) borate]⁻; [(methyl (triethylsilyl)) (phenyl) ammonium]⁺--perfluoronapthyl--[bis(trifluoroindenyl) (2,4-difluorophenyl) borate]⁻; [(methyl (trimethylsilyl)) (isopropyl) ammonium]⁺--perfluoroindenyl--[(trifluoroindenyl (2,4-difluorophenyl) (perfluorophenyl) borate]⁻; [(methyl (trimethylsilyl)) (perfluorohexyl) ammonium]⁺--perfluorofluorenyl--[(perfluorofluorenyl (2,3-difluorophenyl) (perfluoronapthyl) borate]⁻; [(methyl (trimethylsilyl)) (pernuoroheptyl) ammonium]⁺--perluorophenyl--[(perfluoropyrenyl (tetrafluoronaphthyl) (perfluoronapthyl) borate]⁻; [(methyl (trimethylsilyl)) (2,3,6,7-tetrafluorooctyl) ammonium]⁺--perfluoroindenyl--[(2,3-difluorophenyl (3,4-difluorophenyl) (2,3,4-trifluorophenyl) borate]⁻; [(methyl (trimethylsilyl)) ((methyl (triethylsilyl))) ammonium]⁺--2,3-difluorophenyl--[(perluorophenyl (perfluorobiphenyl) (2,3,4-trifluorophenyl) borate]⁻; [(methyl (trimethylsilyl)) (pentyl) ammonium]⁺-- perluoronapthyl--[(perfluorobiphenyl (perfluorofluorenyl) (tetrafluoronaphthyl) borate]⁻; [(methyl (trimethylsilyl)) (perfluorobutyl) phosphonium]⁺--perfluoronapthyl--[(perfluorofluorenyl (perfluoroindenyl) (2,3-difluorophenyl) borate]⁻; [(methyl (trimethylsilyl)) (perfluoromethyl) ammonium]$^{+-3,4}$-difluorophenyl--[(perfluorophenyl (perfluoroindenyl) (perluoronapthyl) borate]⁻; [(methyl (trimethylsilyl)) (perfluoroethyl) ammonium]⁺--perfluoroindenyl--[(2,3,4-trifluorophenyl (pentafluoronaphthyl) (perfluoronapthyl) borate]⁻; [(methyl (trimethylsilyl)) (2,3,5-trifluorophenyl) ammonium]⁺--2,3,4-trifluorophenyl--[(perfluoroindenyl (perluorophenyl) (perfluorobiphenyl) borate]⁻; [(methyl (trimethylsilyl)) (perfluorobutyl) ammonium]⁺--pentafluorofluorenyl--[(perfluorophenyl (2,3-difluorophenyl) (perfluoropyrenyl) borate]⁻; [(methyl (trimethylsilyl)) (pentyl) ammonium]⁺--perfluorobiphenyl--[(3,4-difluorophenyl (perfluoropyrenyl) (pentafluorofluorenyl) borate]⁻; [(methyl (trimethylsilyl)) (3-methylpentyl) ammonium]⁺--perfluorofluorenyl--[(perfluorobiphenyl (perfluorofluorenyl) (pentafluoronaphthyl) borate]⁻; [(methyl (trimethylsilyl)) (pentyl) ammonium]⁺--perfluorobiphenyl--[bis(perfluorofluorenyl) (perfluorobiphenyl) borate]⁻; [(methyl (trimethylsilyl)) (butyl) ammonium]⁺--perfluorobiphenyl--[bis(perfluorofluorenyl) (perfluoronapthyl) borate]⁻; [(octyl) (heptyl) ammonium]⁺--perfluorofluorenyl--[(pentafluoronaphthyl (3,4-difluorophenyl) (tetrafluoroindenyl) borate]⁻; [(octyl) (3-methylpentyl) ammonium]⁺--2,5-difluorophenyl--[(perfluoroindenyl (perfluorofluorenyl) (trifluoroindenyl) borate]⁻; [(octyl) (methyl (trimethylsilyl)) ammonium]⁺--perfluorobiphenyl--[bis(perfluorofluorenyl) (perfluorophenyl) borate]⁻; [(octyl) (1,6-difluorohexyl) phosphonium]⁻--tetrafluoronaphthyl--[(2,3,4-trifluorophenyl (2,3-difluorophenyl) (perfluorophenyl) borate]⁻; [(octyl) (ethyl (triethylsilyl)) ammonium]⁺--perfluorobiphenyl--[(pentafluoronaphthyl (pentafluorofluorenyl) (perfluorophenyl) borate]⁻; [(octyl) (ethyl (triethylsilyl)) ammonium]⁻--perfluorofluorenyl--[(trifluoroindenyl (perfluoronapthyl) (perfluorophenyl) borate]⁻; [(octyl) (perfluorooctyl) ammonium]⁺--2,3,5-trifluorophenyl--[(perfluorophenyl (2,4-difluorophenyl) (2,3,4-trifluorophenyl) borate]⁻; [(octyl) (perfluoropentyl) ammonium]⁺--perfluoronapthyl--[(perfluorofluorenyl (perfluorobiphenyl) (perfluoronapthyl) borate]⁻; [(octyl) (ethyl (triethylsilyl)) ammonium]⁺--2,3,4-trifluorophenyl--[(tetrafluoronaphthyl (perfluorophenyl) (perfluoropyrenyl) borate]⁻; [(octyl) (2,3,5-trifluorophenyl) ammonium]⁺--tetrafluoronaphthyl--[(perfluoronapthyl (perfluoroindenyl) (perfluorobiphenyl) borate]⁻; [(octyl) (perfluoropropyl) ammonium]⁺--perfluorophenyl--[(perfluoronapthyl (2,3,4-trifluorophenyl) (2,3,5-trifluorophenyl) borate]⁻; [(pentyl) (ethyl (triethylsilyl)) ammonium]⁺--perfluorobiphenyl--[bis(perfluorobiphenyl) (2,4-difluorophenyl) borate]⁻; [(pentyl) (methyl (triethylsilyl)) ammonium]⁺--tetrafluoronaphthyl--[(3,4-difluorophenyl (perfluoronapthyl) (tetrafluoroindenyl) borate]⁻; [(pentyl) (perfluoropentyl) phosphonium]⁺--2,4-difluorophenyl--[(perfluorophenyl (perfluorofluorenyl) (trifluoroindenyl) borate]⁻; [(pentyl) (isopropyl) phosphonium]⁺--perfluorobiphenyl--[bis(pentafluorofluorenyl) (perfluorofluorenyl) borate]⁻; [(pentyl) (2,3,5-trifluorophenyl) ammonium]⁺--perfluorophenyl--[(pentafluoronaphthyl (perfluorobiphenyl) (perfluorophenyl) borate]⁻; [(pentyl) (ethyl (trimethylsilyl)) ammonium]⁺--3,4-difluorophenyl--[(perfluoroindenyl (perfluorophenyl) (perfluoronapthyl) borate]⁻; [(pentyl) (1,2-difluorohexyl) ammonium]⁺--perfluorofluorenyl--[(perfluorobiphenyl (perfluoroindenyl) (perfluoronapthyl) borate]⁻; [(pentyl) (ethyl (triethylsilyl)) ammonium]⁺--perfluorobiphenyl--[(perfluorofluorenyl (perfluorobiphenyl) (2,3-difluorophenyl) borate]⁻; [(pentyl) ((methyl (triethylsilyl))) ammonium]⁺--perfluorobiphenyl--[(perfluorofluorenyl (perfluorophenyl) (perfluoropyrenyl) borate]⁻; [(pentyl) (ethyl (triethylsilyl)) ammonium]⁺--perfluorobiphenyl--[(2,3-difluorophenyl (pentafluorofluorenyl) (perfluoroindenyl) borate]⁻; [(pentyl) (perfluoroethyl) ammonium]⁺--perfluorophenyl--[(perfluoroindenyl (perfluorophenyl) (perfluorofluorenyl) borate]⁻; (bis(perfluorobutyl) ammonium]$^{+-3,4}$-difluorophenyl--[(trifluoroindenyl (perfluorobiphenyl) (perfluoroindenyl) borate]⁻; [(perfluorobutyl) (perfluoropentyl) ammonium]⁺--trifluoroindenyl--[(perfluoroindenyl (tetrafluoroindenyl) (perfluorophenyl) borate]⁻; [(perfluorobutyl) (perfluoroisopentyl) ammonium]⁺--pentafluoronaphthyl--[(perfluoroindenyl (perfluoronapthyl) (2,3,4-trifluorophenyl) borate]⁻; [(perfluorobutyl) (octyl) ammonium]⁺--perfluorofluorenyl--[(perfluoropyrenyl (trifluoroindenyl) (perfluorobiphenyl) borate]⁻; [(perfluorobutyl) (methyl) ammonium]⁺--perfluorofluorenyl--[bis(perfluoroindenyl) (trifluoroindenyl) borate]⁻; [(perfluoroethyl) (perfluoro-t-butyl) ammonium]⁺--trifluoroindenyl--[(pentafluorofluorenyl (trifluoroindenyl) (perfluorobiphenyl) borate]⁻; [(perfluoroethyl) (perfluoropropyl) ammonium]⁺--tetrafluoronaphthyl--[(3,4-difluorophenyl (perfluorobiphenyl) (2,5-difluorophenyl) borate]⁻; [(perfluoroethyl) (perfluoroisopropyl) ammonium]⁺--perfluorofluorenyl--[(perfluoroindenyl (trifluoroindenyl) (tetrafluoroindenyl) borate]⁻; [(perfluoroethyl) (isohexyl) ammonium]⁺--3,4-difluorophenyl--[(tetrafluoronaphthyl (2,4-difluorophenyl) (perfluorobiphenyl) borate]⁻; (bis(perfluoroethyl) arsonium]⁺--perfluoropyrenyl--[bis(trifluoroindenyl) (perfluorophenyl) borate]⁻; [(perfluoroheptyl) (ethyl (triethylsilyl)) ammonium]⁺--perfluoronapthyl--[(perfluoroindenyl (perfluoronapthyl) (perfluorophenyl) borate]⁻; (bis(perfluoroheptyl) ammonium]⁺--2,4-difluorophenyl--[(perfluoronapthyl (pentafluoronaphthyl) (perfluorobiphenyl) borate]⁻; [(perfluoroheptyl) (perfluorobutyl) ammonium]⁻--perfluorophenyl--[(2,3-difluorophenyl (tetrafluoroindenyl) (perfluorofluorenyl) borate]⁻; [(perfluoroheptyl) (methyl (triethylsilyl)) ammonium]⁺--pentafluorofluorenyl--[(perfluorobiphenyl (perfluoronapthyl) (2,5-difluorophenyl) borate]⁻; [(perfluoroheptyl) (heptyl) ammonium]⁺--perfluorobiphenyl--[bis(pentafluorofluorenyl) (tetrafluoronaphthyl) borate]⁻; [(perfluoroheptyl) (ethyl (trimethylsilyl)) ammonium]⁺--perfluoropyrenyl--[(perfluoroindenyl (perfluoronapthyl) (perfluorophenyl) borate]⁻; [(perfluoroheptyl) (octyl) arsonium]⁺--perfluoroindenyl--[(perfluoroindenyl (perfluorobiphenyl) (2,4-difluorophenyl) borate]⁻; [(perfluoroheptyl) (perfluoroisopentyl) arsonium]⁻--perfluorofluorenyl--[(perfluorofluorenyl (perfluoronapthyl) (3,4-difluorophenyl) borate]⁻; [(perfluoroheptyl) (isopentyl) ammonium]⁺--perfluorophenyl--[(perfluorofluorenyl (2,3,4-trifluorophenyl) (perfluorophenyl) borate]⁻; [(perfluoroheptyl) (2,3,4,5-tetrafluorophenyl) ammonium]⁺--pentafluorofluorenyl--[bis(perfluorobiphenyl) (2,5-difluorophenyl) borate]⁻; [(perfluorohexyl) (3-methylpentyl) ammonium]⁺--2,4-difluorophenyl--[(2,3,4-trifluorophenyl (pentafluoronaphthyl) (perfluorofluorenyl) borate]⁻; [(perfluorohexyl) (2,3,5-trifluorophenyl) phosphonium]⁺--perfluoroindenyl--[(perfluoropyrenyl (2,5-difluorophenyl) (trifluoroindenyl) borate]⁻; [(perfluorohexyl) (heptyl)

ammonium]⁺--perfluorobiphenyl--[(2,3,5-trifluorophenyl (2,5-difluorophenyl) (perfluorobiphenyl) borate]⁻; [(perfluorohexyl) (hexyl) ammonium]⁺--perfluoropyrenyl--[(2,3-difluorophenyl (perfluorofluorenyl) (pentafluoronaphthyl) borate]⁻; [(perfluorohexyl) (methyl (trimethylsilyl)) ammonium]⁺--perfluorophenyl--[bis(2,3-difluorophenyl) (2,5-difluorophenyl) borate]⁻; [(perfluorohexyl) (perfluorophenyl) ammonium]⁺--perfluorophenyl--[(tetrafluoronaphthyl (perfluoronapthyl) (perfluoroindenyl) borate]⁻; [(perfluorohexyl) (perfluoromethyl) phosphonium]⁺--perfluorofluorenyl--[bis(perluorophenyl) (tetrafluoroindenyl) borate]⁻; [(perfluoroisopentyl) (1,6-difluorohexyl) ammonium]⁺--perfluoroindenyl--[(pentafluoronaphthyl (perfluoroindenyl) (2,3-difluorophenyl) borate]⁻; [(perfluoroisopentyl) (methyl (trimethylsilyl))phosphonium]⁺--perfluorophenyl--[bis(perfluorofluorenyl) (perfluorobiphenyl) borate]⁻; [(perfluoroisopentyl) (methyl (triethylsilyl)) arsonium]⁺--perfluorobiphenyl--[(perfluoroindenyl (perfluorophenyl) (2,3,5-trifluorophenyl) borate]⁻; [(perfluoroisopentyl) (methyl) ammonium]⁺--perfluoroindenyl--[(perfluorobiphenyl (perfluoronapthyl) (3,4-difluorophenyl) borate]⁻; [(perfluoroisopentyl) (1,2-difluorohexyl) phosphonium]⁺--2,3,5-trifluorophenyl--[bis(perfluoronapthyl) (perfluorobiphenyl) borate]⁻; [(perfluoroisopentyl) (perfluorophenyl) ammonium]⁺--perfluorofluorenyl--[(perfluoroindenyl (pentafluoronaphthyl) (perfluoronapthyl) borate]⁻; (bis(perfluoroisopentyl) ammonium]⁺--pentafluoronaphthyl--[bis(perfluoronapthyl) (perfluoroindenyl) borate]⁻; [(perfluoroisopentyl) (octyl) ammonium]⁺--perfluoronapthyl--[bis(perfluorofluorenyl) (perfluorobiphenyl) borate]⁻; [(perfluoroisopentyl) (propyl) ammonium]⁺--tetrafluoroindenyl--[(3,4-difluorophenyl) (perfluorobiphenyl) (perfluorofluorenyl) borate]⁻; [(perfluoroisopropyl) (perfluoroheptyl) phosphonium]⁺--tetrafluoroindenyl--[(perfluorobiphenyl (perfluoronapthyl) (2,5-difluorophenyl) borate]⁻; [(perfluoroisopropyl) (butyl) ammonium]⁺--2,4-difluorophenyl--[bis(perfluorophenyl) (trifluoroindenyl) borate]⁻; [(perfluoroisopropyl) (isohexyl) ammonium]⁺--perfluorofluorenyl--[(3,4-difluorophenyl (perfluoroindenyl) (perfluoropyrenyl) borate]⁻; [(perfluoroisopropyl) (isopropyl) ammonium]⁺--perfluorofluorenyl--[bis(perfluorophenyl) (2,3,4-trifluorophenyl) borate]⁻; [(perfluoroisopropyl) (perfluorobutyl) phosphonium]⁺--3,4-difluorophenyl--[(perfluoroindenyl (perfluoronapthyl) (2,3-difluorophenyl) borate]⁻; [(perfluoroisopropyl) (perfluorophenyl) ammonium]⁺--2,5-difluorophenyl--[(perfluorophenyl (pentafluoronaphthyl) (2,3,5-trifluorophenyl) borate]⁻; (bis(perfluoroisopropyl) phosphonium]⁺--perfluoronapthyl--[(pentafluoronaphthyl (2,5-difluorophenyl) (3,4-difluorophenyl) borate]⁻; [(perfluoroisopropyl) (hexyl) phosphonium]⁺--pentafluoronaphthyl--[(perfluorofluorenyl (perfluoroindenyl) (tetrafluoronaphthyl) borate]⁻; [(perfluoromethyl) (methyl (trimethylsilyl)) phosphonium]⁺--perfluoroindenyl--[(perfluorophenyl (perfluoropyrenyl) (perfluoronapthyl) borate]⁻; [(perfluoromethyl) (isopropyl) ammonium]⁺--2,3,4-trifluorophenyl--[(trifluoroindenyl (perfluorofluorenyl) (tetrafluoronaphthyl) borate]⁻; [(perfluoromethyl) (perfluorophenyl) phosphonium]⁺--2,3,5-trifluorophenyl--[(perfluorobiphenyl (perfluoronapthyl) (pentafluoronaphthyl) borate]⁻; [(perfluoromethyl) (3-methylpentyl) ammonium]⁺--perfluoronapthyl--[bis(perfluorofluorenyl) (perfluoronapthyl) borate]⁻; [(perfluoromethyl) (phenyl) phosphonium]⁺--perfluorophenyl--[(tetrafluoronaphthyl (perfluoroindenyl) (2,5-difluorophenyl) borate]⁻; [(perfluoromethyl) (isopentyl) ammonium]⁺--perfluorophenyl--[(perfluorofluorenyl (perfluorobiphenyl) (tetrafluoroindenyl) borate]⁻; [(perfluoromethyl) (hexyl) ammonium]⁺--pentafluoronaphthyl--[(perfluorobiphenyl (2,5-difluorophenyl) (tetrafluoroindenyl) borate]⁻; [(perfluoromethyl) (2,3,5-trifluorophenyl) ammonium]⁺--perluorophenyl--[(perfluorobiphenyl (perfluoropyrenyl) (perfluorofluorenyl) borate]⁻; [(perfluoromethyl) (isopentyl) phosphonium]⁺--perfluoroindenyl--[(tetrafluoroindenyl (perfluoronapthyl) (3,4-difluorophenyl) borate]⁻; [(perfluorooctyl) (perfluorophenyl) ammonium]⁺--2,3,4-trifluorophenyl--[bis(perfluorophenyl) (tetrafluoronaphthyl) borate]⁻; [(perfluorooctyl) (1,2-difluorohexyl) ammonium]⁺--2,3,4-trifluorophenyl--[(perfluoropyrenyl (perfluorofluorenyl) (tetrafluoroindenyl) borate]⁻; [(perfluorooctyl) (perfluoromethyl) phosphonium]⁺--perfluorobiphenyl--[bis(perfluorophenyl) (perfluorofluorenyl) borate]⁻; (bis(perfluorooctyl) ammonium]⁺--pentafluorofluorenyl--[bis(perfluoroindenyl) (perfluorophenyl) borate]⁻; [(perfluorooctyl) (ethyl (trimethylsilyl)) ammonium]⁺--perfluoroindenyl--[(2,5-difluorophenyl (perfluoropyrenyl) (2,3-difluorophenyl) borate]⁻; [(perfluorooctyl) (propyl) ammonium]⁺--perfluorophenyl--[(pentafluoronaphthyl (trifluoroindenyl) (2,3,5-trifluorophenyl) borate]⁻; (perfluorooctyl) (hexyl) ammonium]⁺--perfluoropyrenyl--[bis(perfluoroindenyl) (perfluorofluorenyl) borate]⁻; [(perfluorooctyl) (perfluoroisopropyl) phosphonium]⁺--tetrafluoronaphthyl--[(pentafluorofluorenyl (tetrafluoroindenyl) (perfluoronapthyl) borate]⁻; [(perfluorooctyl) (isohexyl) phosphonium]⁺--2,5-difluorophenyl--[(2,5-difluorophenyl (perfluorophenyl) (perfluorofluorenyl) borate]⁻; [(perfluorooctyl) (hexyl) ammonium]⁺--tetrafluoronaphthyl--[(perfluorofluorenyl (tetrafluoroindenyl) (2,3-difluorophenyl) borate]⁻; [(perfluoropentyl) (perfluorohexyl) phosphonium]⁺--perfluorofluorenyl--[bis(perfluoronapthyl) (perfluorofluorenyl) borate]⁻; [(perfluoropentyl) (perfluoromethyl) phosphonium]⁺--perfluorophenyl--[(perfluorofluorenyl (perfluorobiphenyl) (perfluoroindenyl) borate]⁻; [(perfluoropentyl) (isohexyl) phosphonium]⁺--perfluorofluorenyl--[(perfluoroindenyl (pentafluoronaphthyl) (3,4-difluorophenyl) borate]⁻; [(perfluoropentyl) (isopropyl) ammonium]⁺--perfluorophenyl--[(perfluorofluorenyl (perfluorobiphenyl) (perfluoronapthyl) borate]⁻; [(perfluoropentyl) (ethyl (trimethylsilyl)) ammonium]⁺--perfluorobiphenyl--[(perfluoroindenyl (perfluorofluorenyl) (2,5-difluorophenyl) borate]⁻; [(perfluoropentyl) (methyl (triethylsilyl)) ammonium]⁺--perfluorophenyl--[(perfluoroindenyl (pentafluorofluorenyl) (3,4-difluorophenyl) borate]⁻; [(perfluoropentyl) (octyl) ammonium]⁺--perfluorophenyl--[(2,3-difluorophenyl (perfluorofluorenyl) (perfluoronapthyl) borate]⁻; [(perfluoropentyl) (perfluoroethyl) phosphonium]⁺--perfluorobiphenyl--[(perfluorophenyl (perfluorofluorenyl) (perfluoroindenyl) borate]⁻; [(perfluoropentyl) (2,3,5-trifluorophenyl) arsonium]⁺--perfluorophenyl--[(perfluoronapthyl (tetrafluoroindenyl) (2,3,5-trifluorophenyl) borate]⁻; [(perfluoropentyl) (isohexyl) ammonium]⁺--perfluoroindenyl--[(2,3,5-trifluorophenyl (perfluorophenyl) (perfluorofluorenyl) borate]⁻; [(perfluoropentyl) (methyl (trimethylsilyl)) phosphonium]⁺-perfluoroindenyl--[bis(2,5-difluorophenyl) (pentafluoronaphthyl) borate]⁻; [(perfluoropentyl) (perfluoro-t-butyl) ammonium]⁺--perfluorobiphenyl--[(perfluorobiphenyl (2,3,4-trifluorophenyl)

(tetrafluoronaphthyl) borate]⁻; [(perfluorophenyl) (perfluoromethyl) ammonium]⁺--2,5-difluorophenyl--[(perfluoroindenyl) (2,4-difluorophenyl) (trifluoroindenyl) borate]⁻; [(perfluorophenyl) (isohexyl) arsonium]⁺--perfluoropyrenyl--[bis(perfluoroindenyl) (perfluorophenyl) borate]⁻; [(perfluorophenyl) (perfluorobutyl) ammonium]⁺--perfluorophenyl--[(2,3,4-trifluorophenyl (perfluoronapthyl) (perfluoroindenyl) borate]⁻; (bis(perfluorophenyl) ammonium]⁺--perfluorophenyl--[bis(perfluoroindenyl) (perfluorofluorenyl) borate]⁻; [(perfluorophenyl) (perfluoropentyl) ammonium]⁺--perfluoronapthyl--[(perfluoronapthyl (pentafluoronaphthyl) (perfluorophenyl) borate]⁻; [(perfluorophenyl) (pentyl) phosphonium]⁺--pentafluoronaphthyl--[(2,3,4-trifluorophenyl (perfluorobiphenyl) (perfluorofluorenyl) borate]⁻; [(perfluorophenyl) (perfluorohexyl) phosphonium]⁺--perfluorobiphenyl--[bis(perfluoroindenyl) (perfluorofluorenyl) borate]⁻; [(perfluorophenyl) (2,3,5-trifluorophenyl) phosphonium]⁺--perfluoroindenyl--[(trifluoroindenyl (perfluorobiphenyl) (perfluorofluorenyl) borate]⁻; [(perfluoropropyl) (2,3,4,5-tetrafluorophenyl) ammonium]⁺--perfluorobiphenyl--[(perfluorophenyl) (perfluorofluorenyl) (pentafluoronaphthyl) borate]⁻; [(perfluoropropyl) (3-methylpentyl) phosphonium]⁺--2,3,5-trifluorophenyl--[(trifluoroindenyl (tetrafluoronaphthyl) (2,5-difluorophenyl) borate]⁻; [(perfluoro-t-butyl) (1,6-difluorohexyl) ammonium]⁺--pentafluoronaphthyl--[(2,4-difluorophenyl (perfluorophenyl) (tetrafluoroindenyl) borate]⁻; [(perfluoro-t-butyl) (methyl (triethylsilyl)) ammonium]⁺--2,4-difluorophenyl--[(pentafluoronaphthyl (perfluorobiphenyl) (2,4-difluorophenyl) borate]⁻; [(perfluoro-t-butyl) ((methyl (triethylsilyl))) ammonium]⁺--perfluoroindenyl--[(pentafluorofluorenyl (perfluorophenyl) (2,3,5-trifluorophenyl) borate]⁻; [(perfluoro-t-butyl) (ethyl (triethylsilyl)) ammonium]⁺--perfluoropyrenyl--[(trifluoroindenyl (perfluorofluorenyl) (perfluorobiphenyl) borate]⁻; [(perfluoro-t-butyl) (methyl (trimethylsilyl)) ammonium]⁺--3,4-difluorophenyl--[(perfluorobiphenyl (perfluoronapthyl) (2,3-difluorophenyl) borate]⁻; [(perfluoro-t-butyl) (heptyl) ammonium]⁺--pentafluoronaphthyl--[(perfluorophenyl (tetrafluoronaphthyl) (tetrafluoroindenyl) borate]⁻; [(perfluoro-t-butyl) (1,2-difluorohexyl) ammonium]⁺--perfluorofluorenyl--[(perfluorobiphenyl (perfluoronapthyl) (pentafluoronaphthyl) borate]⁻; [(perfluoro-t-butyl) (perfluoroisopropyl) ammonium]⁺--trifluoroindenyl--[(tetrafluoronaphthyl (perfluoroindenyl) (tetrafluoroindenyl) borate]⁻; [(perfluoro-t-butyl) (isopentyl) ammonium]⁺--tetrafluoronaphthyl--[(trifluoroindenyl (tetrafluoroindenyl) (2,3,4-trifluorophenyl) borate]⁻; [(phenyl) (perfluoroisopropyl) ammonium]⁺--perfluorofluorenyl--[bis (perfluorofluorenyl) (2,5-difluorophenyl) borate]⁻; [(phenyl) (pentyl) ammonium]⁺--tetrafluoroindenyl--[(3,4-difluorophenyl (perfluorophenyl) (trifluoroindenyl) borate]⁻; [(phenyl) (3-methylpentyl) ammonium]⁺--2,4-difluorophenyl--[(2,4-difluorophenyl (perfluoropyrenyl) (perfluoronapthyl) borate]⁻; [(propyl) (methyl (trimethylsilyl)) ammonium]⁺--tetrafluoroindenyl--[bis (perfluorophenyl) (perfluorobiphenyl) borate]⁻; [(propyl) (hexyl) arsonium]⁺--pentafluoronaphthyl--[(2,5-difluorophenyl (pentafluoronaphthyl) (perfluorophenyl) borate]⁻; [(propyl) (butyl) phosphonium]⁺--perfluoronapthyl--[(perfluorophenyl (perfluoronapthyl) (perfluoroindenyl) borate]⁻; [(propyl) (hexyl) ammonium]⁺--perfluorofluorenyl--[(perfluorofluorenyl (2,3-difluorophenyl) (2,3,4-trifluorophenyl) borate]⁻; [(propyl) (2,3,5-trifluorophenyl) ammonium]⁺--perfluorobiphenyl--[(pentafluorofluorenyl (perluoronapthyl) (3,4-difluorophenyl) borate]⁻; [(propyl) (2,3,4,5-tetrafluorophenyl) ammonium]⁺--perfluoroindenyl--[(perfluoroindenyl (2,4-difluorophenyl) (perfluorofluorenyl) borate]⁻; [(propyl) (perfluoro-t-butyl) ammonium]⁺--perfluorophenyl--[bis(perfluorophenyl) (pentafluorofluorenyl) borate]⁻; [(propyl) (butyl) ammonium]⁺--perfluorobiphenyl--[(pentafluorofluorenyl (2,5-difluorophenyl) (pentafluoronaphthyl) borate]⁻; [(propyl) (methyl (trimethylsilyl)) ammonium]⁺--tetrafluoronaphthyl--[bis(perfluoroindenyl) (2,3,4-trifluorophenyl) borate]⁻; [(propyl) (perfluorophenyl) ammonium]⁺--perfluorofluorenyl--[(perfluoronapthyl (3,4-difluorophenyl) (tetrafluoroindenyl) borate]⁻; [(propyl) (ethyl (trimethylsilyl)) ammonium]⁺--pentafluorofluorenyl--[(2,3,4-trifluorophenyl (tetrafluoroindenyl) (2,4-difluorophenyl) borate]⁻; [(propyl) (3-methylpentyl) phosphonium]⁺--perfluorophenyl--[(perluoronapthyl (2,3,5-trifluorophenyl) (perfluorophenyl) borate]⁻; [(propyl) (perfluorohexyl) phosphonium]⁺--perfluoronapthyl--[(perfluoropyrenyl (trifluoroindenyl) (perfluorobiphenyl) borate]⁻; [(propyl) (perfluoropropyl) phosphonium]⁺--pentafluorofluorenyl--[(perfluorophenyl (perfluorofluorenyl) (perfluoropyrenyl) borate]⁻; [(t-butyl) (ethyl (trimethylsilyl)) ammonium]⁺--perfluoroindenyl--[bis (perfluorofluorenyl) (trifluoroindenyl) borate]⁻; [(t-butyl) (methyl (trimethylsilyl))phosphonium]⁺--tetrafluoroindenyl--[(3,4-difluorophenyl (trifluoroindenyl) (perfluorobiphenyl) borate]⁻; [(t-butyl) (perfluoroisopentyl) ammonium]⁺--perfluorobiphenyl--[(3,4-difluorophenyl (perfluorofluorenyl) (tetrafluoronaphthyl) borate]⁻; [(t-butyl) (1,2-difluorohexyl) ammonium]⁺--3,4-difluorophenyl--[bis(perfluorobiphenyl) (perfluorofluorenyl) borate]⁻; [(t-butyl) (perfluoroisopentyl) ammonium]⁺--2,4-difluorophenyl--[(perfluoroindenyl (2,3,4-trifluorophenyl) (perfluorophenyl) borate]⁻; [(t-butyl) (perfluoro-t-butyl) ammonium]⁺--perfluorobiphenyl--[(perfluorobiphenyl (2,3,4-trifluorophenyl) (perfluorofluorenyl) borate]⁻; [(t-butyl) (methyl (trimethylsilyl)) ammonium]⁺--tetrafluoronaphthyl--[(2,4-difluorophenyl (perfluorofluorenyl) (perfluoronapthyl) borate]⁻

Exemplary Aluminum-based Zwitterionic Cocatalyst Activators

[((methyl (triethylsilyl))) (heptyl) arsonium]⁺--2,3-difluorophenyl--[(perfluoroindenyl (tetrafluoroindenyl) (tetrafluoronaphthyl) aluminate]⁻; [((methyl (triethylsilyl))) (methyl (trimethylsilyl)) ammonium]⁺--perfluorophenyl--[(tetrafluoroindenyl (perfluoroindenyl) (perfluorobiphenyl) aluminate]⁻; (bis((methyl (triethylsilyl)))phosphonium]⁺--perfluorobiphenyl--[(2,3,4-trifluorophenyl (perfluoroindenyl) (tetrafluoroindenyl) aluminate]⁻; [((methyl (triethylsilyl))) (perfluorophenyl) ammonium]⁺--perfluorofluorenyl--[(perfluorophenyl (pentafluoronaphthyl) (2,3,4-trifluorophenyl) aluminate]⁻; [((methyl (triethylsilyl))) (methyl) ammonium]⁺--tetrafluoroindenyl--[(perfluoronapthyl (perfluorophenyl) (3,4-difluorophenyl) aluminate]⁻; [((methyl (triethylsilyl))) (methyl) ammonium]⁺--2,3,5-trifluorophenyl--[(perfluorobiphenyl (tetrafluoroindenyl) (perfluorophenyl) aluminate]⁻; [((methyl (triethylsilyl))) (propyl) ammonium]⁺--2,3,4-trifluorophenyl--[(perfluoropyrenyl (perfluorofluorenyl) (2,3,4-trifluorophenyl) aluminate]⁻; [(1,2-difluorohexyl) (perfluorobutyl) ammonium]⁺--perfluorophenyl--[bis (perfluorofluorenyl) (2,3,4-trifluorophenyl) aluminate]⁻; [(1,2-difluorohexyl) (isopentyl) ammonium]⁺--perfluoroindenyl--[(2,3-difluorophenyl (tetrafluoroindenyl)

(perfluoropyrenyl) aluminate]⁻; [(1,6-difluorohexyl) (2,3,4,5-tetrafluorophenyl) phosphonium]⁺--3,4-difluorophenyl--[bis(perfluorofluorenyl) (perfluoropyrenyl) aluminate]⁻; [(1,6-difluorohexyl) (perfluoropropyl) phosphonium]⁺--pentafluorofluorenyl--[bis(perfluoroindenyl) (perfluorophenyl) aluminate]⁻; [(1,6-difluorohexyl) (methyl (triethylsilyl)) ammonium]⁺--perfluorofluorenyl--[(perfluoronapthyl) (perfluorophenyl) (perfluoroindenyl) aluminate]⁻; [(2,3,4,5-tetrafluorophenyl) (2,3,5-trifluorophenyl) ammonium]⁺--perfluorophenyl--[(2,3,5-trifluorophenyl) (perfluorofluorenyl) (perfluoroindenyl) aluminate]⁻; [(2,3,4,5-tetrafluorophenyl) (perfluoroisopropyl) phosphonium]⁺--perfluoroindenyl--[(tetrafluoronaphthyl) (perfluorobiphenyl) (2,4-difluorophenyl) aluminate]⁻; [(2,3,5-trifluorophenyl) (perfluoropentyl) phosphonium]⁺--trifluoroindenyl--[(perfluorofluorenyl) (perfluorophenyl) (perfluoroindenyl) aluminate]⁻; [(2,3,5-trifluorophenyl) (isopropyl) ammonium]⁺--perfluoronapthyl--[(trifluoroindenyl) (tetrafluoroindenyl) (pentafluoronaphthyl) aluminate]⁻; [(2,3,6,7-tetrafluorooctyl) (hexyl) ammonium]⁺--perfluoronapthyl--[bis(perfluoropyrenyl) (perfluorofluorenyl) aluminate]⁻; [(2,3,6,7-tetrafluorooctyl) (perfluorobutyl) phosphonium]⁺--perfluorophenyl--[bis(perfluoronapthyl) (pentafluorofluorenyl) aluminate]⁻; [(2,3,6,7-tetrafluorooctyl) (methyl) arsonium]⁺--perfluorophenyl--[(trifluoroindenyl) (tetrafluoronaphthyl) (perfluorobiphenyl) aluminate]⁻; [(2,3,6,7-tetrafluorooctyl) (3-methylpentyl) ammonium]⁺--2,4-difluorophenyl--[bis(perfluoronapthyl) (perfluorophenyl) aluminate]⁻; [(2,3,6,7-tetrafluorooctyl) (ethyl (trimethylsilyl))phosphonium]⁺--2,4-difluorophenyl--[bis(perfluorobiphenyl) (pentafluorofluorenyl) aluminate]⁻; [(3-methylpentyl) (isopentyl) ammonium]⁺--perfluorobiphenyl--[(2,3,4-trifluorophenyl) (perfluorofluorenyl) (perfluoropyrenyl) aluminate]⁻; [(3-methylpentyl) (1,2-difluorohexyl) ammonium]⁺--perfluorofluorenyl--[(tetrafluoroindenyl) (2,5-difluorophenyl) (perfluorofluorenyl) aluminate]⁻; [(3-methylpentyl) (perfluoroheptyl) phosphonium]⁺--perfluoroindenyl--[(2,3,4-trifluorophenyl) (perfluorophenyl) (perfluoroindenyl) aluminate]⁻; [(3-methylpentyl) (methyl) ammonium]⁺--perfluorobiphenyl--[(perfluorophenyl) (2,3,4-trifluorophenyl) (2,5-difluorophenyl) aluminate]⁻; [(3-methylpentyl) (butyl) ammonium]⁺--2,4-difluorophenyl--[(perfluoroindenyl) (perfluorofluorenyl) (perfluoropyrenyl) aluminate]⁻; [(3-methylpentyl) (perfluoromethyl) ammonium]⁺--pentafluorofluorenyl--[(pentafluoronaphthyl) (perfluoronapthyl) (perfluorofluorenyl) aluminate]⁻; [(butyl) (methyl (triethylsilyl)) ammonium]⁺--tetrafluoronaphthyl--[(tetrafluoronaphthyl (2,3,4-trifluorophenyl) (pentafluorofluorenyl) aluminate]⁻; [(butyl) (3-methylpentyl) phosphonium]⁺--tetrafluoroindenyl--[(2,4-difluorophenyl) (perfluoronapthyl) (perfluorobiphenyl) aluminate]⁻; [(butyl) (hexyl) ammonium]⁺--perfluoroindenyl--[(perfluoronapthyl (2,3,5-trifluorophenyl) (perfluoroindenyl) aluminate]⁻; [(ethyl) (3-methylpentyl) ammonium]⁺--perfluorobiphenyl--[bis(trifluoroindenyl) (2,4-difluorophenyl) aluminate]⁻; [(ethyl) (perfluoro-t-butyl) ammonium]⁺--perfluorofluorenyl--[(perfluoroindenyl (2,5-difluorophenyl) (2,3,4-trifluorophenyl) aluminate]⁺; [(ethyl) (isohexyl) phosphonium]⁺--perfluoroindenyl--[(perfluorobiphenyl (perfluoronapthyl) (2,4-difluorophenyl) aluminate]⁻; [(ethyl) (perfluoropentyl) ammonium]⁺--2,4-difluorophenyl--[(tetrafluoronaphthyl (perfluorophenyl) (2,4-difluorophenyl) aluminate]⁻; [(ethyl) (ethyl (trimethylsilyl))phosphonium]⁺--2,3,5-trifluorophenyl--[(perfluoroindenyl (2,4-difluorophenyl) (perfluorophenyl) aluminate]⁻; [(ethyl (triethylsilyl)) (ethyl (trimethylsilyl)) ammonium]⁺--tetrafluoronaphthyl--[(perfluoronapthyl (2,5-difluorophenyl) (pentafluoronaphthyl) aluminate]⁻; [(ethyl (triethylsilyl)) (ethyl (trimethylsilyl)) ammonium]⁺--pentafluorofluorenyl--[bis(perfluoronapthyl) (perfluoroindenyl) aluminate]⁻; [(ethyl (triethylsilyl)) (ethyl (trimethylsilyl)) ammonium]⁺--perfluoronapthyl--[bis(perfluorofluorenyl) (perfluoroindenyl) aluminate]⁻; [(ethyl (trimethylsilyl)) (3-methylpentyl) phosphonium]⁺--perfluorofluorenyl--[(perfluorobiphenyl (tetrafluoronaphthyl) (perfluorofluorenyl) aluminate]⁻; [(ethyl (trimethylsilyl)) (2,3,5-trifluorophenyl) phosphonium]⁺--perfluoroindenyl--[(perfluoronapthyl (2,5-difluorophenyl) (perfluoroindenyl) aluminate]⁻; [(ethyl (trimethylsilyl)) (propyl) ammonium]⁺--pentafluorofluorenyl--[(perfluoronapthyl (3,4-difluorophenyl) (2,3-difluorophenyl) aluminate]⁻; [(ethyl (trimethylsilyl)) (heptyl) phosphonium]⁺--pentafluoronaphthyl--[bis(perfluorofluorenyl) (2,3,5-trifluorophenyl) aluminate]⁻; [(ethyl (trimethylsilyl)) (isohexyl) ammonium]⁺--perfluoroindenyl--[(perfluoroindenyl (perfluoronapthyl) (perfluorophenyl) aluminate]⁻; [(ethyl (trimethylsilyl)) (octyl) ammonium]⁺--perfluorobiphenyl--[bis(perfluorophenyl) (perfluoroindenyl) aluminate]⁻; [(ethyl (trimethylsilyl)) (ethyl) ammonium]⁺--perfluorophenyl--[(perfluorofluorenyl (perfluorobiphenyl) (trifluoroindenyl) aluminate]⁻; [(heptyl) (ethyl (triethylsilyl)) ammonium]⁺--2,5-difluorophenyl--[bis(perfluorobiphenyl) (perfluorofluorenyl) aluminate]⁻; [(hexyl) (isopentyl) ammonium]⁺--perfluorofluorenyl--[(perfluorofluorenyl) (perfluorobiphenyl) (perfluorophenyl) aluminate]⁻; [(hexyl) (perfluoroheptyl) phosphonium]⁺--perfluoroindenyl--[bis(perfluoroindenyl) (2,3,5-trifluorophenyl) aluminate]⁻; [(hexyl) (t-butyl) ammonium]⁺--perfluoroindenyl--[(perfluorobiphenyl (3,4-difluorophenyl) (trifluoroindenyl) aluminate]⁻; [(isohexyl) (t-butyl) ammonium]⁺--perfluorobiphenyl--[(perfluoropyrenyl) (perfluorophenyl) (pentafluorofluorenyl) aluminate]⁻; [(isohexyl) (perfluorooctyl) ammonium]⁺--perfluoronapthyl--[bis(perfluoroindenyl) (perfluoronapthyl) aluminate]⁻; [(isohexyl) (perfluoro-t-butyl) ammonium]⁺--perfluoronapthyl--[(perfluoropyrenyl) (pentafluorofluorenyl) (3,4-difluorophenyl) aluminate]⁻; [(isohexyl) (t-butyl) ammonium]⁺--perfluorobiphenyl--[(perfluoronapthyl (2,3,4-trifluorophenyl) (2,4-difluorophenyl) aluminate]⁻; [(isohexyl) (propyl) ammonium]⁺--perfluorofluorenyl-[(perfluorophenyl (2,3-difluorophenyl) (2,5-difluorophenyl) aluminate]⁻; (bis(isohexyl) ammonium]⁺--perfluoroindenyl--[bis(perfluorobiphenyl) (perfluorofluorenyl) aluminate]⁻; [(isohexyl) (3-methylpentyl) phosphonium]⁺--perfluorophenyl--[(perfluorofluorenyl (2,3,4-trifluorophenyl) (perfluorobiphenyl) aluminate]⁻; [(isopentyl) (methyl (triethylsilyl)) ammonium]⁺--2,3-difluorophenyl--[tris (perfluorobiphenyl) aluminate]⁻; [(isopentyl) (propyl) arsonium]⁺--2,3,5-trifluorophenyl--[bis(tetrafluoronaphthyl) (perfluorophenyl) aluminate]⁻; [(isopentyl) (perfluoro-t-butyl) ammonium]⁺--perfluorophenyl--[bis (tetrafluoroindenyl) (3,4-difluorophenyl) aluminate]⁻; [(isopropyl) (perfluorohexyl) ammonium]⁺--perfluoronapthyl--[bis(perfluorophenyl) (2,5-difluorophenyl) aluminate]⁻; [(methyl) (isopentyl) ammonium]⁺--pentafluoronaphthyl--[(perfluoroindenyl) (perfluoropyrenyl) (perfluoronapthyl) aluminate]⁻; [(methyl) (isohexyl) ammonium]⁺--perfluorophenyl--[(2,5-difluorophenyl (perfluoroindenyl) (perfluorobiphenyl) aluminate]⁻; [(methyl) (2,3,6,7-tetrafluorooctyl)

ammonium]⁺--perfluoronapthyl--[(perfluorofluorenyl) (tetrafluoronaphthyl) (pentafluorofluorenyl) aluminate]⁻; [(methyl) (ethyl (trimethylsilyl)) ammonium]⁺--perfluoronapthyl--[(2,3,5-trifluorophenyl) (perfluoronapthyl) (3,4-difluorophenyl) aluminate]⁻; [(methyl (triethylsilyl)) (ethyl) ammonium]⁺--2,5-difluorophenyl--[(pentafluoronaphthyl) (perfluoronapthyl) (tetrafluoronaphthyl) aluminate]⁻; [(methyl (triethylsilyl)) (2,3,6,7-tetrafluorooctyl) phosphonium]⁺--perfluorophenyl--[(perfluorophenyl (perfluoropyrenyl) (3,4-difluorophenyl) aluminate]⁻; [(methyl (triethylsilyl)) (2,3,4,5-tetrafluorophenyl) ammonium]⁺--perfluorofluorenyl--[(2,3,5-trifluorophenyl (tetrafluoronaphthyl) (perfluoroindenyl) aluminate]⁻; [(methyl (triethylsilyl)) (perfluoroethyl) ammonium]⁺--3,4-difluorophenyl--[(2,5-difluorophenyl (perfluorophenyl) (3,4-difluorophenyl) aluminate]⁻; [(methyl (trimethylsilyl)) (perfluoropentyl) phosphonium]⁺--perfluoronapthyl--[bis(perfluoroindenyl) (perfluoropyrenyl) aluminate]⁻; [(methyl (trimethylsilyl)) (3-methylpentyl) ammonium]⁺--2,3,4-trifluorophenyl--[(perfluorofluorenyl perfluorophenyl) (perfluoropyrenyl) aluminate]⁻; [(methyl (trimethylsilyl)) ((methyl (triethylsilyl))) ammonium]⁺--2,3-difluorophenyl--[(perfluorofluorenyl) (2,5-difluorophenyl) (perfluorophenyl) aluminate]⁻; [(methyl (trimethylsilyl)) (methyl) ammonium]⁺--perfluorophenyl--[(perfluorobiphenyl) (perfluoronapthyl) (2,3,4-trifluorophenyl) aluminate]⁻; [(octyl) (1,2-difluorohexyl) ammonium]⁺--perfluorophenyl--[(2,3,5-trifluorophenyl (2,5-difluorophenyl) (perfluoronaphthyl) aluminate]⁻; [(octyl) (2,3,5-trifluorophenyl) ammonium]⁺--pentafluorofluorenyl--[(2,3,5-trifluorophenyl (perfluoronaphthyl) (perfluorobiphenyl) aluminate]⁻; [(octyl) (isopropyl) phosphonium]⁺--pentafluorofluorenyl--[(2,3-difluorophenyl (perfluoronaphthyl) (pentafluorofluorenyl) aluminate]⁻; [(octyl) (isopropyl) ammonium]⁺--perfluorofluorenyl--[(perfluoronapthyl) (perfluorofluorenyl) (tetrafluoronaphthyl) aluminate]⁻; [(octyl) (perfluoroethyl) ammonium]⁺--perfluorobiphenyl--[(perfluorobiphenyl) (perfluorofluorenyl) (perfluorophenyl) aluminate]⁻; [(pentyl) (2,3,4,5-tetrafluorophenyl) phosphonium]⁺--pentafluoronaphthyl--[(perfluoronapthyl) (perfluorobiphenyl) (2,4-difluorophenyl) aluminate]⁻; [(pentyl) (2,3,6,7-tetrafluorooctyl) ammonium]⁺--perfluoroindenyl--[bis(2,3-difluorophenyl) (perfluorophenyl) aluminate]⁻; [(perfluorobutyl) (isopentyl) ammonium]⁺--2,4-difluorophenyl--[bis(perfluorophenyl) (perfluorofluorenyl) aluminate]⁻; [(perfluorobutyl) (isohexyl) arsonium]⁺--perfluorobiphenyl--[bis (perfluorophenyl) (2,3-difluorophenyl) aluminate]⁻; [(perfluorobutyl) (perfluorophenyl) arsonium]⁺--2,3,5-trifluorophenyl--[bis(perfluorophenyl) (2,5-difluorophenyl) aluminate]⁻; [(perfluoroethyl) (1,6-difluorohexyl) arsonium]⁺--tetrafluoroindenyl--[(pentafluoronaphthyl) (tetrafluoroindenyl) (perfluoroindenyl) aluminate]⁻; [(perfluoroethyl) (ethyl) ammonium]⁺--perfluorobiphenyl--[(perfluoronapthyl) (trifluoroindenyl) (2,5-difluorophenyl) aluminate]⁻; [(perfluoroethyl) (perfluoromethyl) phosphonium]⁺--tetrafluoronaphthyl--[(perfluoroindenyl) (perfluorophenyl) (perfluorobiphenyl) aluminate]⁻; [(perfluoroheptyl) (3-methylpentyl) ammonium]⁺--2,3-difluorophenyl--[(pentafluorofluorenyl) (2,3,5-trifluorophenyl) (perfluorobiphenyl) aluminate]⁻; [(perfluoroheptyl) (perfluoropropyl) phosphonium]⁺--perfluorobiphenyl--[(2,3,5-trifluorophenyl (perfluorobiphenyl) (perfluoroindenyl) aluminate]⁻; [(perfluoroheptyl) (perfluoroisopentyl) ammonium]⁺--perfluorophenyl--[(perfluorophenyl (pentafluorofluorenyl) (3,4-difluorophenyl) aluminate]⁻; [(perfluorohexyl) (isopropyl) arsonium]⁺--perfluoronapthyl--[(perfluorophenyl) (perfluoroindenyl) (perfluorofluorenyl) aluminate]⁻; [(perfluorohexyl) (perfluoropropyl) phosphonium]⁺--3,4-difluorophenyl--[bis(2,3,5-trifluorophenyl) (perfluoronapthyl) aluminate]⁻; [(perfluorohexyl) (perfluoropropyl) ammonium]⁺--3,4-difluorophenyl--[(tetrafluoronaphthyl (2,3-difluorophenyl) (perfluorofluorenyl) aluminate]⁻; [(perfluoroisopentyl) (ethyl (trimethylsilyl)) ammonium]⁺--pentafluorofluorenyl--[(perfluoroindenyl) (perfluorobiphenyl) (perfluoronapthyl) aluminate]⁻; [(perfluoroisopentyl) (2,3,4,5-tetrafluorophenyl) ammonium]⁺--2,3-difluorophenyl--[(2,4-difluorophenyl) (perfluoronapthyl) (perfluoroindenyl) aluminate]⁻; [(perfluoroisopentyl) (1,6-difluorohexyl) ammonium]⁺--perfluoropyrenyl--[(2,3-difluorophenyl) (2,3,5-trifluorophenyl) (pentafluoronaphthyl) aluminate]⁻; [(perfluoroisopentyl) (perfluorobutyl) ammonium]⁺--perfluorophenyl--[(pentafluorofluorenyl) (3,4-difluorophenyl) (2,5-difluorophenyl) aluminate]⁻; [(perfluoroisopropyl) (methyl) ammonium]⁺--2,3-difluorophenyl--[bis(perfluoronapthyl) (pentafluorofluorenyl) aluminate]⁻; [(perfluoroisopropyl) (ethyl) ammonium]⁺--perfluoroindenyl--[(perfluoronapthyl) (perfluorofluorenyl) (2,3-difluorophenyl) aluminate]⁻; [(perfluoroisopropyl) (perfluoroheptyl) arsonium]⁺--perfluoroindenyl--[bis(perfluorophenyl) (pentafluoronaphthyl) aluminate]⁻; [(perfluoroisopropyl) ((methyl (triethylsilyl))) ammonium]⁺--3,4-difluorophenyl--[(2,3,4-trifluorophenyl) (perfluorobiphenyl) (perfluorophenyl) aluminate]⁻; [(perfluoromethyl) (isopropyl) phosphonium]⁺--perfluoroindenyl--[(trifluoroindenyl) (perfluoronapthyl) (2,3,5-trifluorophenyl) aluminate]⁻; [(perfluorooctyl) (perfluoropentyl) ammonium]⁺--perfluorophenyl--[(perfluoroindenyl) (2,4-difluorophenyl) (perfluorofluorenyl) aluminate]⁻; [(perfluorooctyl) (perfluorobutyl) phosphonium]⁺--perfluorofluorenyl--[(perfluorofluorenyl) (2,4-difluorophenyl) (tetrafluoronaphthyl) aluminate]⁻; [(perfluoropentyl) (perfluoro-t-butyl) arsonium]⁺--perfluorofluorenyl--[(perfluoroindenyl) (pentafluoronaphthyl) (tetrafluoronaphthyl) aluminate]⁻; [(perfluoropentyl) (methyl (trimethylsilyl)) ammonium]⁺--2,4-difluorophenyl--[(perfluoroindenyl) (perfluoropyrenyl) (perfluorophenyl) aluminate]⁻; [(perfluoropentyl) (ethyl (trimethylsilyl)) ammonium]⁺--perfluorobiphenyl--[(perfluorofluorenyl) (2,3,5-trifluorophenyl) (pentafluorofluorenyl) aluminate]⁻; [(perfluoropentyl) (methyl (trimethylsilyl))phosphonium]⁺--perfluorofluorenyl--[(perfluorobiphenyl (2,5-difluorophenyl) (trifluoroindenyl) aluminate]⁻; [(perfluorophenyl) (methyl (trimethylsilyl)) ammonium]⁺--pentafluorofluorenyl--[(tetrafluoronaphthyl) (perfluoroindenyl) (trifluoroindenyl) aluminate]⁻; [(perfluorophenyl) (methyl) phosphonium]⁺--3,4-difluorophenyl--[(pentafluoronaphthyl) (tetrafluoroindenyl) (perfluorobiphenyl) aluminate]⁻; [(perfluorophenyl) (octyl) phosphonium]⁺--perfluoroindenyl--[bis(perfluoronapthyl) (2,3,5-trifluorophenyl) aluminate]⁻; [(perfluorophenyl) (perfluoropropyl) ammonium]⁺--perfluoronapthyl--[(perfluorofluorenyl (pentafluoronaphthyl) (perfluoronapthyl) aluminate]⁻; [(perfluorophenyl) (methyl) ammonium]⁺--pentafluoronaphthyl--[(perfluorofluorenyl) (2,3-difluorophenyl) (trifluoroindenyl) aluminate]⁻; [(perfluorophenyl) (perfluoromethyl) ammonium]⁺-- perfluoroindenyl--[(perfluorophenyl (pentafluoronaphthyl) (perfluoroindenyl) aluminate]⁻; [(perfluorophenyl) (perfluorohexyl) ammonium]⁺--perfluorophenyl--[bis(2,3-difluorophenyl) (perfluorobiphenyl) aluminate]⁻; [(perfluoropropyl) (isopropyl) ammonium]⁺--3,4-difluorophenyl--[(tetrafluoroindenyl (2,3,4-trifluorophenyl) (perfluoropyrenyl) aluminate]⁻; [(perfluoropropyl) (perfluorohexyl) phosphonium]⁺--tetrafluoronaphthyl--[(tetrafluoronaphthyl (pentafluorofluorenyl) (2,5-difluorophenyl) aluminate]⁻; [(perfluoropropyl) (methyl (trimethylsilyl)) ammonium]⁺--trifluoroindenyl--[(perfluoroindenyl) (perfluoropyrenyl) (perfluorofluorenyl) aluminate]⁻; [(perfluoro-t-butyl) (3-methylpentyl) ammonium]⁺--perfluorofluorenyl--[bis(2,3-difluorophenyl) (perfluorobiphenyl) aluminate]⁻; [(phenyl) (1,6-difluorohexyl) phosphonium]⁺--perfluorophenyl--[bis(perfluorobiphenyl) (tetrafluoronaphthyl) aluminate]⁻; [(phenyl) (perfluoroethyl) ammonium]⁺--perfluoropyrenyl--[(perfluoroindenyl) (tetrafluoroindenyl) (perfluorobiphenyl) aluminate]⁻; [(propyl) (ethyl (triethylsilyl))phosphonium]⁺--2,4-difluorophenyl--[(2,3,4-trifluorophenyl (pentafluorofluorenyl) (perfluorofluorenyl) aluminate]⁻; [(propyl) (3-methylpentyl) phosphonium]⁺--3,4-difluorophenyl--[(2,3,4-trifluorophenyl (perfluorophenyl) (perfluorofluorenyl) aluminate]⁻; [(propyl) (3-methylpentyl) arsonium]⁺--2,3,4-trifluorophenyl--[bis(perfluorophenyl) (2,4-difluorophenyl) aluminate]⁻; [(t-butyl) (2,3,5-trifluorophenyl) ammonium]⁺--perfluoropyrenyl--[(perfluoronapthyl (perfluorophenyl) (tetrafluoronaphthyl) aluminate]⁻; [(t-butyl) (methyl (trimethylsilyl)) ammonium]⁺--perfluorofluorenyl--[(perfluorobiphenyl (2,3,5-trifluorophenyl) (2,3,4-trifluorophenyl) aluminate]⁻; [(t-butyl) (perfluoroethyl) ammonium]⁺--perfluoronapthyl--[(perfluoronapthyl (2,3-difluorophenyl) (perfluorofluorenyl) aluminate]⁻.

Exemplary Gallium-based Zwitterionic Cocatalyst Activators

[((methyl (triethylsilyl))) (3-methylpentyl) ammonium]+--perfluorobiphenyl--[(perfluoronapthyl (perfluorobiphenyl) (perfluorofluorenyl) gallinate]–; [(1,2-difluorohexyl) (ethyl (tri-ethylsilyl)) ammonium]+--perfluoronapthyl--[bis(2,5-difluorophenyl) (perfluorofluorenyl) gallinate]–; [(1,6-difluorohexyl) (butyl) phosphonium]+---perfluorobiphenyl--[(perfluorophenyl (2,3-difluorophenyl) (perfluoropyrenyl) gallinate]–; [(1,6-difluorohexyl) (perfluoro-t-butyl) phosphonium]+--perfluoronapthyl--[(perfluoroindenyl (2,5-difluorophenyl) (3,4-difluorophenyl) gallinate]–; [(1,6-difluorohexyl) (phenyl) phosphonium]+--2,3,4-trifluorophenyl--[(2,3,4-trifluorophenyl (2,3-difluorophenyl) (perfluorobiphenyl) gallinate]–; [(2,3,5-trifluorophenyl) (pentyl) phosphonium]+--tetrafluoroindenyl--[(perfluorobiphenyl (pentafluorofluorenyl) (perfluoroindenyl) gallinate]–; [(3-methylpentyl) (butyl) arsonium]+--perfluoronapthyl--[(2,5-difluorophenyl (2,3,5-trifluorophenyl) (perfluoroindenyl) gallinate]–; [(3-methylpentyl) (octyl) ammonium]+--perfluorobiphenyl--[(perfluorofluorenyl (perfluorophenyl) (2,3,5-trifluorophenyl) gallinate]–; [(butyl) (isohexyl) ammonium]+--tetrafluoroindenyl--[(2,3,5-trifluorophenyl (2,3,4-trifluorophenyl) (perfluorophenyl) gallinate]–; (bis (ethyl (triethylsilyl)) ammonium]+--pentafluorofluorenyl--[(2,3,4-trifluorophenyl (tetrafluoronaphthyl) (perfluoronapthyl) gallinate]–; [(ethyl (triethylsilyl)) (ethyl (trimethylsilyl))phosphonium]+--2,3,5-trifluorophenyl--[(trifluoroindenyl (3,4-difluorophenyl) (2,4-difluorophenyl) gallinate]–; [(ethyl (triethylsilyl)) (perfluoroisopropyl) ammonium]+--perfluoronapthyl--[(3,4-difluorophenyl (2,5-difluorophenyl) (tetrafluoronaphthyl) gallinate]–; [(ethyl (triethylsilyl)) (perfluorohexyl) phosphonium]+--perfluorofluorenyl-[(perfluorophenyl (perfluoroindenyl) (2,3,5-trifluorophenyl) gallinate]–; [(ethyl (triethylsilyl)) (3-methylpentyl) ammonium]+--2,3-difluorophenyl--[(perfluorophenyl (perfluorofluorenyl) (perfluoroindenyl) gallinate]–; [(ethyl (triethylsilyl)) (3-methylpentyl) ammonium]+--trifluoroindenyl--[(perfluoroindenyl (pentafluorofluorenyl) (tetrafluoronaphthyl) gallinate]–; [(ethyl (trimethylsilyl)) (3-methylpentyl) ammonium]+--perfluorofluorenyl--[(2,4-difluorophenyl (perfluorofluorenyl) (2,3,4-trifluorophenyl) gallinate]–; [(heptyl) (3-methylpentyl) ammonium]+--tetrafluoronaphthyl--[bis(perfluorobiphenyl) (2,4-difluorophenyl) gallinate]–; [(hexyl) (2,3,4,5-tetrafluorophenyl) arsonium]+--2,5-difluorophenyl--[(pentafluorofluorenyl (2,3-difluorophenyl) (trifluoroindenyl) gallinate]–; [(isohexyl) (propyl) ammonium]+--3,4-difluorophenyl--[(perfluoroindenyl (2,5-difluorophenyl) (perfluorobiphenyl) gallinate]–; [(isohexyl) (3-methylpentyl) ammonium]+--3,4-difluorophenyl--[(2,5-difluorophenyl (perfluorophenyl) (perfluoroindenyl) gallinate]–; [(isohexyl) (ethyl) ammonium]+--pentafluorofluorenyl--[bis(perfluorophenyl) (perfluorofluorenyl) gallinate]–; [(isohexyl) (ethyl (trimethylsilyl)) ammonium]+--2,3,5-trifluorophenyl--[(2,5-difluorophenyl (perfluorofluorenyl) (perfluorophenyl) gallinate]–; [(isopropyl) (phenyl) phosphonium]+--2,3,5-trifluorophenyl--[(2,3,4-trifluorophenyl (perfluorofluorenyl) (2,3-difluorophenyl) gallinate]–; [(isopropyl) (perfluoromethyl) ammonium]+---perfluorophenyl--[(perfluorophenyl (perfluorofluorenyl) (2,3,4-trifluorophenyl) gallinate]–; (bis(isopropyl) ammonium]+--perfluoroindenyl--[(trifluoroindenyl (tetrafluoronaphthyl) (perfluoropyrenyl) gallinate]–; [(isopropyl) (ethyl (trimethylsilyl)) arsonium]+--perfluorofluorenyl--[(2,5-difluorophenyl (perfluorobiphenyl) (tetrafluoronaphthyl) gallinate]–; (bis(methyl) ammonium]+--2,3-difluorophenyl--[bis(perfluoronapthyl) (perfluorofluorenyl) gallinate]–; [(methyl) (ethyl) ammonium]+--perfluorofluorenyl--[bis(perfluorobiphenyl) (perfluoroindenyl) gallinate]–; [(methyl) (octyl) ammonium]+--pentafluorofluorenyl--[(perfluorofluorenyl (perfluorobiphenyl) (trifluoroindenyl) gallinate]–; [(methyl (trimethylsilyl)) (2,3,5-trifluorophenyl) ammonium]+--perfluorophenyl--[(2,3,4-trifluorophenyl (perfluorobiphenyl) (pentafluoronaphthyl) gallinate]–; [(methyl (trimethylsilyl)) (3-methylpentyl) arsonium]+--tetrafluoroindenyl--[(pentafluoronaphthyl (perfluoroindenyl) (perfluorophenyl) gallinate]–; [(methyl (trimethylsilyl)) (perfluorohexyl) phosphonium]+--2,3,5-trifluorophenyl--[(pentafluorofluorenyl (2,5-difluorophenyl) (perfluorobiphenyl) gallinate]–; [(pentyl) (ethyl) ammonium]+--tetrafluoronaphthyl--[(perfluoronapthyl (perfluoropyrenyl) (perfluoroindenyl) gallinate]–; [(perfluorobutyl) (perfluoroisopentyl) ammonium]+--perfluorophenyl--[bis(perfluorophenyl) (trifluoroindenyl) gallinate]–; [(perfluorobutyl) (perfluorophenyl) arsonium]+--2,3,5-trifluorophenyl--[(perfluorobiphenyl (perfluorofluorenyl) (2,3,4-trifluorophenyl) gallinate]–; (bis (perfluorohexyl) arsonium]+--perfluoronapthyl--[(2,3,4-trifluorophenyl (perfluorophenyl) (perfluoronapthyl) gallinate]–; [(perfluorohexyl) (methyl (trimethylsilyl)) ammonium]+--perfluorofluorenyl--[(tetrafluoronaphthyl (2,3,5-trifluorophenyl) (perfluorobiphenyl) gallinate]–; [(perfluorohexyl) (ethyl) phosphonium]+--2,3,5-trifluorophenyl--[bis(perfluorobiphenyl) (perfluoroindenyl)

gallinate]–; [(perfluoroisopentyl) (butyl) ammonium]+--perfluoroindenyl--[(perfluorophenyl (2,3,4-trifluorophenyl) (tetrafluoroindenyl) gallinate]–; [(perfluoroisopropyl) (perfluoromethyl) ammonium]+--perfluoronapthyl--[bis (perfluoronapthyl) (pentafluorofluorenyl) gallinate]–; [(perfluorooctyl) (ethyl (trimethylsilyl)) ammonium]+--perfluorobiphenyl--[(2,3-difluorophenyl (perfluoronapthyl) (perluorophenyl) gallinate]–; [(perfluorophenyl) (methyl (trimethylsilyl)) ammonium]+--perfluoronapthyl--[(perfluorofluorenyl (perfluoropyrenyl) (perfluorobiphenyl) gallinate]–; [(perfluorophenyl) (isohexyl) phosphonium]+--perfluorofluorenyl--[(perfluoroindenyl (tetrafluoroindenyl) (perfluorobiphenyl) gallinate]–; [(perfluorophenyl) (perfluoromethyl) arsonium]+--perfluoroindenyl--[(pentafluoronaphthyl (2,3-difluorophenyl) (perfluorophenyl) gallinate]–; [(perfluoropropyl) (propyl) phosphonium]+--perfluorophenyl--[(2,4-difluorophenyl (2,3,5-trifluorophenyl) (pentafluorofluorenyl) gallinate]–; [(perfluoro-t-butyl) (ethyl) ammonium]+--perfluorophenyl--[(perfluorophenyl (2,3,5-trifluorophenyl) (perfluoronapthyl) gallinate]–; [(t-butyl) (isohexyl) ammonium]+--trifluoroindenyl--[(perfluoronapthyl (pentafluoronaphthyl) (perfluoropyrenyl) gallinate]–; [(t-butyl) (perfluoroisopropyl) phosphonium]+--perfluorophenyl--[(perfluoronapthyl (perfluoroindenyl) (perfluorofluorenyl) gallinate]

Exemplary Zwitterionic Cocatalyst/Catalyst Systems Before Reaction to Activate the Catalyst

[(methyl(triethylsilyl)) (2,3,4,5-tetrafluorophenyl) phosphonium]+--perfluorobiphenyl--[(2,3,5-trifluorophenyl (perfluorobiphenyl) (2,3,4-trifluorophenyl)aluminate]–/(4-alkyl-1-phenyl) (4-t-butyl-1-phenyl)methyl (cylcopentadienyl) (fluorenyl) hafnium dimethyl; [(methyl (trimethylsilyl)) (perfluoropentyl) phosphonium]+--perfluorophenyl--[(perfluorofluorenyl(tetrafluoronaphthyl) (perfluoronapthyl)aluminate]–/(4-alkyl-1-phenyl) (4-t-butyl-1-phenyl)methyl (cylcopentadienyl) (fluorenyl) hafnium dimethyl; [(methyl(trimethylsilyl)) (isohexyl) phosphonium]+--perfluoronapthyl--[(3,4-difluorophenyl (perfluorophenyl) (2,3-difluorophenyl)aluminate]–/(4-alkyl-1-phenyl) (4-t-butyl-1-phenyl)methyl (cylcopentadienyl) (fluorenyl) hafnium dimethyl; [(perfluoropentyl) (ethyl (trimethylsilyl)) phosphonium]+--2,3,5-trifluorophenyl--[bis(pentafluorofluorenyl) (3,4-difluorophenyl)aluminate]–/(4-alkyl-1-phenyl) (4-t-butyl-1-phenyl)methyl (cylcopentadienyl) (fluorenyl) hafnium dimethyl; [(1,6-difluorohexyl) (isohexyl) phosphonium]+--pentafluorofluorenyl--[(pentafluoronaphthyl(2,3,5-trifluorophenyl) (perfluorofluorenyl)borate]–/(4-alkyl-1-phenyl) (4-t-butyl-1-phenyl)methyl (cylcopentadienyl) (fluorenyl) hafnium dimethyl; [(butyl) (methyl (trimethylsilyl))ammonium]+--perfluorobiphenyl--[(2,4-difluorophenyl(2,3,5-trifluorophenyl) (2,5-difluorophenyl) borate]–/(4-alkyl-1-phenyl) (4-t-butyl-1-phenyl)methyl (cylcopentadienyl) (fluorenyl) hafnium dimethyl; [(ethyl) (1,6-difluorohexyl) phosphonium]+--2,4-difluorophenyl--[(2,3,5-trifluorophenyl(perfluorofluorenyl) (perfluoroindenyl)borate]–/(4-alkyl-1-phenyl) (4-t-butyl-1-phenyl)methyl (cylcopentadienyl) (fluorenyl) hafnium dimethyl; [(ethyl(trimethylsilyl)) (1,2-difluorohexyl) ammonium]+--perfluoronapthyl--[(perfluorofluorenyl (trifluoroindenyl) (perfluoronapthyl)borate]–/(4-alkyl-1-phenyl) (4-t-butyl-1-phenyl)methyl (cylcopentadienyl) (fluorenyl) hafnium dimethyl; [(heptyl) (isopentyl) arsonium]+--pentafluorofluorenyl--[bis(perfluoroindenyl) (perfluorofluorenyl)borate]–/(4-alkyl-1-phenyl) (4-t-butyl-1-phenyl)methyl (cylcopentadienyl) (fluorenyl) hafnium dimethyl; [(isohexyl) (perfluorophenyl)ammonium]+--pentafluoronaphthyl--[bis(perfluoroindenyl) (pentafluoronaphthyl)borate]–/(4-alkyl-1-phenyl) (4-t-butyl-1-phenyl)methyl (cylcopentadienyl) (fluorenyl) hafnium dimethyl; [(methyl(triethylsilyl)) (3-methylpentyl) ammonium]+--2,3-difluorophenyl--[(perfluoronapthyl (perfluoroindenyl) (perfluorofluorenyl)borate]–/(4-alkyl-1-phenyl) (4-t-butyl-1-phenyl)methyl (cylcopentadienyl) (fluorenyl) hafnium dimethyl; [(pentyl) (heptyl) ammonium]+--2,4-difluorophenyl--[(perfluorobiphenyl(2,3,4-trifluorophenyl) (3,4-difluorophenyl)borate]–/(4-alkyl-1-phenyl) (4-t-butyl-1-phenyl)methyl (cylcopentadienyl) (fluorenyl) hafnium dimethyl; [(perfluoroisopentyl) (1,6-difluorohexyl) phosphonium]+--perfluoronapthyl--[(2,5-difluorophenyl(perfluorobiphenyl) (perfluorophenyl) borate]–/(4-alkyl-1-phenyl) (4-t-butyl-1-phenyl)methyl (cylcopentadienyl) (fluorenyl) hafnium dimethyl; [(perfluoromethyl) (perluorophenyl)ammonium]+--perfluoroindenyl--[(2,3,4-trifluorophenyl(3,4-difluorophenyl) (tetrafluoroindenyl)borate]–/(4-alkyl-1-phenyl) (4-t-butyl-1-phenyl)methyl (cylcopentadienyl) (fluorenyl) hafnium dimethyl; [(perfluoropentyl) (t-butyl) phosphonium]+--perfluorobiphenyl--[(perfluorophenyl (perfluoroindenyl) (perfluorofluorenyl)borate]–/(4-alkyl-1-phenyl) (4-t-butyl-1-phenyl)methyl (cylcopentadienyl) (fluorenyl) hafnium dimethyl; [(octyl) (isopropyl) ammonium]–--perfluoronapthyl--[(perfluoronapthyl(2,5-difluorophenyl) (2,3-difluorophenyl)aluminate]–/(pentamethylcyclopentadienyl) (cyclopentadienyl) zirconium dimethyl; [(perfluoropentyl) (perfluoroisopentyl) ammonium]+--pentafluorofluorenyl--[bis(perfluoronapthyl) (2,3,5-trifluorophenyl)aluminate]–/(pentamethylcyclopentadienyl) (cyclopentadienyl) zirconium dimethyl; [(1,2-difluorohexyl) (octyl)ammonium]+--perfluorophenyl--[(2,3,5-trifuorophenyl (tetrafluoronaphthyl) (perfluoropyrenyl)borate]–/(pentamethylcyclopentadienyl) (cyclopentadienyl) zirconium dimethyl; [(1,2-difluorohexyl) ((methyl (triethylsilyl)))ammonium]+--2,4-difluorophenyl--[(pentafluoronaphthyl(2,5-difluorophenyl) (perfluoroindenyl)borate]–/(pentamethylcyclopentadienyl) (cyclopentadienyl) zirconium dimethyl; [(2,3,4,5-tetrafluorophenyl) (methyl(trimethylsilyl))ammonium]+--3,4-difluorophenyl--[(tetrafluoroindenyl(perfluorophenyl) (2,5-difluorophenyl)borate]–/(pentamethylcyclopentadienyl) (cyclopentadienyl) zirconium dimethyl; [(butyl) (isohexyl)ammonium]+--pentafluorofluorenyl--[(2,3,5-trifluorophenyl (perfluoroindenyl) (perfluorophenyl)borate]–/(pentamethylcyclopentadienyl) (cyclopentadienyl) zirconium dimethyl; [(butyl) (isohexyl) phosphonium]+--pentafluorofluorenyl--[bis(perfluorofluorenyl) (tetrafluoroindenyl)borate]–/(pentamethylcyclopentadienyl) (cyclopentadienyl) zirconium dimethyl; [(ethyl) (2,3,6,7-tetrafluorooctyl)ammonium]+--perfluoroindenyl--[(perfluorophenyl(pentafluorofluorenyl) (tetrafluoroindenyl) borate]–l(pentamethylcyclopentadienyl) (cyclopentadienyl) zirconium dimethyl; [(hexyl) (ethyl(triethylsilyl)) ammonium]+--pentafluoronaphthyl--[(perfluorobiphenyl (perfluoronapthyl) (tetrafluoronaphthyl)borate]–/(pentamethylcyclopentadienyl) (cyclopentadienyl) zirconium dimethyl; [(isohexyl) (phenyl)ammonium]+--pentafluoronaphthyl--[bis(perfluorobiphenyl) (perfluoronapthyl)borate]–/(pentamethylcyclopentadienyl) (cyclopentadienyl) zirconium dimethyl; [(isohexyl) (3-methylpentyl)ammonium]+--perfluorobiphenyl-[bis (perfluoronapthyl) (trifluoroindenyl)borate]–/

(pentamethylcyclopentadienyl) (cyclopentadienyl) zirconium dimethyl; [(isopentyl) (ethyl(trimethylsilyl)) ammonium]⁺--perfluoronapthyl--[(perfluorofluorenyl (perfluorophenyl) (perfluoronapthyl) borate]⁻/ (pentamethylcyclopentadienyl) (cyclopentadienyl) zirconium dimethyl; [(isopropyl) (perfluorohexyl) phosphonium]⁺--perfluoroindenyl--[(3,4-difluorophenyl (pentafluorofluorenyl) (perfluoronapthyl)borate]⁻/ (pentamethylcyclopentadienyl) (cyclopentadienyl) zirconium dimethyl; [(methyl(trimethylsilyl)) (2,3,6,7-tetrafluorooctyl)ammonium]⁺--3,4-difluorophenyl--[(tetrafluoronaphthyl(perfluoronapthyl) (perfluorophenyl) borate]⁻/(pentamethylcyclopentadienyl) (cyclopentadienyl) zirconium dimethyl; [(perfluoromethyl) (ethyl(triethylsilyl)) ammonium]⁺--perfluoronapthyl--[(pentafluoronaphthyl (perfluorobiphenyl) (perfluoronapthyl)borate]⁻/ (pentamethylcyclopentadienyl) (cyclopentadienyl) zirconium dimethyl; [(perfluorooctyl) (perfluoroisopropyl) phosphonium]⁺--perfluorophenyl--[bis(perfluorobiphenyl) (2,3,4-trifluorophenyl)borate]⁻/ (pentamethylcyclopentadienyl) (cyclopentadienyl) zirconium dimethyl; [(perfluorooctyl) (octyl)ammonium]⁺--3,4-difluorophenyl--[(2,3,4-trifluorophenyl(2,4-difluorophenyl) (perfluoronapthyl)borate]⁻/(pentamethylcyclopentadienyl) (cyclopentadienyl) zirconium dimethyl; [(perfluoropentyl) (perfluorophenyl)ammonium]⁺--perfluorobiphenyl--[(perfluoronapthyl(perfluorofluorenyl) (2,4-difluorophenyl) borate]⁻/(pentamethylcyclopentadienyl) (cyclopentadienyl) zirconium dimethyl; [(perfluoropropyl) (perfluoroisopentyl) ammonium]⁺--perfluorobiphenyl--[(2,5-difluorophenyl (perfluoronapthyl) (perfluoroindenyl)borate]⁻/ (pentamethylcyclopentadienyl) (cyclopentadienyl) zirconium dimethyl; [(perfluoroisopentyl) (heptyl) phosphonium]⁺--perfluoroindenyl--[(tetrafluoronaphthyl (pentafluorofluorenyl) (perfluoronapthyl)gallinate]⁻/ (pentamethylcyclopentadienyl) (cyclopentadienyl) zirconium dimethyl; [((methyl(triethylsilyl))) (1,6-difluorohexyl) phosphonium]⁺--tetrafluoroindenyl--[(2,5-difluorophenyl (3,4-difluorophenyl) (2,4-difluorophenyl)aluminate]⁻/ (tetramethylcyclopentadienyl) (n-propylcyclopentadienyl) zirconium dimethyl; [(isopropyl) (perfluoroisopropyl) phosphonium]⁺--perfluoronapthyl--[(perfluorophenyl (tetrafluoronaphthyl) (2,3-difluorophenyl)aluminate]⁻/ (tetramethylcyclopentadienyl) (n-propylcyclopentadienyl) zirconium dimethyl; [(1,2-difluorohexyl) (2,3,6,7-tetrafluorooctyl)ammonium]⁺--perfluoroindenyl--[bis(2,5-difluorophenyl) (pentafluoronaphthyl)borate]⁻/ (tetramethylcyclopentadienyl) (n-propylcyclopentadienyl) zirconium dimethyl; [(2,3,6,7-tetrafluorooctyl) (octyl) phosphonium]⁺--perfluorobiphenyl--[(perfluoroindenyl (perfluorobiphenyl) (2,4-difluorophenyl)borate]⁻/ (tetramethylcyclopentadienyl) (n-propylcyclopentadienyl) zirconium dimethyl; [(2,3,6,7-tetrafluorooctyl) (perfluoropropyl) phosphonium]⁺--pentafluoronaphthyl--[bis(tetrafluoroindenyl) (pentafluoronaphthyl)borate]⁻/ (tetramethylcyclopentadienyl) (n-propylcyclopentadienyl) zirconium dimethyl; [(3-methylpentyl) (isopropyl) phosphonium]⁺--2,4-difluorophenyl--[(2,3-difluorophenyl (perfluorofluorenyl) (perfluorobiphenyl)borate]⁻/ (tetramethylcyclopentadienyl) (n-propylcyclopentadienyl) zirconium dimethyl; [(3-methylpentyl) (ethyl (trimethylsilyl))ammonium]⁺--perfluorofluorenyl--[(perfluorophenyl(pentafluoronaphthyl) (perfluoroindenyl)borate]⁻/(tetramethylcyclopentadienyl) (n-propylcyclopentadienyl) zirconium dimethyl; [(ethyl (trimethylsilyl)) (3-methylpentyl)ammonium]⁺--2,4-difluorophenyl--[(2,3,4-trifluorophenyl(perfluorobiphenyl) (perfluoronapthyl)borate]⁻/(tetramethylcyclopentadienyl) (n-propylcyclopentadienyl) zirconium dimethyl; [(isopentyl) (ethyl(trimethylsilyl))ammonium]⁺--perfluoropyrenyl--[(pentafluorofluorenyl(perfluoroindenyl) (perfluorophenyl)borate]⁻/(tetramethylcyclopentadienyl) (n-propylcyclopentadienyl) zirconium dimethyl; [(methyl (trimethylsilyl)) (heptyl) phosphonium]⁺--perfluoronapthyl--[(2,4-difluorophenyl(perfluorobiphenyl) (2,5-difluorophenyl)borate]⁻/(tetramethylcyclopentadienyl) (n-propylcyclopentadienyl) zirconium dimethyl; [(pentyl) (perfluorohexyl)ammonium]⁺--perfluorophenyl--[(perfluorophenyl(perfluorobiphenyl) (perfluoroindenyl) borate]⁻/(tetramethylcyclopentadienyl) (n-propylcyclopentadienyl) zirconium dimethyl; [(perfluoroisopentyl) (hexyl)ammonium]⁺--perfluorophenyl--[bis(2,3,4-trifluorophenyl) (tetrafluoroindenyl)borate]⁻/(tetramethylcyclopentadienyl) (n-propylcyclopentadienyl) zirconium dimethyl; [(perfluoro-t-butyl) (perfluoropropyl)ammonium]⁺--perfluorobiphenyl--[(3,4-difluorophenyl(perfluorobiphenyl) (tetrafluoroindenyl)borate]⁻/(tetramethylcyclopentadienyl) (n-propylcyclopentadienyl) zirconium dimethyl; bis(t-butyl)ammonium]⁺-perfluoropyrenyl--[(perfluorobiphenyl (perfluorofluorenyl) (perfluorofluorenyl)borate]⁻/ (tetramethylcyclopentadienyl) (n-propylcyclopentadienyl) zirconium dimethyl; [(1,2-difluorohexyl) (perfluoroisopentyl)ammonium]⁺--perfluorofluorenyl--[(pentafluorofluorenyl(perfluorophenyl) (2,3,4-trifluorophenyl)aluminate]⁻/bis(1,3-dibutyl-methyl-cyclopentadienyl) zirconium dimethyl; [(2,3,6,7-tetrafluorooctyl) (perfluoro-t-butyl)ammonium]⁺--tetrafluoroindenyl--[(2,4-difluorophenyl(perfluoronapthyl) (perfluorophenyl)aluminate]⁻/bis(1,3-dibutyl-methyl-cyclopentadienyl) zirconium dimethyl; [(methyl (trimethylsilyl)) (1,2-difluorohexyl)ammonium]⁺--perfluoroindenyl--[(2,3,5-trifluorophenyl (tetrafluoronaphthyl) (trifluoroindenyl)aluminate]⁻/bis(1,3-dibutyl-methylcyclopentadienyl) zirconium dimethyl; [(pentyl) (3-methylpentyl)ammonium]⁺--2,3,4-trifluorophenyl--[bis(perfluoroindenyl) (perfluoronapthyl) aluminate]⁻/bis(1,3-dibutyl-methyl-cyclopentadienyl) zirconium dimethyl; [(perfluorophenyl) (perfluoroethyl) ammonium]⁺--perfluorobiphenyl--[(2,4-difluorophenyl (perfluoroindenyl) (3,4-difluorophenyl)aluminate]⁻/bis(1,3-dibutyl-methylcyclopentadienyl) zirconium dimethyl; [(1,2-difluorohexyl) (1,6-difluorohexyl)ammonium]⁺--perfluoronapthyl--[tris(perfluoroindenyl)borate]⁻/bis(1,3-dibutyl-methyl-cyclopentadienyl) zirconium dimethyl; [(2,3,6,7-tetrafluorooctyl) (perfluorohexyl)ammonium]⁺--tetrafluoronaphthyl--[(perfluoropyrenyl(perfluorobiphenyl) (perfluoronapthyl)borate]⁻/bis(1,3-dibutyl-methylcyclopentadienyl) zirconium dimethyl; [(ethyl) (ethyl (trimethylsilyl))ammonium]⁺--perfluorophenyl--[(pentafluoronaphthyl(tetrafluoronaphthyl) (perfluorofluorenyl)borate]⁻/bis(1,3-dibutyl-methylcyclopentadienyl) zirconium dimethyl; [(isohexyl) (phenyl)ammonium]⁺--2,3-difluorophenyl--[bis (perfluoroindenyl) (3,4-difluorophenyl)borate]⁻/bis(1,3-dibutyl-methyl-cyclopentadienyl) zirconium dimethyl; [(isohexyl) (perfluorophenyl)ammonium]⁺--perfluorofluorenyl--[(2,3,4-trifluorophenyl (pentafluoronaphthyl) (perfluoronapthyl)borate]⁻/bis(1,3-dibutyl-methylcyclopentadienyl) zirconium dimethyl; [(perfluorohexyl) (heptyl)ammonium]⁺--tetrafluoroindenyl--[bis(perfluoroindenyl) (perfluorofluorenyl)borate]⁻/bis(1,3-dibutyl-methyl-cyclopentadienyl) zirconium dimethyl; [(perfluoroisopentyl)

(isohexyl) phosphonium]⁺--tetrafluoronaphthyl--[(perfluorobiphenyl(2,3,4-trifluorophenyl)(perfluoroindenyl)borate]⁻/bis(1,3-dibutyl-methylcyclopentadienyl) zirconium dimethyl; [(phenyl)(ethyl(triethylsilyl))ammonium]⁺--perfluoronapthyl--[bis(perfluorophenyl) (perfluoroindenyl)borate]⁻/bis(1,3-dibutyl-methyl-cyclopentadienyl) zirconium dimethyl; [(isohexyl) (t-butyl) phosphonium]⁺--pentafluorofluorenyl--[(tetrafluoronaphthyl(pentafluoronaphthyl)(perfluorobiphenyl)gallinate]⁻/bis(1,3-dibutyl-methylcyclopentadienyl) zirconium dimethyl; [(pentyl)(t-butyl) phosphonium]⁺--perfluorofluorenyl--[(perfluoronapthyl(trifluoroindenyl) (perfluoroindenyl)gallinate]⁻/bis(1,3-dibutyl-methylcyclopentadienyl) zirconium dimethyl; [(perfluorophenyl) (perfluorooctyl) ammonium]⁺--perfluorofluorenyl-[(tetrafluoronaphthyl(tetrafluoroindenyl) (perfluoroindenyl)gallinate]⁻/bis(1,3-dibutyl-methyl-cyclopentadienyl) zirconium dimethyl; [(t-butyl) (2,3,5-trifluorophenyl) phosphonium]⁺--perfluoronapthyl--[(perfluorofluorenyl(perfluoronapthyl)(perfluoroindenyl)gallinate]⁻/bis(1,3-dibutylmethyl-cyclopentadienyl) zirconium dimethyl; (bis((methyl(triethylsilyl))) phosphonium]⁺--trifluoroindenyl--[(perfluoroindenyl(perfluorophenyl) (3,4-difluorophenyl)aluminate]⁻/bis(4-trisethylsilyl)methyl (cyclopentadienyl) (2,7-di-t-butylfluorenyl) hafnium dimethyl [((methyl(triethylsilyl))) (perfluorohexyl)ammonium]⁺--tetrafluoroindenyl--[(perfluorobiphenyl(perfluorophenyl)(tetrafluoronaphthyl)borate]⁻/bis(4-trisethylsilyl)methyl (cyclopentadienyl) (2,7-di-t-butylfluorenyl) hafnium dimethyl ; [((methyl(triethylsilyl))) (isopentyl)ammonium]⁺--perfluorophenyl--[(perfluoronapthyl(perfluorobiphenyl)(2,3,5-trifluorophenyl)borate]⁻/bis(4-trisethylsilyl)methyl (cyclopentadienyl) (2,7-di-t-butylfluorenyl) hafnium dimethyl ; [((methyl(triethylsilyl))) (perfluorohexyl) ammonium]⁺--2,3,4-trifluorophenyl--[(perfluorofluorenyl (perfluorobiphenyl) (perfluorophenyl)borate]⁻/bis(4-trisethylsilyl)methyl (cyclopentadienyl) (2,7-di-t-butylfluorenyl) hafnium dimethyl; [(1,2-difluorohexyl) (isopropyl)ammonium]⁺--3,4-difluorophenyl--[(perfluorofluorenyl(2,3-difluorophenyl)(tetrafluoronaphthyl)borate]⁻/bis(4-trisethylsilyl)methyl (cyclopentadienyl) (2,7-di-t-butylfluorenyl) hafnium dimethyl; [(2,3,4,5-tetrafluorophenyl) (isohexyl)ammonium]⁺--2,3-difluorophenyl--[(2,3,4-trifluorophenyl(3,4-difluorophenyl) (tetrafluoronaphthyl)borate]⁻/bis(4-trisethylsilyl)methyl (cyclopentadienyl) (2,7-di-t-butylfluorenyl) hafnium dimethyl; (bis(2,3,6,7-tetrafluorooctyl)ammonium]⁺--perfluorobiphenyl--[(perfluorophenyl(3,4-difluorophenyl) (perfluoropyrenyl)borate]⁻/bis(4-trisethylsilyl)methyl (cyclopentadienyl) (2,7-di-t-butylfluorenyl) hafnium dimethyl; [(3-methylpentyl)(ethyl)ammonium]⁺--2,3-difluorophenyl--[(2,4-difluorophenyl(perfluoroindenyl) (perfluorophenyl)borate]⁻/bis(4-trisethylsilyl)methyl (cyclopentadienyl) (2,7-di-t-butylfluorenyl) hafnium dimethyl; [(3-methylpentyl)(propyl)arsonium]⁺--perfluoropyrenyl--[(perfluorobiphenyl(perfluorofluorenyl) (2,3,4-trifluorophenyl)borate]⁻/bis(4-trisethylsilyl)methyl (cyclopentadienyl) (2,7-di-t-butylfluorenyl) hafnium dimethyl; [(perfluoromethyl)(octyl)ammonium]⁺--perfluoronapthyl--[(perfluoronapthyl (perfluorobiphenyl) (perfluorofluorenyl)borate]⁻/bis(4-trisethylsilyl)methyl (cyclopentadienyl) (2,7-di-t-butylfluorenyl) hafnium dimethyl; [(phenyl)(perfluoroisopentyl)ammonium]⁺--perfluoroindenyl--[(tetrafluoroindenyl(3,4-difluorophenyl) (perfluoroindenyl)borate]⁻/bis(4-trisethylsilyl)methyl (cyclopentadienyl) (2,7-di-t-butylfluorenyl) hafnium dimethyl; [(ethyl(triethylsilyl))(1,2-difluorohexyl) phosphonium]⁺--perfluorobiphenyl--[(2,5-difluorophenyl(tetrafluoronaphthyl) (perfluoropyrenyl)gallinate]⁻/bis(4-trisethylsilyl)methyl (cyclopentadienyl) (2,7-di-t-butylfluorenyl) hafnium dimethyl; [(methyl) (methyl(trimethylsilyl))arsonium]⁺--perfluorofluorenyl--[(2,3,5-trifluorophenyl (perfluoronapthyl) (perfluorophenyl)gallinate]⁻/bis(4-trisethylsilyl)methyl (cyclopentadienyl) (2,7-di-t-butylfluorenyl) hafnium dimethyl; [(butyl) ((methyl(triethylsilyl)))ammonium]⁺--perfluoroindenyl--[(perfluorobiphenyl(perfluorofluorenyl).(tetrafluoronaphthyl)aluminate]⁻/bis(4-trisethylsilyl)methyl (cyclopentadienyl) (fluorenyl) hafnium dimethyl; [(ethyl (triethylsilyl)) (pentyl)ammonium]⁺--perfluoronapthyl--[(perfluorophenyl(2,4-difluorophenyl) (perfluoronapthyl)aluminate]⁻/bis(4-trisethylsilyl)methyl (cyclopentadienyl) (fluorenyl) hafnium dimethyl [(methyl(trimethylsilyl))(t-butyl) phosphonium]⁺--trifluoroindenyl--[(perfluorophenyl(perfluorofluorenyl) (perfluoroindenyl)aluminate]⁻/bis(4-trisethylsilyl)methyl (cyclopentadienyl) (fluorenyl) hafnium dimethyl ; [(perfluoromethyl) (ethyl (triethylsilyl)) phosphonium]⁺--perfluoronapthyl--[(perfluorophenyl(perfluorofluorenyl) (trifluoroindenyl)aluminate]⁻/bis(4-trisethylsilyl)methyl (cyclopentadienyl) (fluorenyl) hafnium dimethyl; i(perfluoro-t-butyl) (pentyl) ammonium]⁺--perfluorobiphenyl--[bis(perfluorofluorenyl)(perfluorobiphenyl)aluminate]⁻/bis(4-trisethylsilyl)methyl (cyclopentadienyl) (fluorenyl) hafnium dimethyl; [(1,2-difluorohexyl) (perfluoromethyl)ammonium]⁺--tetrafluoroindenyl--[(perfluorofluorenyl(perfluorophenyl) (perfluoropyrenyl)borate]⁻/bis(4-trisethylsilyl)methyl (cyclopentadienyl) (fluorenyl) hafnium dimethyl; [(2,3,4,5-tetrafluorophenyl) (perfluoropentyl)ammonium]⁺--pentafluoronaphthyl--[(perfluoroindenyl(2,3-difluorophenyl) (tetrafluoroindenyl)borate]⁻/bis(4-trisethylsilyl)methyl (cyclopentadienyl) (fluorenyl) hafnium dimethyl; [(isohexyl) (t-butyl)ammonium]⁺--tetrafluoronaphthyl--[(pentafluorofluorenyl (perfluorobiphenyl) (2,3-difluorophenyl)borate]⁻/bis(4-trisethylsilyl)methyl (cyclopentadienyl) (fluorenyl) hafnium dimethyl; [(isopentyl) (isopropyl)ammonium]⁺--2,4-difluorophenyl--[(pentafluorofluorenyl(2,5-difluorophenyl) (perfluorofluorenyl)borate]⁻/bis(4-trisethylsilyl)methyl (cyclopentadienyl) (fluorenyl) hafnium dimethyl; [(pentyl) (1,2-difluorohexyl)ammonium]⁺--perfluorofluorenyl--[bis (perfluoroindenyl) (trifluoroindenyl)borate]⁻/bis(4-trisethylsilyl)methyl (cyclopentadienyl) (fluorenyl) hafnium dimethyl; (bis(perfluoroethyl)ammonium]⁺--perfluorobiphenyl--[(perfluoroindenyl(perfluorofluorenyl)(perfluoronapthyl)borate]⁻/bis(4-trisethylsilyl)methyl (cyclopentadienyl) (fluorenyl) hafnium dimethyl [(perfluorohexyl) ((methyl(triethylsilyl))) phosphonium]⁺--2,4-difluorophenyl--[(2,3,5-trifluorophenyl (perfluorophenyl) (2,3,4-trifluorophenyl)borate]⁻/bis(4-trisethylsilyl)methyl (cyclopentadienyl) (fluorenyl) hafnium dimethyl; [(perfluoromethyl) (propyl)ammonium]⁺--2,3,5-trifluorophenyl--[bis(perfluoronapthyl) (trifluoroindenyl)borate]⁻/bis(4-trisethylsilyl)methyl (cyclopentadienyl) (fluorenyl) hafnium dimethyl; [(perfluoropropyl) (ethyl (trimethylsilyl))ammonium]⁺--perfluorophenyl--[(2,3,4-trifluorophenyl(perfluorofluorenyl) (perfluorophenyl)borate]⁻/bis(4-trisethylsilyl)methyl (cyclopentadienyl) (fluorenyl) hafnium dimethyl; [(pentyl) (3-methylpentyl)ammonium]⁺--perfluorobiphenyl--[bis(perfluorophenyl)(pentafluorofluorenyl)gallinate]⁻/bis(4-trisethylsilyl)methyl (cyclopentadienyl) (fluorenyl) hafnium dimethyl;

[(perfluorobutyl) (octyl)ammonium]⁺--tetrafluoronaphthyl--[bis(perfluoroindenyl) (tetrafluoronaphthyl)aluminate]⁻/bis(hexamethyl disilazido) titanium dimethyl; [(ethyl (trimethylsilyl)) (heptyl)ammonium]⁺--perfluorobiphenyl--[(pentafluoronaphthyl(tetrafluoronaphthyl) (2,4-difluorophenyl)borate]⁻/bis(hexamethyl disilazido) titanium dimethyl; [(isohexyl) (butyl)ammonium]⁺--pentafluorofluorenyl--[bis(perfluorophenyl) (3,4-difluorophenyl)borate]⁻/bis(hexamethyl disilazido) titanium dimethyl; [(isohexyl) (hexyl)ammonium]⁺--perfluorofluorenyl-[(perfluoronapthyl(perfluorofluorenyl) (tetrafluoronaphthyl)borate]⁻/bis(hexamethyl disilazido) titanium dimethyl; [(perfluorohexyl) (isohexyl)ammonium]⁺--perfluoropyrenyl--[(perfluorophenyl (perfluorobiphenyl) (pentafluoronaphthyl)borate]⁻/bis(hexamethyl disilazido) titanium dimethyl; [(perfluoroisopropyl) (ethyl(triethylsilyl)) phosphonium]⁺--perfluoropyrenyl--[bis(perfluorophenyl) (perfluoroindenyl)borate]⁻/bis(hexamethyl disilazido) titanium dimethyl; [(perfluorophenyl) (ethyl(trimethylsilyl))ammonium]⁺--pentafluorofluorenyl--[(tetrafluoroindenyl(2,3,5-trifluorophenyl) (perfluoronapthyl)borate]⁻/bis(hexamethyl disilazido) titanium dimethyl; [(propyl) (perfluoropropyl)ammonium]⁺--2,3,5-trifluorophenyl--[(2,3,4-trifluorophenyl(perfluorobiphenyl) (tetrafluoroindenyl)borate]⁻/bis(hexamethyl disilazido) titanium dimethyl; [(isopentyl) (isopropyl)ammonium]⁺--perfluorofluorenyl--[(perfluorobiphenyl(perfluoroindenyl) (perfluoropyrenyl)gallinate]⁻/bis(hexamethyl disilazido) titanium dimethyl; [(perfluoroethyl) (hexyl)ammonium]⁺--perfluoroindenyl--[(pentafluorofluorenyl(2,4-difluorophenyl) (perfluorobiphenyl)aluminate]⁻/dimethylsily (bisindenyl) zirconium dichloride; [(perfluoroethyl) (perfluoromethyl)ammonium]⁺--tetrafluoroindenyl--[(perfluorofluorenyl (perfluorobiphenyl) (perfluoronapthyl)aluminate]⁻/dimethylsily (bisindenyl) zirconium dichloride; [(perfluoropropyl) (methyl(trimethylsilyl))ammonium]⁺--perfluorophenyl--[(perfluoronapthyl(2,4-difluorophenyl) (3,4-difluorophenyl)aluminate]⁻/dimethylsily (bisindenyl) zirconium dichloride; [((methyl(triethylsilyl))) (methyl (trimethylsilyl))ammonium]⁺--perfluorobiphenyl--[(perfluoronapthyl(2,3,4-trifluorophenyl) (trifluoroindenyl)borate]⁻/dimethylsily (bisindenyl) zirconium dichloride; [(2,3,4,5-tetrafluorophenyl) (perfluorohexyl) phosphonium]⁺--2,3-difluorophenyl--[bis(perfluoroindenyl) (perfluorofluorenyl)borate]⁻/dimethylsily (bisindenyl) zirconium dichloride; [(butyl) ((methyl(triethylsilyl)))ammonium]⁺--perfluorophenyl--[(pentafluorofluorenyl (perfluorofluorenyl) (perfluorophenyl)borate]⁻/dimethylsily (bisindenyl) zirconium dichloride; [(ethyl(trimethylsilyl)) (phenyl)ammonium]⁺-perfluorofluorenyl--[bis(perfluorobiphenyl) (perfluoropyrenyl)borate]⁻/dimethylsily (bisindenyl) zirconium dichloride; [(perfluorohexyl) (octyl)ammonium]⁺--perfluorofluorenyl--[(2,5-difluorophenyl (perfluoronapthyl) (perfluorobiphenyl)borate]⁻/dimethylsily (bisindenyl) zirconium dichloride; [(perfluorooctyl) (2,3,6,7-tetrafluorooctyl)ammonium]⁺--tetrafluoroindenyl--[(perfluoroindenyl(perfluorobiphenyl) (perfluoronapthyl)borate]⁻/dimethylsily (bisindenyl) zirconium dichloride; [(perfluorophenyl) (1,2-difluorohexyl)ammonium]⁺--2,3,4-trifluorophenyl--[(perfluorobiphenyl(perfluorofluorenyl) (perfluorophenyl)borate]⁻/dimethylsily (bisindenyl) zirconium dichloride; [(perfluoro-t-butyl) (perfluoroethyl)ammonium]⁺--2,3,5-trifluorophenyl--[(2,4-difluorophenyl (tetrafluoronaphthyl) (perfluorofluorenyl)borate]⁻/dimethylsily (bisindenyl) zirconium dichloride; [(perfluoromethyl) (perfluoro-t-butyl)ammonium]⁺--perfluoronapthyl--[(perfluoroindenyl(perfluorobiphenyl) (perfluoronapthyl)gallinate]⁻/dimethylsily (bisindenyl) zirconium dichloride; [(isohexyl) (isopropyl)ammonium]⁺--trifluoroindenyl--[(perfluorophenyl(pentafluoronaphthyl) (perfluoropyrenyl)aluminate]⁻/dimethylsilybisindenyl hafnium dimethyl; [(octyl) (perfluoropentyl)arsonium]⁺--perfluoronapthyl--[(tetrafluoronaphthyl(2,3-difluorophenyl) (pentafluoronaphthyl)aluminate]⁻/dimethylsily-bisindenyl hafnium dimethyl; [(ethyl(triethylsilyl)) (pentyl) phosphonium]⁺--2,3,4-trifluorophenyl--[(perfluorophenyl (2,3,5-trifluorophenyl) (perfluorofluorenyl)borate]⁻/dimethylsily-bisindenyl hafnium dimethyl; [(methyl (trimethylsilyl)) (ethyl) phosphonium]⁺--perfluorobiphenyl--[(perfluorophenyl(perfluoroindenyl) (2,3-difluorophenyl)borate]⁻/dimethylsily-bisindenyl hafnium dimethyl; [(propyl) (methyl)arsonium]⁺--perfluoropyrenyl--[(perfluoronapthyl(perfluorofluorenyl) (pentafluorofluorenyl)borate]⁻/dimethylsily-bisindenyl hafnium dimethyl; (bis(isohexyl)ammonium]⁺--perfluorofluorenyl--[bis(perfluorofluorenyl) (trifluoroindenyl)gallinate]⁻/dimethylsily-bisindenyl hafnium dimethyl; [(butyl) (perfluoroisopropyl)ammonium]⁺--perfluorophenyl--[(3,4-difluorophenyl (pentafluoronaphthyl)) (perfluoropyrenyl)aluminate]⁻/dimethylsilyl (tetramethylcyclopentadienyl) (adamantyl-1-amino) titanium dimethyl; [(isohexyl) (perfluorohexyl)ammonium]⁺--2,3,4-trifluorophenyl--[(perfluoronapthyl(2,4-difluorophenyl) (tetrafluoronaphthyl)aluminate]⁻/dimethylsilyl (tetramethylcyclopentadienyl) (adamantyl-1-amino) titanium dimethyl; [(isopentyl) (ethyl)arsonium]⁺--tetrafluoroindenyl--[(trifluoroindenyl(perfluorofluorenyl) (tetrafluoronaphthyl)aluminate]⁻/dimethylsilyl (tetramethylcyclopentadienyl) (adamantyl-1-amino) titanium dimethyl; [(perfluoroisopentyl) (ethyl(trimethylsilyl))ammonium]⁺--pentafluoronaphthyl--[bis(perfluoroindenyl) (pentafluoronaphthyl)aluminate]⁻/dimethylsilyl (tetramethylcyclopentadienyl) (adamantyl-1-amino) titanium dimethyl; [(perfluoroisopropyl) (3-methylpentyl)arsonium]⁺--pentafluoronaphthyl--[bis(perfluorophenyl) (perfluorofluorenyl)aluminate]⁻/dimethylsilyl (tetramethylcyclopentadienyl) (adamantyl-1-amino) titanium dimethyl; [(2,3,6,7-tetrafluorooctyl) (3-methylpentyl)ammonium]⁺--pentafluorofluorenyl--[(perfluorofluorenyl (pentafluoronaphthyl) (tetrafluoroindenyl)borate]⁻/dimethylsilyl (tetramethylcyclopentadienyl) (adamantyl-1-amino) titanium dimethyl; [(hexyl) (perfluoromethyl)ammonium]⁺--pentafluorofluorenyl--[(tetrafluoronaphthyl (perfluorobiphenyl) (pentafluorofluorenyl)borate]⁻/dimethylsilyl (tetramethylcyclopentadienyl) (adamantyl-1-amino) titanium dimethyl; [(methyl) (butyl)ammonium]⁺--2,3,5-trifluorophenyl--[(perfluorofluorenyl (perfluoronapthyl) (tetrafluoronaphthyl)borate]⁻/dimethylsilyl (tetramethylcyclopentadienyl) (adamantyl-1-amino) titanium dimethyl; [(methyl(trimethylsilyl)) (octyl)ammonium]⁺--2,5-difluorophenyl--[(perfluoroindenyl (perfluoronapthyl) (perfluorobiphenyl)borate]⁻/dimethylsilyl (tetramethylcyclopentadienyl) (adamantyl-1-amino) titanium dimethyl; [(octyl) (propyl)ammonium]⁺--perfluoroindenyl--[bis(perfluorophenyl) (trifluoroindenyl)borate]⁻/dimethylsilyl (tetramethylcyclopentadienyl) (adamantyl-1-amino) titanium dimethyl; [(perfluoroethyl) (perfluoroheptyl) phosphonium]⁺--2,3,5-trifluorophenyl--[(perfluoroindenyl(perfluorofluorenyl) (perfluorobiphenyl)borate]⁻/dimethylsilyl (tetramethylcyclopentadienyl) (adamantyl-1-amino) titanium dimethyl; [(perfluoromethyl) (ethyl(trimethylsilyl))ammonium]⁺--perfluorophenyl--(perfluoronapthyl(perfluoroindenyl) (tetrafluoronaphthyl)

borate]⁻/dimethylsilyl (tetramethylcyclopentadienyl) (adamantyl-1-amino) titanium dimethyl; [(perfluorophenyl) (ethyl(triethylsilyl))ammonium]⁺--trifluoroindenyl--[(perfluoronapthyl(perfluoroindenyl) (perfluorophenyl) borate]⁻/dimethylsilyl (tetramethylcyclopentadienyl) (adamantyl-1-amino) titanium dimethyl; [(t-butyl) (3-methylpentyl) phosphonium]⁺--perfluorophenyl--[bis (perfluorofluorenyl) (2,5-difluorophenyl)borate]⁻/ dimethylsilyl (tetramethylcyclopentadienyl) (adamantyl-1-amino) titanium dimethyl; [(methyl(triethylsilyl)) (butyl) ammonium]⁺--perfluoroindenyl--[(perfluorofluorenyl) (perfluoronapthyl) (2,3,5-trifluorophenyl)gallinate]⁻/ dimethylsilyl (tetramethylcyclopentadienyl) (adamantyl-1-amino) titanium dimethyl; [(ethyl(triethylsilyl)) (heptyl) phosphonium]⁺--tetrafluoronaphthyl--[bis (perfluorobiphenyl) (perfluoronapthyl)aluminate]⁻/ dimethylsilyl (tetramethylcyclopentadienyl) t-butyl-amino) titanium dimethyl; [(pentyl) (perfluoromethyl) ammonium]⁺--perfluorobiphenyl--[(trifluoroindenyl (perfluoronapthyl) (perfluorofluorenyl)aluminate]⁻/ dimethylsilyl (tetramethylcyclopentadienyl) t-butyl-amino) titanium dimethyl; [(perfluorobutyl) (perfluoropropyl) ammonium]⁺--perfluorofluorenyl--[(perfluorofluorenyl (perfluorophenyl) (perfluorobiphenyl)aluminate]⁻/ dimethylsilyl (tetramethylcyclopentadienyl) t-butyl-amino) titanium dimethyl; [(perfluoropentyl) (perfluoromethyl) ammonium]⁺--tetrafluoroindenyl--[bis(2,4-difluorophenyl) (pentafluorofluorenyl)aluminate]⁻/dimethylsilyl (tetramethylcyclopentadienyl) t-butyl-amino) titanium dimethyl; [(ethyl(triethylsilyl)) (hexyl) phosphonium]⁺-pentafluoronaphthyl--[bis(trifluoroindenyl) (perfluoronapthyl)borate]⁻/dimethylsilyl (tetramethylcyclopentadienyl) t-butyl-amino) titanium dimethyl; [(heptyl) (2,3,6,7-tetrafluorooctyl)ammonium]⁺--perfluoronapthyl--[(perfluorofluorenyl(perfluorophenyl) (2,3,4-trifluorophenyl)borate]⁻/dimethylsilyl (tetramethylcyclopentadienyl) t-butyl-amino) titanium dimethyl; [(isohexyl) (1,6-difluorohexyl)ammonium]⁺--perfluoroindenyl--[(tetrafluoronaphthyl(perfluoronapthyl) (perfluoropyrenyl)borate]⁻/dimethylsilyl (tetramethylcyclopentadienyl) t-butyl-amino) titanium dimethyl; [(isopentyl) (1,6-difluorohexyl)ammonium]⁺--2,3,4-trifluorophenyl--[(2,5-difluorophenyl(perfluoronapthyl) (2,4-difluorophenyl)borate]⁻/dimethylsilyl (tetramethylcyclopentadienyl) t-butyl-amino) titanium dimethyl; [(octyl) (isohexyl)ammonium]⁺--pentafluoronaphthyl--[(perfluoronapthyl(trifluoroindenyl) (2,5-difluorophenyl)borate]⁻/dimethylsilyl (tetramethylcyclopentadienyl) t-butyl-amino) titanium dimethyl;

[(perfluoroheptyl) (ethyl(trimethylsilyl))ammonium]⁺--perfluorobiphenyl--[(3,4-difluorophenyl(2,5-difluorophenyl) (2,3-difluorophenyl)borate]⁻/dimethylsilyl (tetramethylcyclopentadienyl) t-butyl-amino) titanium dimethyl; [(perfluoromethyl) (perfluoropropyl)ammonium]⁺--perfluoroindenyl--[(perfluorophenyl(perfluoronapthyl) (pentafluorofluorenyl)borate]⁻/dimethylsilyl (tetramethylcyclopentadienyl) t-butyl-amino) titanium dimethyl; (bis(t-butyl)ammonium]⁺--pentafluoronaphthyl--[bis (perfluorobiphenyl) (perfluorophenyl)borate]⁻/dimethylsilyl (tetramethylcyclopentadienyl) t-butyl-amino) titanium dimethyl; (bis(butyl)ammonium]⁺--perfluorobiphenyl--[(perfluoronapthyl(perfluorophenyl) (2,4-difluorophenyl) aluminate]⁻/dimethylsilyl bis(methylindenyl) hafnium dimethyl; [(ethyl(trimethylsilyl)) (heptyl) phosphonium]⁺-- tetrafluoroindenyl--[(perfluorofluorenyl(2,5-difluorophenyl) (perfluoronapthyl)aluminate]⁻/dimethylsilyl bis (methylindenyl) hafnium dimethyl; (bis((methyl (triethylsilyl))) phosphonium]⁺--pentafluorofluorenyl--[(perfluoroindenyl(2,3,4-trifluorophenyl) (pentafluorofluorenyl)borate]⁻/dimethylsilyl bis (methylindenyl) hafnium dimethyl; [(1,6-difluorohexyl) (isopentyl)ammonium]⁺--2,4-difluorophenyl--[(perfluorophenyl(perfluoronapthyl) (pentafluoronaphthyl) borate]⁻/dimethylsilyl bis(methylindenyl) hafnium dimethyl; [(2,3,4,5-tetrafluorophenyl) (butyl) phosphonium]⁺--perfluorobiphenyl--[(2,5-difluorophenyl(perfluorobiphenyl) (perfluorofluorenyl)borate]⁻/dimethylsilyl bis (methylindenyl) hafnium dimethyl; [(ethyl(trimethylsilyl)) (perfluoroisopropyl) phosphonium]⁺--2,5-difluorophenyl--[(perfluoroindenyl(perfluorofluorenyl) (perfluorobiphenyl) borate]⁻/dimethylsilyl bis(methylindenyl) hafnium dimethyl; [(methyl(trimethylsilyl)) (perfluorobutyl) ammonium]⁺--2,3,4-trifluorophenyl--[bis(perfluoroindenyl) (2,4-difluorophenyl)borate]⁻/dimethylsilyl bis (methylindenyl) hafnium dimethyl; [(octyl) (perfluoromethyl)ammonium]⁺--perfluoronapthyl--[bis (perfluoronapthyl) (2,3,5-trifluorophenyl)borate]⁻/ dimethylsilyl bis(methylindenyl) hafnium dimethyl; [(perfluoromethyl) (methyl(trimethylsilyl))ammonium]⁺--perfluorobiphenyl--[(perfluorofluorenyl(perfluorobiphenyl) (perfluorophenyl)borate]⁻/dimethylsilyl bis(methylindenyl) hafnium dimethyl; [(perfluoromethyl) (isopentyl) ammonium]⁺--tetrafluoronaphthyl--[bis(perfluorofluorenyl) (3,4-difluorophenyl)borate]⁻/dimethylsilyl bis (methylindenyl) hafnium dimethyl; [(perfluorooctyl) (3-methylpentyl) phosphonium]⁺--perfluorofluorenyl--[(perfluoroindenyl(perfluorofluorenyl) (perfluoropyrenyl) borate]⁻/dimethylsilyl bis(methylindenyl) hafnium dimethyl; [(perfluoroisopentyl) (ethyl(triethylsilyl)) ammonium]⁺--perfluoroindenyl--[(3,4-difluorophenyl (tetrafluoroindenyl) (pentafluoronaphthyl)gallinate]⁻/ dimethylsilyl bis(methylindenyl) hafnium dimethyl; [(perfluoromethyl) (ethyl)arsonium]⁺--2,3,5-trifluorophenyl--[bis(perfluorofluorenyl) (perfluoronapthyl) gallinate]⁻/dimethylsilyl bis(methylindenyl) hafnium dimethyl; [(t-butyl) (ethyl(trimethylsilyl)) phosphonium]⁺--perfluorobiphenyl--[(trifluoroindenyl(3,4-difluorophenyl) (perfluoroindenyl)gallinate]⁻/dimethylsilyl bis (methylindenyl) hafnium dimethyl; [(perfluoroethyl) (2,3,6, 7-tetrafluorooctyl)ammonium]⁺--trifluoroindenyl--[(perfluoronapthyl(perfluorofluorenyl) (trifluoroindenyl) aluminate]⁻/dimethylsilyl bis(naphthylmethylindenyl) hafnium dimethyl; [(perfluorooctyl) (3-methylpentyl) ammonium]⁺--pentafluorofluorenyl--[(perfluoroindenyl(2, 3,4-trifluorophenyl) (tetrafluoronaphthyl)aluminate]⁻/ dimethylsilyl bis(naphthylmethylindenyl) hafnium dimethyl; [((methyl(triethylsilyl))) (perfluoroisopropyl) ammonium]⁺--trifluoroindenyl--[(perfluorophenyl(2,3,5-trifluorophenyl) (tetrafluoroindenyl)borate]⁻/dimethylsilyl bis(naphthylmethylindenyl) hafnium dimethyl; [(1,6-difluorohexyl) (methyl(triethylsilyl))ammonium]⁺--perfluorobiphenyl--[(2,3-difluorophenyl(perfluorobiphenyl) (tetrafluoroindenyl)borate]⁻/dimethylsilyl bis (naphthylmethylindenyl) hafnium dimethyl; [(2,3,6,7-tetrafluorooctyl) (heptyl)ammonium]⁺--perfluoronapthyl--[(perfluorofluorenyl(perfluoronapthyl) (tetrafluoroindenyl) borate]⁻/dimethylsilyl bis(naphthylmethylindenyl) hafnium dimethyl; [(ethyl(trimethylsilyl)) (perfluoroisopropyl) ammonium]⁺--perfluoroindenyl--[(pentafluoronaphthyl(2,3, 4-trifluorophenyl) (perfluorophenyl)borate]⁻/dimethylsilyl bis(naphthylmethylindenyl) hafnium dimethyl; [(methyl (triethylsilyl)) (methyl) phosphonium]⁺--perfluorophenyl--[(2,3-difluorophenyl(2,5-difluorophenyl) (2,4- difluorophenyl)borate]⁻/dimethylsilyl bis (naphthylmethylindenyl) hafnium dimethyl; [(perfluoromethyl) (phenyl)ammonium]⁺--perfluoroindenyl--[(trifluoroindenyl(2,4-difluorophenyl) (perfluoroindenyl)borate]⁻/dimethylsilyl bis (naphthylmethylindenyl) hafnium dimethyl; [(perfluoromethyl) (perfluorooctyl)arsonium]⁺--2,3,5-trifluorophenyl--[(perfluoronapthyl(tetrafluoronaphthyl) (perfluorofluorenyl)borate]⁻/dimethylsilyl bis (naphthylmethylindenyl) hafnium dimethyl; [(perfluoromethyl) (t-butyl)ammonium]⁺--perfluoronapthyl--[(perfluorophenyl(perfluoroindenyl) (perfluorobiphenyl)borate]⁻/dimethylsilyl bis (naphthylmethylindenyl) hafnium dimethyl; [(perfluorooctyl) (perfluoroisopropyl)ammonium]⁺--perfluorobiphenyl--[(perfluorofluorenyl (pentafluorofluorenyl) (trifluoroindenyl)borate]⁻/dimethylsilyl bis(naphthylmethylindenyl) hafnium dimethyl; [(perfluoropropyl) (butyl)ammonium]⁺--perfluorophenyl-[(2,3,5-trifluorophenyl(perfluorobiphenyl) (perfluoroindenyl)borate]⁻/dimethylsilyl bis (naphthylmethylindenyl) hafnium dimethyl; [((methyl (triethylsilyl))) (perfluorooctyl)ammonium]⁺--perfluorobiphenyl--[(perfluoronapthyl(2,5-difluorophenyl) (perfluorobiphenyl)gallinate]⁻/dimethylsilyl bis (naphthylmethylindenyl) hafnium dimethyl; [(ethyl (trimethylsilyl)) (2,3,5-trifuorophenyl)ammonium]⁺--perfluoroindenyl--[(perfluorofluorenyl(tetrafluoroindenyl) (pentafluoronaphthyl)aluminate]⁻/dimethylsilyl bis (phenylmethylindenyl) hafnium dimethyl; [(methyl (trimethylsilyl)) (1,2-difluorohexyl)arsonium]⁺--perfluorofluorenyl--[(perfluorophenyl(perfluoronapthyl) (pentafluorofluorenyl)aluminate]⁻/dimethylsilyl bis (phenylmethylindenyl) hafnium dimethyl; [(phenyl) (perfluoromethyl)ammonium]⁺--perfluoronapthyl--[(perfluorofluorenyl(pentafluoronaphthyl) (perfluoroindenyl)aluminate]⁻/dimethylsilyl bis (phenylmethylindenyl) hafnium dimethyl; [(ethyl) (phenyl) ammonium]⁺--perfluoroindenyl--[(perfluorofluorenyl(3,4-difluorophenyl) (2,5-difluorophenyl)borate]⁻/dimethylsilyl bis(phenylmethylindenyl) hafnium dimethyl; [(ethyl (triethylsilyl)) (perfluoroisopropyl)ammonium]⁺--perfluorophenyl-[(2,3,4-trifluorophenyl(perfluorophenyl) (pentafluorofluorenyl)borate]⁻/dimethylsilyl bis (phenylmethylindenyl) hafnium dimethyl; [(ethyl (triethylsilyl)) (isohexyl)arsonium]⁺--perfluoroindenyl--[(perfluoroindenyl(perfluorofluorenyl) (2,4-difluorophenyl) borate]⁻/dimethylsilyl bis(phenylmethylindenyl) hafnium dimethyl; (bis(ethyl(triethylsilyl))ammonium]⁺--pentafluorofluorenyl-[(perfluorophenyl(perfluoroindenyl) (tetrafluoroindenyl)borate]⁻/dimethylsilyl bis (phenylmethylindenyl) hafnium dimethyl; [(heptyl) (perfluoroethyl) phosphonium]⁺--2,3,5-trifluorophenyl--[(trifluoroindenyl(perfluorophenyl) (2,3-difluorophenyl) borate]⁻/dimethylsilyl bis(phenylmethylindenyl) hafnium dimethyl; [(isohexyl) (ethyl(triethylsilyl))ammonium]⁺--perfluorofluorenyl-[(perfluoronapthyl(perfluoroindenyl) (pentafluorofluorenyl)borate]⁻/dimethylsilyl bis (phenylmethylindenyl) hafnium dimethyl; [(isohexyl) (isopropyl)arsonium]⁺--perfluorobiphenyl--[(perfluorophenyl(2,3,5-trifluorophenyl) (2,4-difluorophenyl)borate]⁻/dimethylsilyl bis (phenylmethylindenyl) hafnium dimethyl; [(isopropyl) (isopentyl)ammonium]⁺--perfluorofluorenyl--[(perfluorophenyl(2,3-difluorophenyl) (perfluorofluorenyl) borate]⁻/dimethylsilyl bis(phenylmethylindenyl) hafnium dimethyl; [(pentyl) (2,3,5-trifluorophenyl) phosphonium]⁺--perfluoronapthyl--[bis(pentafluoronaphthyl) (perfluorobiphenyl)borate]⁻/dimethylsilyl bis (phenylmethylindenyl) hafnium dimethyl; [(perfluorohexyl) (methyl)ammonium]⁺--perfluoroindenyl--[(pentafluorofluorenyl(perfluorophenyl) (perfluorobiphenyl) borate]⁻/dimethylsilyl bis(phenylmethylindenyl) hafnium dimethyl; [(perfluoro-t-butyl) (butyl) phosphonium]⁺--2,3,5-trifluorophenyl--[(perfluorobiphenyl(tetrafluoroindenyl) (trifluoroindenyl)borate]⁻/dimethylsilyl bis (phenylmethylindenyl) hafnium dimethyl; [(propyl) (methyl) phosphonium]⁺⁻²,⁴-difluorophenyl--[(tetrafluoroindenyl(perfluoronapthyl) (tetrafluoronaphthyl) borate]⁻/dimethylsilyl bis(phenylmethylindenyl) hafnium dimethyl; [(propyl) (perfluoroisopentyl) phosphonium]⁺--perfluoropyrenyl--[(perfluorofluorenyl (pentafluorofluorenyl) (perfluoropyrenyl)borate]⁻/dimethylsilyl bis(phenylmethylindenyl) hafnium dimethyl; [(ethyl(triethylsilyl)) (2,3,6,7-tetrafluorooctyl) ammonium]⁺--perfluoroindenyl--[(2,3-difluorophenyl (perfluoronapthyl) (perfluorofluorenyl)gallinate]⁻/dimethylsilyl bis(phenylmethylindenyl) hafnium dimethyl; [(ethyl(trimethylsilyl)) (2,3,6,7-tetrafluorooctyl) ammonium]⁺--perfluoroindenyl--[(perfluorophenyl (perfluoropyrenyl) (tetrafluoroindenyl)gallinate]⁻/dimethylsilyl bis(phenylmethylindenyl) hafnium dimethyl; [(ethyl) (3-methylpentyl)ammonium]⁺--perfluorophenyl--[bis(trifluoroindenyl) (pentafluorofluorenyl)aluminate]⁻/dimethylsilyl bisindenyl hafnium dimethyl; [(isohexyl) (ethyl(trimethylsilyl)) phosphonium]⁺--perfluoroindenyl--[bis(perfluorofluorenyl) (perfluoroindenyl)aluminate]⁻/dimethylsilyl bisindenyl hafnium dimethyl; [(perfluoroheptyl) (perfluorohexyl)arsonium]⁺--perfluoronapthyl--[bis(perfluorophenyl) (2,3,4-trifluorophenyl)aluminate]⁻/dimethylsilyl bisindenyl hafnium dimethyl; [(1,2-difluorohexyl) (ethyl (trimethylsilyl))ammonium]⁺--tetrafluoroindenyl--[(2,3-difluorophenyl(perfluorobiphenyl) (pentafluoronaphthyl) borate]⁻/dimethylsilyl bisindenyl hafnium dimethyl; [(2,3,4,5-tetrafluorophenyl) (ethyl(trimethylsilyl))ammonium]⁺--trifluoroindenyl--[(perfluorofluorenyl(perfluorobiphenyl) (2,4-difluorophenyl)borate]⁻/dimethylsilyl bisindenyl hafnium dimethyl; [(3-methylpentyl) (perfluorooctyl) ammonium]⁺--perfluorobiphenyl--[(perfluoroindenyl (perfluoropyrenyl) (perfluoronapthyl)borate]⁻/dimethylsilyl bisindenyl hafnium dimethyl; [(isopentyl) (1,6-difluorohexyl)ammonium]⁺--perfluorophenyl--[bis(2,4-difluorophenyl) (2,5-difluorophenyl)borate]⁻/dimethylsilyl bisindenyl hafnium dimethyl; [(isopentyl) (butyl) phosphonium]⁺--perfluorobiphenyl--[(perfluoropyrenyl (tetrafluoroindenyl) (perfluoroindenyl)borate]⁻/dimethylsilyl bisindenyl hafnium dimethyl; [(methyl) (pentyl)ammonium]⁺--perfluoronapthyl--[(perfluoronapthyl (perfluorofluorenyl) (perfluorobiphenyl)borate]⁻/dimethylsilyl bisindenyl hafnium dimethyl; [(perfluorobutyl) (isohexyl) phosphonium]⁺--perfluoroindenyl--[(2,4-difluorophenyl(trifluoroindenyl) (perfluoroindenyl)borate]⁻/dimethylsilyl bisindenyl hafnium dimethyl; [(2,3,4,5-tetrafluorophenyl) (heptyl) arsonium]⁺--perfluoroindenyl--[(perfluoronapthyl (pentafluorofluorenyl) (perfluorophenyl)aluminate]⁻/dimethylsilyl(tetramethylcyclopentadienyl) (dodecylamido) hafnium dihydride; [(heptyl) (perfluoroisopropyl) ammonium]⁺--perfluorofluorenyl--[(perfluorobiphenyl (perfluorofluorenyl) (perfluoropyrenyl)aluminate]⁻/dimethylsilyl(tetramethylcyclopentadienyl) (dodecylamido) hafnium dihydride; [(isohexyl) (perfluoroheptyl) phosphonium]⁺--perfluorobiphenyl--[(perfluoronapthyl (perfluorophenyl) (2,3,4-trifluorophenyl)aluminate]⁻/ dimethylsilyl(tetramethylcyclopentadienyl) (dodecylamido) hafnium dihydride; [(isohexyl) (methyl)ammonium]⁺--perfluoronapthyl--[bis(pentafluorofluorenyl) (perfluoropyrenyl)aluminate]⁻/dimethylsilyl (tetramethylcyclopentadienyl) (dodecylamido) hafnium dihydride; [(perfluoroethyl) (perfluoropropyl) phosphonium]⁺--perfluorophenyl--bis(perfluorofluorenyl) (2,3-difluorophenyl)aluminate]⁻/dimethylsilyl (tetramethylcyclopentadienyl) (dodecylamido) hafnium dihydride; [(1,2-difluorohexyl) (butyl)ammonium]⁺--2,5-difluorophenyl--[bis(perfluoronapthyl) (perfluorophenyl) borate]⁻/dimethylsilyl(tetramethylcyclopentadienyl) (dodecylamido) hafnium dihydride; [(ethyl(triethylsilyl)) (isopentyl)ammonium]⁺--perfluorobiphenyl--[(2,3-difluorophenyl(perfluorofluorenyl) (trifluoroindenyl) borate]⁻/dimethylsilyl(tetramethylcyclopentadienyl) (dodecylamido) hafnium dihydride; [(ethyl(triethylsilyl)) (2,3,6,7-tetrafluorooctyl)ammonium]⁺--perfluorofluorenyl-[bis(pentafluoronaphthyl) (3,4-difluorophenyl)borate]⁻/ dimethylsilyl(tetramethylcyclopentadienyl) (dodecylamido) hafnium dihydride; [(ethyl(trimethylsilyl)) (pentyl) phosphonium]⁺--pentafluorofluorenyl--[(perfluoroindenyl) (perfluoronapthyl) (pentafluoronaphthyl)borate]⁻/ dimethylsilyl(tetramethylcyclopentadienyl) (dodecylamido) hafnium dihydride; [(heptyl) (ethyl(triethylsilyl)) ammonium]⁺--perfluorophenyl--[(3,4-difluorophenyl (perfluorofluorenyl) (perfluoronapthyl)borate]⁻/ dimethylsilyl(tetramethylcyclopentadienyl) (dodecylamido) hafnium dihydride; [(hexyl) (1,2-difluorohexyl) ammonium]⁺--perfluorophenyl--[(3,4-difluorophenyl(2,4-difluorophenyl) (perfluoronapthyl)borate]⁻/dimethylsilyl (tetramethylcyclopentadienyl) (dodecylamido) hafnium dihydride; [(perfluoromethyl) (1,6-difluorohexyl) ammonium]⁺--2,5-difluorophenyl--[(2,3,4-trifluorophenyl (perfluorobiphenyl) (perfluoroindenyl)borate]⁻/ dimethylsilyl(tetramethylcyclopentadienyl) (dodecylamido) hafnium dihydride; [(perfluorooctyl) (hexyl)ammonium]⁺--tetrafluoronaphthyl--[bis(2,4-difluorophenyl) (perfluorophenyl)borate]⁻/dimethylsilyl (tetramethylcyclopentadienyl) (dodecylamido) hafnium dihydride; [((methyl(triethylsilyl))) (heptyl)ammonium]⁺--3,4-difluorophenyl--[(perfluorobiphenyl (pentafluoronaphthyl) (perfluorofluorenyl)aluminate]⁻/ dimethylsilyl(tetramethylcyclopentadienyl) (dodecylamido) hafnium dimethyl; [(butyl) (perfluoromethyl)ammonium]⁺--perfluoronapthyl--bis(perfluorophenyl) (perfluoronapthyl) aluminate]⁻/dimethylsilyl(tetramethylcyclopentadienyl) (dodecylamido) hafnium dimethyl; [(perfluorophenyl) (perfluorobutyl) phosphonium]⁺--2,4-difluorophenyl--[(3,4-difluorophenyl(perfluorobiphenyl) (perfluorophenyl) aluminate]⁻/dimethylsilyl(tetramethylcyclopentadienyl) (dodecylamido) hafnium dimethyl; [(propyl) (isopentyl) phosphonium]⁺--perfluorofluorenyl--[(perfluoroindenyl) (perfluorobiphenyl) (perfluoropyrenyl)aluminate]⁻/ dimethylsilyl(tetramethylcyclopentadienyl) (dodecylamido) hafnium dimethyl; [((methyl(triethylsilyl))) (perfluoroisopentyl) phosphonium]⁺--perfluorobiphenyl-- [(perfluorofluorenyl(tetrafluoronaphthyl) (perfluorophenyl) borate]⁻/dimethylsilyl(tetramethylcyclopentadienyl) (dodecylamido) hafnium dimethyl; 1(2,3,4,5-tetrafluorophenyl) (perfluoroethyl) phosphonium]⁺--2,3-difluorophenyl--[(perfluorobiphenyl(perfluorofluorenyl) (2,4-difluorophenyl)borate]⁻/dimethylsilyl (tetramethylcyclopentadienyl) (dodecylamido) hafnium dimethyl; [(ethyl(triethylsilyl)) (propyl)ammonium]⁺--perfluoronapthyl--[bis(perfluoroindenyl) (tetrafluoronaphthyl)borate]⁻/dimethylsilyl (tetramethylcyclopentadienyl) (dodecylamido) hafnium dimethyl; [(ethyl(triethylsilyl)) (isopentyl)ammonium]⁺--2, 4-difluorophenyl--bis(perfluoroindenyl) (perfluorophenyl) borate]⁻/dimethylsilyl(tetramethylcyclopentadienyl) (dodecylamido) hafnium dimethyl; [(ethyl(trimethylsilyl)) (perfluoroethyl)ammonium]⁺--tetrafluoroindenyl-- [(perfluorobiphenyl(perfluoronapthyl) (2,5-difluorophenyl) borate]⁻/dimethylsilyl(tetramethylcyclopentadienyl) (dodecylamido) hafnium dimethyl; [(isohexyl) (hexyl) phosphonium]⁺--2,5-difluorophenyl--[bis(perfluoronapthyl) (perfluorophenyl)borate]⁻/dimethylsilyl (tetramethylcyclopentadienyl) (dodecylamido) hafnium dimethyl; [(methyl(triethylsilyl)) (isohexyl)ammonium]⁺--pentafluorofluorenyl--[bis(perfluoronapthyl) (perfluorobiphenyl)borate]⁻/dimethylsilyl (tetramethylcyclopentadienyl) (dodecylamido) hafnium dimethyl; [(perfluoroisopentyl) (ethyl(trimethylsilyl)) phosphonium]⁺--2,3-difluorophenyl--[(2,5-difluorophenyl (tetrafluoroindenyl) (perfluoroindenyl)borate]⁻/ dimethylsilyl(tetramethylcyclopentadienyl) (dodecylamido) hafnium dimethyl; [(perfluorophenyl) (1,2-difluorohexyl) ammonium]⁺--perfluoronapthyl--[bis(perfluorofluorenyl) (perfluoroindenyl)borate]⁻/dimethylsilyl (tetramethylcyclopentadienyl) (dodecylamido) hafnium dimethyl; [(propyl) (3-methylpentyl)ammonium]⁺--perfluoroindenyl--[(perfluorobiphenyl(3,4-difluorophenyl) (perfluorofluorenyl)borate]⁻/dimethylsilyl (tetramethylcyclopentadienyl) (dodecylamido) hafnium dimethyl; [(methyl(trimethylsilyl)) (ethyl)ammonium]⁺--2, 3-difluorophenyl--[(perfluoronapthyl(2,5-difluorophenyl) (pentafluoronaphthyl)gallinate]⁻/dimethylsily (tetramethylcyclopentadienyl) (dodecylamido) hafnium dimethyl; [(perfluoromethyl) (phenyl)ammonium]⁺--tetrafluoroindenyl--[(perfluoronapthyl(perfluorofluorenyl) (perfluorobiphenyl)aluminate]⁻/dimethylsilyl (tetramethylcyclopentadienyl) (t-butylamido) zirconium dimethyl; [(2,3,5-trifluorophenyl) (methyl(trimethylsilyl)) ammonium]⁺--perfluorophenyl--[(perfluorophenyl (perfluoronapthyl) (perfluoropyrenyl)borate]⁻/dimethylsilyl (tetramethylcyclopentadienyl) (t-butylamido) zirconium dimethyl; [(3-methylpentyl) (isohexyl) phosphonium]⁺--tetrafluoronaphthyl--[(2,3-difluorophenyl(perfluorophenyl) (perfluoropyrenyl)borate]⁻/dimethylsilyl (tetramethylcyclopentadienyl) (t-butylamido) zirconium dimethyl; [(heptyl) (2,3,6,7-tetrafluorooctyl)ammonium]⁺--2,3,5-trifluorophenyl--[(perluorophenyl(tetrafluoroindenyl) (perfluorobiphenyl)borate]⁻/dimethylsilyl (tetramethylcyclopentadienyl) (t-butylamido) zirconium dimethyl; [(hexyl) (perfluoroheptyl) phosphonium]⁺--perfluoropyrenyl--[(2,4-difluorophenyl(perfluoropyrenyl) (perfluorophenyl)borate]⁻/dimethylsilyl (tetramethylcyclopentadienyl) (t-butylamido) zirconium dimethyl; [(hexyl) (butyl)ammonium]⁺--tetrafluoroindenyl--[(2,3,4-trifluorophenyl (tetrafluoroindenyl) (perfluorophenyl)borate]⁻/dimethylsilyl (tetramethylcyclopentadienyl) (t-butylamido) zirconium dimethyl; [(isohexyl) (perfluorobutyl)arsonium]⁺--2,5-difluorophenyl--[bis(perfluorophenyl) (perfluorofluorenyl) borate]⁻/dimethylsilyl(tetramethylcyclopentadienyl) (t-butylamido) zirconium dimethyl; [(isopropyl) (phenyl) ammonium]⁺--perfluorophenyl--[(perfluoroindenyl (tetrafluoroindenyl) (perfluoronapthyl)borate]⁻/ dimethylsilyl(tetramethylcyclopentadienyl) (t-butylamido) zirconium dimethyl; [(pentyl) (2,3,4,5-tetrafluorophenyl) phosphonium]⁺--pentafluorofluorenyl--[(2,3,5-trifluorophenyl(tetrafluoroindenyl) (perfluoronapthyl)

borate]⁻/dimethylsilyl(tetramethylcyclopentadienyl) (t-butylamido) zirconium dimethyl; [(perfluoroheptyl) (perfluorophenyl)arsonium]⁺--pentafluoronaphthyl-- [(perfluoropyrenyl(perfluorophenyl) (2,3,4-trifluorophenyl) borate]⁻/dimethylsilyl(tetramethylcyclopentadienyl) (t-butylamido) zirconium dimethyl; [(perfluorohexyl) (1,6-difluorohexyl)ammonium]⁺--3,4-difluorophenyl-- [(perfluorophenyl(3,4-difluorophenyl) (tetrafluoronaphthyl) borate]⁻/dimethylsilyl(tetramethylcyclopentadienyl) (t-butylamido) zirconium dimethyl; [(perfluorohexyl) (methyl(trimethylsilyl))ammonium]⁺--perfluorophenyl-- [(pentafluoronaphthyl(perfluoroindenyl) (trifluoroindenyl) borate]⁻/dimethylsilyl(tetramethylcyclopentadienyl) (t-butylamido) zirconium dimethyl; [(perfluoropentyl) (2,3, 5-trifluorophenyl)ammonium]⁺--perfluoroindenyl-- [(perfluorobiphenyl(perfluorofluorenyl) (tetrafluoronaphthyl)borate]⁻/dimethylsilyl (tetramethylcyclopentadienyl) (t-butylamido) zirconium dimethyl; [(perfluoro-t-butyl) (methyl(trimethylsilyl)) ammonium]⁺--3,4-difluorophenyl--[(perfluoroindenyl (perfluorophenyl) (perfluorobiphenyl)borate]⁻/dimethylsilyl (tetramethylcyclopentadienyl) (t-butylamido) zirconium dimethyl; [(phenyl) (ethyl(triethylsilyl))ammonium]⁺-- perfluoronapthyl--[(perfluoropyrenyl(trifluoroindenyl) (perfluoronapthyl)borate]⁻/dimethylsilyl (tetramethylcyclopentadienyl) (t-butylamido) zirconium dimethyl; [(phenyl) (perfluoro-t-butyl)ammonium]⁺-- perfluoroindenyl--[(perfluoropyrenyl(2,3,4-trifluorophenyl) (perfluoroindenyl)borate]⁻/dimethylsilyl (tetramethylcyclopentadienyl) (t-butylamido) zirconium dimethyl; [(phenyl) (ethyl(trimethylsilyl)) phosphonium]⁺-- perluorophenyl--[(tetrafluoroindenyl(perfluorofluorenyl) (pentafluoronaphthyl)borate]⁻/dimethylsilyl (tetramethylcyclopentadienyl) (t-butylamido) zirconium dimethyl; [(2,3,6,7-tetrafluorooctyl) (ethyl(triethylsilyl)) ammonium]⁺--perfluoronapthyl--[bis(perfluorobiphenyl) (2,5-difluorophenyl)gallinate]⁻/dimethylsilyl (tetramethylcyclopentadienyl) (t-butylamido) zirconium dimethyl; [(pentyl) (propyl)ammonium]⁺-- tetrafluoronaphthyl--[(2,3,5-trifluorophenyl (perfluoroindenyl) (2,3,4-trifluorophenyl)gallinate]⁻/ dimethylsilyl(tetramethylcyclopentadienyl) (t-butylamido) zirconium dimethyl; [(ethyl(triethylsilyl)) (isohexyl) phosphonium]⁺--perfluorophenyl--[(3,4-difluorophenyl (perfluoroindenyl) (2,5-difluorophenyl)aluminate]⁻/ dimethylsilyl(tetramethylcyclopentadienyl) (tert-butylamido) titanium dichloride; [((methyl(triethylsilyl))) (methyl)ammonium]⁺--2,4-difluorophenyl-- [(trifluoroindenyl(perfluoronapthyl) (2,4-difluorophenyl) borate]⁻/dimethylsilyl(tetramethylcyclopentadienyl) (tert-butylamido) titanium dichloride; [(2,3,6,7-tetrafluorooctyl) (perfluoroisopropyl)ammonium]⁺--perfluoroindenyl--[bis (perfluorofluorenyl) (tetrafluoroindenyl)borate]⁻/ dimethylsilyl(tetramethylcyclopentadienyl) (tertbutylamido) titanium dichloride; [(ethyl) (hexyl) ammonium]⁺--2,3,5-trifluorophenyl--[(perfluoroindenyl(2, 4-difluorophenyl) (2,3,5-trifluorophenyl)borate]⁻/ dimethylsilyl(tetramethylcyclopentadienyl) (tert-butylamido) titanium dichloride; [(methyl(trimethylsilyl)) (perfluoroisopentyl) phosphonium]⁺--perfluoronapthyl--[(2, 3,5-trifluorophenyl(perfluoroindenyl) (2,4-difluorophenyl) borate]⁻/dimethylsilyl(tetramethylcyclopentadienyl) (tert-butylamido) titanium dichloride; [(methyl(trimethylsilyl)) (methyl)ammonium]⁺--pentafluorofluorenyl-- [(perfluoroindenyl(perfluorofluorenyl) (2,5-difluorophenyl) borate]⁻/dimethylsilyl(tetramethylcyclopentadienyl) (tert-butylamido) titanium dichloride; [(methyl(trimethylsilyl)) (octyl)ammonium]⁺--2,3,5-trifluorophenyl-- [(perfluoroindenyl(2,3,4-trifluorophenyl) (2,3,5-trifluorophenyl)borate]⁻/dimethylsilyl (tetramethylcyclopentadienyl) (tertbutylamido) titanium dichloride; [(perfluorobutyl) (perfluoroethyl) phosphonium]⁺--perfluorobiphenyl--[(perfluoroindenyl(2,3, 5-trifluorophenyl) (pentafluoronaphthyl)borate]⁻/ dimethylsilyl(tetramethylcyclopentadienyl) (tert-butylamido) titanium dichloride; [(perfluorobutyl) (1,2-difluorohexyl) phosphonium]⁺--perfluoronapthyl-- [(pentafluorofluorenyl(perfluorophenyl) (perfluoronapthyl) borate]⁻/dimethylsilyl(tetramethylcyclopentadienyl) (tert-butylamido) titanium dichloride; [(perfluorobutyl) (ethyl) ammonium]⁺--perfluorophenyl--[(perfluorophenyl(2,5-difluorophenyl) (trifluoroindenyl)borate]⁻/dimethylsilyl (tetramethylcyclopentadienyl) (tert-butylamido) titanium dichloride; [(perfluoropropyl) (1,6-difluorohexyl) phosphonium]⁺--2,5-difluorophenyl--[(perfluorophenyl (tetrafluoronaphthyl) (perfluorobiphenyl)borate]⁻/ dimethylsilyl(tetramethylcyclopentadienyl) (tert-butylamido) titanium dichloride; [(ethyl(triethylsilyl)) (ethyl)ammonium]⁺--perfluorophenyl--[(trifluoroindenyl (perfluorobiphenyl) (pentafluoronaphthyl)gallinate]⁻/ dimethylsilyl(tetramethylcyclopentadienyl) (tert-butylamido) titanium dichloride; [(ethyl(triethylsilyl)) (heptyl)arsonium]⁺--perfluoroindenyl--[(2,3,4-trifluorophenyl(tetrafluoroindenyl) (perfluoroindenyl) aluminate]⁻/dimethylsilylbis(2-methylbenzindenyl) zirconium dimethyl; [(ethyl(triethylsilyl)) (isopentyl) ammonium]⁺--2,5-difluorophenyl--[(tetrafluoroindenyl (perfluoroindenyl) (pentafluorofluorenyl)borate]⁻/ dimethylsilylbis(2-methylbenzindenyl) zirconium dimethyl; [(methyl(trimethylsilyl)) (hexyl)ammonium]⁺-- perfluorophenyl--[(perfluorophenyl(2,3,5-trifluorophenyl) (2,3-difluorophenyl)borate]⁻/dimethylsilylbis(2-methylbenzindenyl) zirconium dimethyl; [(perfluorohexyl) (1,6-difluorohexyl) phosphonium]⁺--perfluorophenyl-- [(perfluoronapthyl(2,3,5-trifluorophenyl) (tetrafluoroindenyl)borate]⁻/dimethylsilylbis(2-methylbenzindenyl) zirconium dimethyl; [(perfluoropentyl) (phenyl)arsonium]⁺--perfluoronapthyl--[(perfluorofluorenyl (perfluorobiphenyl) (pentafluoronaphthyl)borate]⁻/ dimethylsilylbis(2-methylbenzindenyl) zirconium dimethyl; [(perfluoropropyl) (phenyl)ammonium]⁺-- perfluoroindenyl--[(2,3,4-trifluorophenyl(perfluoroindenyl) (pentafluorofluorenyl)borate]⁻/dimethylsilylbis(2-methylbenzindenyl) zirconium dimethyl; [(perfluoro-t-butyl) (perfluoropropyl)ammonium]⁺--perfluorophenyl-- [bis(perfluorobiphenyl) (perfluorofluorenyl)borate]⁻/ dimethylsilylbis(2-methylbenzindenyl) zirconium dimethyl; [(phenyl) (ethyl(trimethylsilyl)) phosphonium]⁺-- pentafluorofluorenyl--[bis(perfluorobiphenyl) (trifluoroindenyl)borate]⁻/dimethylsilylbis(2-methylbenzindenyl) zirconium dimethyl; [(propyl) (methyl (triethylsilyl)) phosphonium]⁺--perluoronapthyl-- [(perfluorobiphenyl(perfluorofluorenyl) (pentafluorofluorenyl)borate]⁻/dimethylsilylbis(2-methylbenzindenyl) zirconium dimethyl; [(perfluorohexyl) ((methyl(triethylsilyl( ))ammonium]⁺--perfluoroindenyl-- [(perfluorofluorenyl(perfluoronapthyl) (2,3-difluorophenyl) gallinate]⁻/dimethylsilylbis(2-methylbenzindenyl) zirconium dimethyl; [(2,3,5-trifluorophenyl) (isohexyl) phosphonium]⁺--perfluoropyrenyl--[(perfluorophenyl (perfluoronapthyl) (trifluoroindenyl)aluminate]⁻/ dimethylsilylbis(tetrahydroindenyl) zirconium dichloride; [(ethyl(triethylsilyl)) (3-methylpentyl)ammonium]⁺-- perfluorofluorenyl--[bis(perfluoronapthyl)

(perfluorophenyl)aluminate]⁻/dimethylsilylbis (tetrahydroindenyl) zirconium dichloride; [(hexyl) (perfluoroisopropyl) phosphonium]⁺--perfluorofluorenyl--[(tetrafluoronaphthyl(perfluorofluorenyl) (perfluorobiphenyl)aluminate]⁻/dimethylsilylbis (tetrahydroindenyl) zirconium dichloride; [(perfluoroisopentyl) (perfluoropentyl) phosphonium]⁺--pentafluoronaphthyl--[(perfluorophenyl(tetrafluoroindenyl) (perfluoropyrenyl)aluminate]⁻/dimethylsilylbis (tetrahydroindenyl) zirconium dichloride; [(perfluorooctyl) ((methyl(triethylsilyl()))arsonium]⁺--perfluoronapthyl--[(3,4-difluorophenyl(perfluorobiphenyl) (2,3-difluorophenyl) aluminate]⁻/dimethylsilylbis(tetrahydroindenyl) zirconium dichloride; (bis(ethyl(triethylsilyl))ammonium]⁺--trifluoroindenyl--[bis(perfluorofluorenyl) (perfluorobiphenyl)borate]⁻/dimethylsilylbis (tetrahydroindenyl) zirconium dichloride; [(ethyl (triethylsilyl)) (isohexyl)ammonium]⁺--perfluoronapthyl--[(pentafluoronaphthyl(tetrafluoronaphthyl) (2,3,4-trifluorophenyl)borate]⁻/dimethylsilylbis (tetrahydroindenyl) zirconium dichloride; [(isohexyl) (methyl(trimethylsilyl))ammonium]⁺--perfluorophenyl--[bis(perfluoroindenyl) (perfluorofluorenyl)borate]⁻/ dimethylsilylbis(tetrahydroindenyl) zirconium dichloride; [(isohexyl) ((methyl(triethylsilyl))) phosphonium]⁺--perfluoroindenyl--[(2,3,5-trifluorophenyl (perfluorofluorenyl) (perfluorobiphenyl)borate]⁻/ dimethylsilylbis(tetrahydroindenyl) zirconium dichloride; [(methyl(triethylsilyl) (perfluoro-t-butyl)ammonium]⁺--perfluorobiphenyl--[(3,4-difluorophenyl(tetrafluoroindenyl) (perfluorofluorenyl)borate]⁻/dimethylsilylbis (tetrahydroindenyl) zirconium dichloride; [(ethyl (trimethylsilyl)) (1,2-difluorohexyl)ammonium]⁺--perfluoronapthyl--[(perfluorophenyl(perfluoroindenyl) (perfluorobiphenyl)aluminate]⁻/diphenylmethyl (cylcopentadienyl) (2,7-dimethylfluorenyl) hafnium dimethyl; [(isopropyl) (perfluorophenyl)ammonium]⁺--pentafluorofluorenyl--[bis(perfluorophenyl) (2,3,4-trifluorophenyl)aluminate]⁻/diphenylmethyl (cylcopentadienyl) (2,7-dimethylfluorenyl) hafnium dimethyl; [(methyl(trimethylsilyl)) (isopentyl)ammonium]⁺--perfluoroindenyl--[(2,4-difluorophenyl(2,3,4-trifluorophenyl) (2,3-difluorophenyl)aluminate]⁻/ diphenylmethyl (cylcopentadienyl) (2,7-dimethylfluorenyl) hafnium dimethyl; [(perfluoroisopentyl) (methyl (trimethylsilyl))ammonium]⁺--perfluorofluorenyl--[(2,4-difluorophenyl(pentafluoronaphthyl) (trifluoroindenyl) aluminate]⁻/diphenylmethyl (cylcopentadienyl) (2,7-dimethylfluorenyl) hafnium dimethyl; [(2,3,5-trifluorophenyl) (methyl(trimethylsilyl)) phosphonium]⁺--perfluorophenyl--[(perfluoroindenyl(perfluorobiphenyl) (2,4-difluorophenyl)borate]⁻/diphenylmethyl (cylcopentadienyl) (2,7-dimethylfluorenyl) hafnium dimethyl; [(2,3,6,7-tetrafluorooctyl) (isohexyl)ammonium]⁺--perfluoronapthyl--[(trifluoroindenyl(tetrafluoronaphthyl) (perfluoronapthyl)borate]⁻/diphenylmethyl (cylcopentadienyl) (2,7-dimethylfluorenyl) hafnium dimethyl; [(3-methylpentyl) (perfluorophenyl) phosphonium]⁺--perfluoronapthyl--[(perfluorobiphenyl(perfluoroindenyl) (pentafluoronaphthyl)borate]⁻/diphenylmethyl (cylcopentadienyl) (2,7-dimethylfluorenyl) hafnium dimethyl; [(isopentyl) (methyl(trimethylsilyl))ammonium]⁺--perfluoropyrenyl--[bis(perfluorofluorenyl) (perfluorobiphenyl)borate]⁻/diphenylmethyl (cylcopentadienyl) (2,7-dimethylfluorenyl) hafnium dimethyl; [(methyl(trimethylsilyl)) (ethyl(triethylsilyl)) ammonium]⁺--2,4-difluorophenyl--[bis(2,3-di fluorophenyl) (tetrafluoroindenyl)borate]⁻/diphenylmethyl (cylcopentadienyl) (2,7-dimethylfluorenyl) hafnium dimethyl; [(octyl) (perfluoroethyl)ammonium]⁺--trifluoroindenyl--[bis(3,4-difluorophenyl) (perfluoronapthyl)borate]⁻/diphenylmethyl (cylcopentadienyl) (2,7-dimethylfluorenyl) hafnium dimethyl; [(octyl) (butyl) phosphonium]⁺--trifluoroindenyl--[(tetrafluoroindenyl(perfluorophenyl) (3,4-difluorophenyl) borate]⁻/diphenylmethyl (cylcopentadienyl) (2,7-dimethylfluorenyl) hafnium dimethyl; [(perfluoromethyl) (octyl) phosphonium]⁺--perfluoronapthyl--[(tetrafluoroindenyl(perfluorophenyl) (2,3,5-trifluorophenyl)borate]⁻/diphenylmethyl (cylcopentadienyl) (2,7-dimethylfluorenyl) hafnium dimethyl; [(perfluorophenyl) (hexyl)ammonium]⁺--pentafluorofluorenyl--[(perfluoroindenyl(2,3,5-trifluorophenyl) (tetrafluoroindenyl)borate]⁻/ diphenylmethyl (cylcopentadienyl) (2,7-dimethylfluorenyl) hafnium dimethyl; [(perfluorophenyl) (methyl (trimethylsilyl))ammonium]⁺--perfluoropyrenyl--[(pentafluorofluorenyl(tetrafluoronaphthyl) (perfluorobiphenyl)borate]⁻/diphenylmethyl (cylcopentadienyl) (2,7-dimethylfluorenyl) hafnium dimethyl; (bis(perfluoropropyl)ammonium]⁺--2,3-difluorophenyl--[bis(perfluorophenyl) (3,4-difluorophenyl) borate]⁻/diphenylmethyl (cylcopentadienyl) (2,7-dimethylfluorenyl) hafnium dimethyl; [(perfluoropropyl) (isohexyl)ammonium]⁺--3,4-difluorophenyl--[bis (perfluoronapthyl) (perfluorobiphenyl)borate]⁻/ diphenylmethyl (cylcopentadienyl) (2,7-dimethylfluorenyl) hafnium dimethyl; [(perfluoro-t-butyl) (phenyl)arsonium]⁺--perfluorobiphenyl--[(perfluorophenyl(pentafluoronaphthyl) (perfluorofluorenyl)borate]⁻/diphenylmethyl (cylcopentadienyl) (2,7-dimethylfluorenyl) hafnium dimethyl; [(propyl) (isohexyl)ammonium]⁺--perfluorobiphenyl--[bis(perfluorophenyl) (perfluorofluorenyl)borate]⁻/diphenylmethyl (cylcopentadienyl) (2,7-dimethylfluorenyl) hafnium dimethyl; [(t-butyl) (methyl(triethylsilyl)) phosphonium]⁺--tetrafluoroindenyl--[(perfluoroindenyl(perfluorofluorenyl) (perfluorophenyl)borate]⁻/diphenylmethyl (cylcopentadienyl) (2,7-dimethylfluorenyl) hafnium dimethyl; [(2,3,6,7-tetrafluorooctyl) (perfluoroheptyl) ammonium]⁺--perfluoronapthyl--[(trifluoroindenyl (perfluorophenyl) (perfluorofluorenyl)gallinate]⁻/ diphenylmethyl (cylcopentadienyl) (2,7-dimethylfluorenyl) hafnium dimethyl; [(perfluorophenyl) (perfluoroisopentyl) ammonium]⁺--2,3,4-trifluorophenyl--[(2,4-difluorophenyl (trifluoroindenyl) (perfluorophenyl)gallinate]⁻/ diphenylmethyl (cylcopentadienyl) (2,7-dimethylfluorenyl) hafnium dimethyl; [(2,3,4,5-tetrafluorophenyl) (3-methylpentyl)ammonium]⁺--2,4-difluorophenyl--[(pentafluorofluorenyl(perfluoronapthyl) (perfluorophenyl) aluminate]⁻/diphenylmethyl (cylcopentadienyl) (2,7-di-t-butyl-fluorenyl) hafnium dimethyl; [(isopentyl) (isohexyl) ammonium]⁺--2,5-difluorophenyl--[bis(perfluorobiphenyl) (perfluorofluorenyl)aluminate]⁻/diphenylmethyl (cylcopentadienyl) (2,7-di-t-butyl-fluorenyl) hafnium dimethyl; [(methyl(trimethylsilyl)) (2,3,4,5-tetrafluorophenyl) ammonium]⁺--perfluorophenyl--[(tetrafluoroindenyl (perfluoropyrenyl) (perfluorophenyl)aluminate]⁻/ diphenylmethyl (cylcopentadienyl) (2,7-di-t-butyl-fluorenyl) hafnium dimethyl; [(methyl(trimethylsilyl)) (perfluoroisopentyl)ammonium]⁺--2,4-difluorophenyl--[(perfluoronapthyl(perfluorobiphenyl) (2,4-difluorophenyl) aluminate]⁻/diphenylmethyl (cylcopentadienyl) (2,7-di-t-butyl-fluorenyl) hafnium dimethyl; [(perfluorohexyl)

(perfluoroisopentyl)ammonium]⁺--perfluorophenyl--[(perfluoropyrenyl(perfluorophenyl) (perfluoroindenyl) aluminate]⁻/diphenylmethyl (cylcopentadienyl) (2,7-di-t-butyl-fluorenyl) hafnium dimethyl; [(perfluoroisopentyl) (isohexyl)ammonium]⁺--pentafluoronaphthyl--[(perfluorophenyl(perfluoronapthyl) (perfluoroindenyl) aluminate]⁻/diphenylmethyl (cylcopentadienyl) (2,7-di-t-butyl-fluorenyl) hafnium dimethyl; [((methyl(triethylsilyl))) (hexyl)ammonium]⁺--pentafluorofluorenyl--[(2,3,5-trifluorophenyl(tetrafluoroindenyl) (trifluoroindenyl) borate]⁻/diphenylmethyl (cylcopentadienyl) (2,7-di-t-butyl-fluorenyl) hafnium dimethyl; (bis(1,2-difluorohexyl) phosphonium]⁺--2,3-difluorophenyl--[(2,3,4-trifluorophenyl(perfluorophenyl) (2,4-difluorophenyl) borate]⁻/diphenylmethyl (cylcopentadienyl) (2,7-di-t-butyl-fluorenyl) hafnium dimethyl; [(ethyl(trimethylsilyl)) (ethyl (triethylsilyl))ammonium]⁺--perfluorofluorenyl--[(2,3-difluorophenyl(2,4-difluorophenyl) (perfluorobiphenyl) borate]⁻/diphenylmethyl (cylcopentadienyl) (2,7-di-t-butyl-fluorenyl) hafnium dimethyl; (bis(heptyl) phosphonium]⁺--2,3,5-trifluorophenyl--[(perfluoroindenyl (tetrafluoroindenyl) (2,3,5-trifluorophenyl)borate]⁻/diphenylmethyl (cylcopentadienyl) (2,7-di-t-butyl-fluorenyl) hafnium dimethyl; [(methyl(triethylsilyl)) (perfluoroethyl)ammonium]⁺--perfluoroindenyl--[bis (perfluorobiphenyl) (pentafluoronaphthyl)borate]⁻/diphenylmethyl (cylcopentadienyl) (2,7-di-t-butyl-fluorenyl) hafnium dimethyl; [(perfluorohexyl) (perfluoroethyl) phosphonium]⁺--perfluorobiphenyl--[bis (perfluorophenyl) (perfluoroindenyl)borate]⁻/diphenylmethyl (cylcopentadienyl) (2,7-di-t-butyl-fluorenyl) hafnium dimethyl; [(perfluoro-t-butyl) (isopentyl) ammonium]⁺--perfluorobiphenyl--[(perfluorophenyl(2,5-difluorophenyl) (pentafluorofluorenyl)borate]⁻/diphenylmethyl (cylcopentadienyl) (2,7-di-t-butyl-fluorenyl) hafnium dimethyl; [(perfluoro-t-butyl) (heptyl) phosphonium]⁺--perfluorophenyl--[(perfluorobiphenyl (perfluorofluorenyl) (2,3-difluorophenyl)borate]⁻/diphenylmethyl (cylcopentadienyl) (2,7-di-t-butyl-fluorenyl) hafnium dimethyl; [(perfluoro-t-butyl) (ethyl (trimethylsilyl))arsonium]⁺--2,3-difluorophenyl--[(pentafluoronaphthyl(perfluoroindenyl) (perfluorobiphenyl)borate]⁻/diphenylmethyl (cylcopentadienyl) (2,7-di-t-butyl-fluorenyl) hafnium dimethyl; [(t-butyl) (3-methylpentyl)arsonium]⁺--2,3,5-trifluorophenyl--[(3,4-difluorophenyl(perfluoroindenyl) (perfluoroindenyl)borate]⁻/diphenylmethyl (cylcopentadienyl) (2,7-di-t-butyl-fluorenyl) hafnium dimethyl; [(perfluoropentyl) (perfluoromethyl) phosphonium]⁺--tetrafluoronaphthyl--[(perfluoronapthyl(2,3,5-trifluorophenyl) (2,3-difluorophenyl)gallinate]⁻/diphenylmethyl (cylcopentadienyl) (2,7-di-t-butyl-fluorenyl) hafnium dimethyl; [(ethyl(triethylsilyl)) (pentyl) ammonium]⁺--perfluoronapthyl--[(pentafluoronaphthyl (perfluoropyrenyl) (3,4-difluorophenyl)aluminate]⁻/diphenylmethyl (cylcopentadienyl) (fluorenyl) hafnium dimethyl; (bis(octyl)ammonium]⁺--2,3-difluorophenyl--[(2,4-difluorophenyl(perfluoropyrenyl) (perfluoroindenyl) aluminate]⁻/diphenylmethyl (cylcopentadienyl) (fluorenyl) hafnium dimethyl; [(phenyl) (methyl) phosphonium]⁺--perfluoropyrenyl--[(trifluoroindenyl(perfluorofluorenyl) (perfluorobiphenyl)aluminate]⁻/diphenylmethyl (cylcopentadienyl) (fluorenyl) hafnium dimethyl; [(1,6-difluorohexyl) (perfluoromethyl)ammonium]⁺--perfluoroindenyl--[(pentafluorofluorenyl(perfluorofluorenyl) (2,3,4-trifluorophenyl)borate]⁻/diphenylmethyl (cylcopentadienyl) (fluorenyl) hafnium dimethyl; [(2,3,5-trifluorophenyl) (methyl)ammonium]⁺--perfluoroindenyl--[(2,5-difluorophenyl(3,4-difluorophenyl) (perfluoroindenyl) borate]⁻/diphenylmethyl (cylcopentadienyl) (fluorenyl) hafnium dimethyl; [(ethyl) (3-methylpentyl)ammonium]⁺--perfluorofluorenyl--[(tetrafluoroindenyl(perfluorophenyl) (perfluoroindenyl)borate]⁻/diphenylmethyl (cylcopentadienyl) (fluorenyl) hafnium dimethyl; [(ethyl (triethylsilyl)) (2,3,4,5-tetrafluorophenyl) phosphonium]⁺--perfluoroindenyl--[bis(perfluoroindenyl) (2,3,5-trifluorophenyl)borate]⁻/diphenylmethyl (cylcopentadienyl) (fluorenyl) hafnium dimethyl; [(pentyl) (butyl) ammonium]⁺--perfluoronapthyl--[(perfluorophenyl(2,5-difluorophenyl) (2,3-difluorophenyl)borate]⁻/diphenylmethyl (cylcopentadienyl) (fluorenyl) hafnium dimethyl; [(perfluoropropyl) (perfluorooctyl)ammonium]⁺--perfluoronapthyl--[(perfluorofluorenyl(3,4-difluorophenyl) (perfluoronapthyl)borate]⁻/diphenylmethyl (cylcopentadienyl) (fluorenyl) hafnium dimethyl; [(2,3,4,5-tetrafluorophenyl) (perfluorohexyl) phosphonium]⁺--pentafluoronaphthyl--[(perfluoroindenyl(perfluoronapthyl) (2,3-difluorophenyl)aluminate]⁻/diphenylmethyl (fluorenyl) (cyclopentadienyl) hafnium dimethyl; [(2,3,6,7-tetrafluorooctyl) (heptyl)ammonium]⁺--perfluorofluorenyl--[(perfluorobiphenyl(perfluorophenyl) (2,4-difluorophenyl) aluminate]⁻/diphenylmethyl (fluorenyl) (cyclopentadienyl) hafnium dimethyl; [(heptyl) (hexyl)ammonium]⁺--tetrafluoronaphthyl--[tris(perfluoroindenyl)aluminate]⁻/diphenylmethyl (fluorenyl) (cyclopentadienyl) hafnium dimethyl; [(perfluoroethyl) (2,3,6,7-tetrafluorooctyl) ammonium]⁺--perfluoronapthyl--[(trifluoroindenyl (perfluoroindenyl) (perfluoropyrenyl)aluminate]⁻/diphenylmethyl (fluorenyl) (cyclopentadienyl) hafnium dimethyl; [(propyl) (perfluorophenyl)ammonium]⁺--perfluorofluorenyl--[(perfluoronapthyl(perfluorofluorenyl) (perfluoroindenyl)aluminate]⁻/diphenylmethyl (fluorenyl) (cyclopentadienyl) hafnium dimethyl; [(2,3,5-trifluorophenyl) (phenyl)ammonium]⁺--perfluorophenyl--[(trifluoroindenyl(perfluoronapthyl) (perfluorofluorenyl) borate]⁻/diphenylmethyl (fluorenyl) (cyclopentadienyl) hafnium dimethyl; [(butyl) (perfluoroisopentyl) phosphonium]⁺--perfluorobiphenyl--[(perfluoronapthyl(2,3-difluorophenyl) (perfluorobiphenyl)borate]⁻/diphenylmethyl (fluorenyl) (cyclopentadienyl) hafnium dimethyl; [(ethyl) (methyl) phosphonium]⁺--3,4-difluorophenyl--[bis(perfluoroindenyl) (2,5-difluorophenyl) borate]⁻/diphenylmethyl (fluorenyl) (cyclopentadienyl) hafnium dimethyl; [(ethyl(trimethylsilyl)) (2,3,6,7-tetrafluorooctyl)ammonium]⁺--perfluorophenyl--[(trifluoroindenyl(perfluorobiphenyl) (3,4-difluorophenyl) borate]⁻/diphenylmethyl (fluorenyl) (cyclopentadienyl) hafnium dimethyl; [(ethyl(trimethylsilyl)) (perfluoropropyl) phosphonium]⁺--perfluorophenyl--[(perfluoroindenyl (perfluorobiphenyl) (pentafluoronaphthyl)borate]⁻/diphenylmethyl (fluorenyl) (cyclopentadienyl) hafnium dimethyl; [(isopropyl) (hexyl)ammonium]⁺--2,5-difluorophenyl--[(perfluorophenyl(perfluoronapthyl) (perfluoroindenyl)borate]⁻/diphenylmethyl (fluorenyl) (cyclopentadienyl) hafnium dimethyl; [(perfluoromethyl) (isohexyl)ammonium]⁺--perfluoronapthyl--[(2,5-difluorophenyl(perfluorophenyl) (2,3,4-trifluorophenyl) borate]⁻/diphenylmethyl (fluorenyl) (cyclopentadienyl) hafnium dimethyl; [(perfluoropentyl) (perfluoro-t-butyl) ammonium]⁺--perfluorobiphenyl--[(3,4-difluorophenyl (perfluoronapthyl) (perfluoroindenyl)borate]⁻/diphenylmethyl (fluorenyl) (cyclopentadienyl) hafnium dimethyl; [(perfluoropropyl) (3-methylpentyl)arsonium]⁺--perfluorobiphenyl--[(2,3,4-trifluorophenyl(2,4- difluorophenyl) (perfluorobiphenyl)borate]⁻/ diphenylmethyl (fluorenyl) (cyclopentadienyl) hafnium dimethyl; [(ethyl(triethylsilyl)) (perfluorooctyl) ammonium]⁺--perfluorobiphenyl--[(2,5-difluorophenyl(2,3-difluorophenyl) (perfluoropyrenyl)aluminate]⁻/ diphenylmethyl (fluorenyl) (cyclopentadienyl) zirconium dimethyl; (bis(perfluorophenyl)ammonium]⁺--perfluorobiphenyl--[(2,5-difluorophenyl(3,4-difluorophenyl) (trifluoroindenyl)aluminate]⁻/ diphenylmethyl (fluorenyl) (cyclopentadienyl) zirconium dimethyl; [(3-methylpentyl) (methyl(triethylsilyl)) phosphonium]⁺--perfluorophenyl--[(perfluorophenyl (perfluoroindenyl) (perfluorofluorenyl)borate]⁻/ diphenylmethyl (fluorenyl) (cyclopentadienyl) zirconium dimethyl; [(ethyl(triethylsilyl)) (3-methylpentyl) ammonium]⁺--perfluoroindenyl--[(trifluoroindenyl (perfluoronapthyl) (2,3-difluorophenyl)borate]⁻/ diphenylmethyl (fluorenyl) (cyclopentadienyl) zirconium dimethyl; [(isohexyl) (heptyl)ammonium]⁺--perfluoroindenyl--[bis(perfluorophenyl) (2,5-difluorophenyl)borate]⁻/diphenylmethyl (fluorenyl) (cyclopentadienyl) zirconium dimethyl; [(isohexyl) (ethyl (trimethylsilyl)) phosphonium]⁺--perfluoronapthyl--[bis (perfluorofluorenyl) (trifluoroindenyl)borate]⁻/ diphenylmethyl (fluorenyl) (cyclopentadienyl) zirconium dimethyl; [(isopentyl) (isopropyl)ammonium]⁺--perfluoroindenyl--[(perfluoronapthyl(pentafluorofluorenyl) (perfluoroindenyl)borate]⁻/diphenylmethyl (fluorenyl) (cyclopentadienyl) zirconium dimethyl; [(perfluoroisopentyl) (ethyl(trimethylsilyl))ammonium]⁺--pentafluorofluorenyl--[(2,3-difluorophenyl (perfluoroindenyl) (2,4-difluorophenyl)borate]⁻/ diphenylmethyl (fluorenyl) (cyclopentadienyl) zirconium dimethyl; [(perfluoroisopropyl) (ethyl(trimethylsilyl)) ammonium]⁺--perfluoroindenyl--[(perfluoropyrenyl (perfluorophenyl) (2,4-difluorophenyl)borate]⁻/ diphenylmethyl (fluorenyl) (cyclopentadienyl) zirconium dimethyl; [(perfluoromethyl) (ethyl)ammonium]⁺--perfluoroindenyl--[bis(perfluorobiphenyl) (2,3-difluorophenyl)borate]⁻/diphenylmethyl (fluorenyl) (cyclopentadienyl) zirconium dimethyl; [(perfluorooctyl) (3-methylpentyl)arsonium]⁺--perfluorophenyl--[(2,4-difluorophenyl(perfluorofluorenyl) (tetrafluoroindenyl) borate]⁻/diphenylmethyl (fluorenyl) (cyclopentadienyl) zirconium dimethyl; [(perfluorooctyl) (ethyl)ammonium]⁺--perfluorophenyl--[bis(perfluoroindenyl) (perfluorobiphenyl) borate]⁻/diphenylmethyl (fluorenyl) (cyclopentadienyl) zirconium dimethyl; [(phenyl) (t-butyl)ammonium]⁺--perfluorofluorenyl--[(perfluoronapthyl(2,5-difluorophenyl) (perfluoroindenyl)borate]⁻/diphenylmethyl (fluorenyl) (cyclopentadienyl) zirconium dimethyl; [(perfluoropentyl) (methyl)ammonium]⁺--perfluorofluorenyl--[(perfluoronapthyl(perfluoroindenyl) (pentafluorofluorenyl) gallinate]⁻/diphenylmethyl (fluorenyl) (cyclopentadienyl) zirconium dimethyl; [(phenyl) (heptyl)ammonium]⁺--perfluoropyrenyl--[(pentafluoronaphthyl (tetrafluoronaphthyl) (3,4-difluorophenyl)gallinate]⁻/ diphenylmethyl (fluorenyl) (cyclopentadienyl) zirconium dimethyl; [(hexyl) (ethyl(trimethylsilyl)) phosphonium]⁺--pentafluorofluorenyl--[(pentafluoronaphthyl (perfluoronapthyl) (perfluorobiphenyl)aluminate]⁻/oxotris (trimethlsilylmethyl) vanadium; [(ethyl) (perfluoromethyl) ammonium]⁺--tetrafluoroindenyl--[(2,4-difluorophenyl (perfluorofluorenyl) (perfluorobiphenyl)borate]⁻/oxotris (trimethlsilylmethyl) vanadium; [(ethyl(triethylsilyl)) (perfluorohexyl) phosphonium]⁺--perfluoronapthyl--[(perfluoroindenyl(perfluoropyrenyl) (perfluorofluorenyl) borate]⁻/oxotris(trimethlsilylmethyl) vanadium; [(ethyl (trimethylsilyl)) (methyl(triethylsilyl))ammonium]⁺--trifluoroindenyl--[bis(perfluoroindenyl) (perfluoropyrenyl) borate]⁻/oxotris(trimethlsilylmethyl) vanadium; [(ethyl (trimethylsilyl)) (2,3,4,5-tetrafluorophenyl)arsonium]⁺--2, 4-difluorophenyl--[(tetrafluoroindenyl(perfluorophenyl) (perfluorofluorenyl)borate]⁻/oxotris(trimethlsilylmethyl) vanadium; [(heptyl) (1,6-difluorohexyl)ammonium]⁺--perfluorophenyl--[bis(perfluorofluorenyl) (perfluoroindenyl)borate]⁻/oxotris(trimethlsilylmethyl) vanadium; [(heptyl) (phenyl)ammonium]⁺-2,4-difluorophenyl--[(pentafluoronaphthyl(perfluoronapthyl) (2,4-difluorophenyl)borate]⁻/oxotris(trimethlsilylmethyl) vanadium; [(perfluoroheptyl) (methyl)ammonium]⁺--tetrafluoroindenyl--[(perfluorophenyl(2,3,4-trifluorophenyl) (2,3,5-trifluorophenyl)borate]⁻/oxotris(trimethlsilylmethyl) vanadium; [(perfluorooctyl) ((methyl(triethylsilyl))) phosphonium]⁺--perfluorobiphenyl--[(pentafluoronaphthyl (perfluorobiphenyl) (2,5-difluorophenyl)borate]⁻/oxotris (trimethlsilylmethyl) vanadium; [(perfluorooctyl) (ethyl (triethylsilyl))ammonium]⁺--2,4-difluorophenyl--[(2,5-difluorophenyl(perfluorofluorenyl) (pentafluoronaphthyl) borate]⁻/oxotris(trimethlsilylmethyl) vanadium; [(perfluorophenyl) (ethyl(trimethylsilyl))ammonium]⁺--perfluoronapthyl--[(perfluoropyrenyl(2,3,4-trifluorophenyl) (perfluorofluorenyl)borate]⁻/oxotris(trimethlsilylmethyl) vanadium; [(perfluoropropyl) (ethyl(trimethylsilyl)) ammonium]⁺--tetrafluoroindenyl--[(perfluorobiphenyl (perfluoroindenyl) (perfluorophenyl)borate]⁻/oxotris (trimethlsilylmethyl) vanadium; (bis(perfluoropropyl) phosphonium]⁺--perfluorofluorenyl--[(perfluoropyrenyl (trifluoroindenyl) (3,4-difluorophenyl)borate]⁻/oxotris (trimethlsilylmethyl) vanadium; [(phenyl) (3-methylpentyl) ammonium]⁺--perfluorofluorenyl--[(pentafluorofluorenyl (perfluoropyrenyl) (pentafluoronaphthyl)borate]⁻/oxotris (trimethlsilylmethyl) vanadium; [(phenyl) (1,6-difluorohexyl)ammonium]⁺--perfluorofluorenyl--[(2,3,4-trifluorophenyl(perfluorobiphenyl) (perfluoronapthyl) borate]⁻/oxotris(trimethlsilylmethyl) vanadium; [(propyl) (pentyl) phosphonium]⁺--perfluoronapthyl--[(perfluorophenyl(perfluorofluorenyl) (perfluoroindenyl) borate]⁻/oxotris(trimethlsilylmethyl) vanadium; [(methyl (trimethylsilyl)) (butyl)ammonium]⁺--trifluoroindenyl--[(3, 4-difluorophenyl(2,3,4-trifluorophenyl) (perfluorobiphenyl) gallinate]⁻/oxotris(trimethlsilylmethyl) vanadium; [(perfluoromethyl) (isopropyl)ammonium]⁺--2,5-difluorophenyl--[tris(2,3,5-trifluorophenyl)gallinate]⁻/ oxotris(trimethlsilylmethyl) vanadium; [(methyl (triethylsilyl)) (3-methylpentyl)ammonium]⁺--2,3-difluorophenyl--[(perfluorophenyl(trifluoroindenyl) (2,3,4-trifluorophenyl)aluminate]⁻/pentamethyl cyclopentadienyl titanium isopropoxide; [(perfluorohexyl) (pentyl) phosphonium]⁺--perfluorofluorenyl--[tris(perfluorophenyl) aluminate]⁻/pentamethyl cyclopentadienyl titanium isopropoxide; [(perfluorophenyl) (t-butyl)ammonium]⁺--pentafluoronaphthyl--[(2,3,4-trifluorophenyl (pentafluoronaphthyl) (perfluorophenyl)aluminate]⁻/ pentamethyl cyclopentadienyl titanium isopropoxide; [(2,3, 5-trifluorophenyl) ((methyl(triethylsilyl))) phosphonium]⁺--2,3,4-trifluorophenyl--[bis(perfluorophenyl) (2,5-difluorophenyl)borate]⁻/pentamethyl cyclopentadienyl titanium isopropoxide; [(pentyl) (perfluoroisopentyl) ammonium]⁺--pentafluoronaphthyl--[(perfluorophenyl (pentafluoronaphthyl) (2,3-difluorophenyl)borate]⁻/ pentamethyl cyclopentadienyl titanium isopropoxide; [(phenyl) (ethyl(trimethylsilyl))ammonium]⁺--perfluorophenyl--[(perfluorobiphenyl(perfluorophenyl) (2,3, 5-trifluorophenyl)borate]⁻/pentamethyl cyclopentadienyl titanium isopropoxide; [(phenyl) (heptyl)ammonium]⁺--perfluoronapthyl--[(perfluorofluorenyl(2,3,4-trifluorophenyl) (pentafluoronaphthyl)borate]⁻/pentamethyl cyclopentadienyl titanium isopropoxide; [(pentyl) (ethyl) (trimethylsilyl))ammonium]⁺--perfluorobiphenyl--[bis(perfluoroindenyl) (perfluoronapthyl)gallinate]⁻/pentamethyl cyclopentadienyl titanium isopropoxide; [(perfluoroethyl) (perfluoromethyl) phosphonium]⁺--perfluorophenyl-[tris(perfluorobiphenyl)gallinate]⁻/pentamethyl cyclopentadienyl titanium isopropoxide; [(perfluoropropyl) (perfluoroethyl) phosphonium]⁺--perfluorobiphenyl--[(perfluoronapthyl(perfluoroindenyl) (perfluorobiphenyl)gallinate]⁻/pentamethyl cyclopentadienyl titanium isopropoxide; [(methyl(trimethylsilyl)) (ethyl) ammonium]⁺--perfluorophenyl--[(perfluorophenyl (perfluoronapthyl) (perfluorobiphenyl)aluminate]⁻/pentamethyl cyclopentadienyl tribenzyl titanium; [(perfluorooctyl) (methyl(trimethylsilyl))ammonium]⁺--2,5-difluorophenyl--[(2,3-difluorophenyl(trifluoroindenyl) (2,3,4-trifluorophenyl)aluminate]⁻/pentamethyl cyclopentadienyl tribenzyl titanium; [(perfluorophenyl) (perfluoroethyl)ammonium]⁺--perfluoronapthyl--[(perfluoronapthyl (tetrafluoroindenyl) (tetrafluoronaphthyl)aluminate]⁻/pentamethyl cyclopentadienyl tribenzyl titanium; [(perfluoro-t-butyl) (2,3,6,7-tetrafluorooctyl) phosphonium]⁺--3,4-difluorophenyl--[(perfluoroindenyl (pentafluoronaphthyl) (perfluorofluorenyl)aluminate]⁻/pentamethyl cyclopentadienyl tribenzyl titanium; [(2,3,6,7-tetrafluorooctyl) (isopropyl)ammonium]⁺--perfluorophenyl--[(3,4-difluorophenyl(perfluoroindenyl) (trifluoroindenyl)borate]⁻/pentamethyl cyclopentadienyl tribenzyl titanium; bis(3-methylpentyl)ammonium]⁺--perfluorofluorenyl--[bis(perfluorophenyl) (trifluoroindenyl) borate]⁻/pentamethyl cyclopentadienyl tribenzyl titanium; [(ethyl(trimethylsilyl)) (pentyl)ammonium]⁺--tetrafluoroindenyl--[(2,3,4-trifluorophenyl (perfluoroindenyl) (2,3-difluorophenyl)borate]⁻/pentamethyl cyclopentadienyl tribenzyl titanium; [(heptyl) (perfluoro-t-butyl)arsonium]⁺--perluorophenyl--[(2,5-difluorophenyl(perfluorobiphenyl) (perfluorofluorenyl) borate]⁻/pentamethyl cyclopentadienyl tribenzyl titanium; [(isohexyl) (methyl(triethylsilyl))ammonium]⁺--trifluoroindenyl--[(perfluorofluorenyl(tetrafluoroindenyl) (perfluoronapthyl)borate]⁻/pentamethyl cyclopentadienyl tribenzyl titanium; (bis(perfluorophenyl)ammonium]⁺--perfluorobiphenyl--[bis(perfluoroindenyl) (2,3,4-trifluorophenyl)borate]⁻/pentamethyl cyclopentadienyl tribenzyl titanium; [(t-butyl) (perfluoroethyl)ammonium]⁺--perfluoronapthyl--[bis(perfluorobiphenyl) (2,4-difluorophenyl)borate]⁻/pentamethyl cyclopentadienyl tribenzyl titanium; [(1 2-difluorohexyl) (1 6-difluorohexyl) phosphonium]⁺--2,4-difluorophenyl--[(perfluoropyrenyl (trifluoroindenyl) (pentafluorofluorenyl)aluminate]⁻/pentamethylcyclopentadienyl titanium trimethyl; [(ethyl (triethylsilyl)) (perfluorobutyl)ammonium]⁺--perfluoronapthyl--[(perfluorobiphenyl(perfluorophenyl) (pentafluorofluorenyl)aluminate]⁻/pentamethylcyclopentadienyl titanium trimethyl; [(methyl (trimethylsilyl)) (isohexyl) phosphonium]⁺--2,3-difluorophenyl--[(perfluorobiphenyl(2,3,5-trifluorophenyl) (perfluoronapthyl)aluminate]⁻/pentamethylcyclopentadienyl titanium trimethyl; [(ethyl (triethylsilyl)) (propyl)ammonium]⁺--perfluoroindenyl--[(perfluorofluorenyl(perfluoroindenyl) (perfluoronapthyl) borate]⁻/pentamethylcyclopentadienyl titanium trimethyl; (bis(ethyl(trimethylsilyl)) phosphonium]⁺--perfluorofluorenyl--[(perfluoroindenyl(perfluoronapthyl) (2,4-difluorophenyl)borate]⁻/pentamethylcyclopentadienyl titanium trimethyl; [(hexyl) (methyl)arsonium]⁺--perfluorofluorenyl--[(2,3,4-trifluorophenyl (pentafluoronaphthyl) (perfluorofluorenyl)borate]⁻/pentamethylcyclopentadienyl titanium trimethyl; [(isohexyl) (isopropyl)ammonium]⁺--perfluoroindenyl--[(perfluorobiphenyl(3,4-difluorophenyl) (tetrafluoronaphthyl)borate]⁻/pentamethylcyclopentadienyl titanium trimethyl; [(methyl(triethylsilyl)) (butyl) phosphonium]⁺--trifluoroindenyl--[tris(perfluorophenyl) borate]⁻/pentamethylcyclopentadienyl titanium trimethyl; [(methyl(triethylsilyl)) (perfluoroethyl)arsonium]⁺--perfluoroindenyl--[(perfluorofluorenyl(3,4-difluorophenyl) (perfluoronapthyl)borate]⁻/pentamethylcyclopentadienyl titanium trimethyl; [(octyl) (perfluoro-t-butyl) ammonium]⁺--pentafluorofluorenyl--[bis(2,3,5-trifluorophenyl) (perfluoroindenyl)borate]⁻/pentamethylcyclopentadienyl titanium trimethyl; [(pentyl) (1,2-difluorohexyl)ammonium]⁺--perfluoronapthyl--[(perfluoropyrenyl(trifluoroindenyl) (perfluorophenyl) borate]⁻/pentamethylcyclopentadienyl titanium trimethyl; [(perfluoroheptyl) (perfluorooctyl)ammonium]⁺--perfluoroindenyl--[bis(perfluorobiphenyl) (2,3,4-trifluorophenyl)borate]⁻/pentamethylcyclopentadienyl titanium trimethyl; [(perfluoroisopentyl) (methyl(triethylsilyl)) phosphonium]⁺--perfluoronapthyl--[bis(perfluorophenyl) (2,4-difluorophenyl)borate]⁻/pentamethylcyclopentadienyl titanium trimethyl; [(perfluoroisopentyl) (isopentyl) ammonium]⁺--perfluorofluorenyl--[(pentafluoronaphthyl (perfluorofluorenyl) (perfluoropyrenyl)borate]⁻/pentamethylcyclopentadienyl titanium trimethyl; [(perfluoropropyl) (perfluorooctyl)ammonium]⁺--2,3-difluorophenyl--[(perfluorophenyl(perfluorobiphenyl) (pentafluoronaphthyl)borate]⁻/pentamethylcyclopentadienyl titanium trimethyl; [(perfluoropropyl) (3-methylpentyl)ammonium]⁺--perfluorofluorenyl--[(perfluorofluorenyl(perfluoroindenyl) (perfluorobiphenyl)borate]⁻/pentamethylcyclopentadienyl titanium trimethyl; [(2,3,4,5-tetrafluorophenyl) (3-methylpentyl)ammonium]⁺--2,3,4-trifluorophenyl--[bis (perfluoroindenyl) (perfluorophenyl)gallinate]⁻/pentamethylcyclopentadienyl titanium trimethyl; [(isohexyl) ((methyl(triethylsilyl)))ammonium]⁺--perfluorofluorenyl--[(perfluorofluorenyl(trifluoroindenyl) (perfluorobiphenyl)gallinate]⁻/pentamethylcyclopentadienyl titanium trimethyl; [((methyl (triethylsilyl))) (isopropyl)ammonium]⁺--perfluorofluorenyl--[(perfluoronapthyl(perfluorobiphenyl) (perfluorophenyl)aluminate]⁻/silacyclobutyl (tetramethylcyclopentadienyl) (n-propylcyclopentadienyl) zirconium dimethyl; [((methyl(triethylsilyl))) (octyl) phosphonium]⁺--trifluoroindenyl--[(2,5-difluorophenyl(2,3-difluorophenyl) (perfluorophenyl)aluminate]⁻/silacyclobutyl(tetramethylcyclopentadienyl) (n-propylcyclopentadienyl) zirconium dimethyl; [(ethyl (trimethylsilyl)) (3-methylpentyl)ammonium]⁺--perfluorofluorenyl--[(2,5-difluorophenyl (perfluorofluorenyl) (perfluoronapthyl)aluminate]⁻/silacyclobutyl(tetramethylcyclopentadienyl) (n-propylcyclopentadienyl) zirconium dimethyl; [(methyl) (perfluorooctyl) phosphonium]⁺--trifluoroindenyl--[(perfluoroindenyl(3,4-difluorophenyl) (perfluoronapthyl) aluminate]⁻/silacyclobutyl(tetramethylcyclopentadienyl) (n-propylcyclopentadienyl) zirconium dimethyl; [(perfluoromethyl) (methyl(trimethylsilyl))ammonium]⁺--perfluorofluorenyl--[(tetrafluoronaphthyl(2,4- difluorophenyl) (pentafluorofluorenyl)aluminate]⁻/ silacyclobutyl(tetramethylcyclopentadienyl) (n-propylcyclopentadienyl) zirconium dimethyl; [(3-methylpentyl) (1,2-difluorohexyl) phosphonium]⁺--perfluoronapthyl--[(perfluoroindenyl(2,4-difluorophenyl) (tetrafluoroindenyl)borate]⁻/silacyclobutyl (tetramethylcyclopentadienyl) (n-propylcyclopentadienyl) zirconium dimethyl; [(ethyl) (perfluoroisopropyl) ammonium]⁺--trifluoroindenyl--[(perfluorobiphenyl(3,4-difluorophenyl) (perfluoroindenyl)borate]⁻/silacyclobutyl (tetramethylcyclopentadienyl) (n-propylcyclopentadienyl) zirconium dimethyl; [(ethyl(triethylsilyl)) (isohexyl) ammonium]⁺--perfluoronapthyl--[(tetrafluoroindenyl (perfluorobiphenyl) (perfluorophenyl)borate]⁻/ silacyclobutyl(tetramethylcyclopentadienyl) (n-propylcyclopentadienyl) zirconium dimethyl; [(ethyl (trimethylsilyl)) (isohexyl)arsonium]⁺--tetrafluoroindenyl--[(perfluoronapthyl(pentafluoronaphthyl) (3,4-difluorophenyl)borate]⁻/silacyclobutyl (tetramethylcyclopentadienyl) (n-propylcyclopentadienyl) zirconium dimethyl; [(isohexyl) (methyl)ammonium]⁺--perfluorobiphenyl--[bis(tetrafluoroindenyl) (2,5-difluorophenyl)borate]⁻/silacyclobutyl (tetramethylcyclopentadienyl) (n-propylcyclopentadienyl) zirconium dimethyl; [(perfluoroisopentyl) (isohexyl) ammonium]⁺--perfluorobiphenyl--[(perfluorobiphenyl (perfluorofluorenyl) (2,5-difluorophenyl)borate]⁻/ silacyclobutyl(tetramethylcyclopentadienyl) (n-propylcyclopentadienyl) zirconium dimethyl; [(perfluorooctyl) ((methyl(triethylsilyl))) phosphonium]⁺-- perfluoronapthyl--[(tetrafluoronaphthyl(2,3,5-trifluorophenyl) (2,3,4-trifluorophenyl)borate]⁻/ silacyclobutyl(tetramethylcyclopentadienyl) (n-propylcyclopentadienyl) zirconium dimethyl; [(perfluorophenyl) (heptyl)ammonium]⁺-- perfluorobiphenyl--[(perfluorophenyl(2,5-difluorophenyl) (perfluoronapthyl)borate]⁻/silacyclobutyl (tetramethylcyclopentadienyl) (n-propylcyclopentadienyl) zirconium dimethyl; [(methyl(trimethylsilyl)) (3-methylpentyl)ammonium]⁺--perfluorofluorenyl-- [(perfluorobiphenyl(perfluorophenyl) (2,4-difluorophenyl) gallinate]⁻/silacyclobutyl(tetramethylcyclopentadienyl) (n-propylcyclopentadienyl) zirconium dimethyl; [(1,2-difluorohexyl) (perfluorophenyl)ammonium]⁺-- pentafluorofluorenyl--[(perfluoroindenyl(perfluoronapthyl) (trifluoroindenyl)aluminate]⁻/tetra(bis (trimethylsilylmethyl)) zirconium; [(methyl(triethylsilyl)) (butyl)ammonium]⁺--perfluorofluorenyl--[(perfluorophenyl (perfluoronapthyl) (2,3,5-trifluorophenyl)aluminate]⁻/tetra (bis(trimethylsilylmethyl)) zirconium; [(t-butyl) (perfluoroisopropyl) phosphonium]⁺--perfluorofluorenyl-- [bis(perfluoronapthyl) (tetrafluoronaphthyl)aluminate]⁻/ tetra(bis(trimethylsilylmethyl)) zirconium; [(3-methylpentyl) (perfluoromethyl)ammonium]⁺-- perfluorobiphenyl--[bis(perfluoroindenyl) (perfluorobiphenyl)borate]⁻/tetra(bis(trimethylsilylmethyl)) zirconium; [(hexyl) (t-butyl)ammonium]⁺-- perfluorobiphenyl--[(perfluorophenyl(perfluoronapthyl) (perfluorobiphenyl)borate]⁻/tetra(bis(trimethylsilylmethyl)) zirconium; [(methyl(trimethylsilyl)) (pentyl)ammonium]⁺-- perfluorobiphenyl--[(perfluorophenyl(perfluoroindenyl) (2,3,4-trifluorophenyl)borate]⁻/tetra(bis (trimethylsilylmethyl)) zirconium; [(perfluorohexyl) (methyl(triethylsilyl))ammonium]⁺--trifluoroindenyl-- [(perfluoroindenyl(tetrafluoroindenyl) (perfluoroindenyl) borate]⁻/tetra(bis(trimethylsilylmethyl)) zirconium; (bis (perfluoromethyl)ammonium]⁺--tetrafluoronaphthyl--[bis (tetrafluoronaphthyl) (perfluorofluorenyl)borate]⁻/tetra(bis (trimethylsilylmethyl)) zirconium; [(perfluoro-t-butyl) (2,3, 4,5-tetrafluorophenyl)ammonium]⁺--perluoronapthyl--[bis (perfluorobiphenyl) (3,4-difluorophenyl)borate]⁻/tetra(bis (trimethylsilylmethyl)) zirconium; [(phenyl) (perfluorophenyl)ammonium]⁺--perfluorophenyl-- [(trifluoroindenyl(2,3,4-trifluorophenyl) (perfluoronapthyl) borate]⁻/tetra(bis(trimethylsilylmethyl)) zirconium; [(perfluoropentyl) (ethyl(triethylsilyl))ammonium]⁺-- perfluorophenyl--[bis(perfluorofluorenyl) (tetrafluoronaphthyl)gallinate]⁻/tetra(bis (trimethylsilylmethyl)) zirconium; [(1,2-difluorohexyl) (perfluoroisopentyl)arsonium]⁺--perfluorophenyl-- [(perfluorobiphenyl(perfluoronapthyl) (3,4-difluorophenyl) aluminate]⁻/tetrabenzyl hafnium; [(isopentyl) (2,3,4,5-tetrafluorophenyl) phosphonium]⁺--2,3,5-trifluorophenyl-- [(perfluoroindenyl(tetrafluoroindenyl) (2,3-difluorophenyl) aluminate]⁻/tetrabenzyl hafnium; [(perfluoroethyl) (ethyl (trimethylsilyl)) phosphonium]⁺--perfluoroindenyl-- [(perfluorofluorenyl(perfluorobiphenyl) (perfluorophenyl) aluminate]⁻/tetrabenzyl hafnium; [(perfluoromethyl) (isohexyl)ammonium]⁺--perfluorobiphenyl-- [(perfluorofluorenyl(perfluorobiphenyl) (perfluoroindenyl) aluminate]⁻/tetrabenzyl hafnium; [(2,3,6,7-tetrafluorooctyl) (methyl(trimethylsilyl))ammonium]⁺--perfluorofluorenyl-- [(trifluoroindenyl(perfluorobiphenyl) (perfluoroindenyl) borate]⁻/tetrabenzyl hafnium; [(3-methylpentyl) (2,3,4,5-tetrafluorophenyl)ammonium]⁺--perluoronapthyl--[(2,3-difluorophenyl(perfluorobiphenyl) (perfluorofluorenyl) borate]⁻/tetrabenzyl hafnium; [(butyl) (2,3,6,7-tetrafluorooctyl)arsonium]⁺--trifluoroindenyl--[(2,3-difluorophenyl(perfluorophenyl) (2,3,4-trifluorophenyl) borate]⁻/tetrabenzyl hafnium; [(methyl(trimethylsilyl)) (2,3, 4,5-tetrafluorophenyl)ammonium]⁺--perfluorobiphenyl-- [(perfluorophenyl(perfluoroindenyl) (perfluoronapthyl) borate]⁻/tetrabenzyl hafnium; [(perfluorobutyl) (3-methylpentyl)ammonium]⁺--perfluoropyrenyl--[(2,4-difluorophenyl(2,3-difluorophenyl) (perfluorofluorenyl) borate]⁻/tetrabenzyl hafnium; [(perfluoroethyl) (1,6-difluorohexyl) phosphonium]⁺--perfluorobiphenyl-- [(perfluoropyrenyl(2,3,5-trifluorophenyl) (perfluoroindenyl) borate]⁻/tetrabenzyl hafnium; [(perfluoroisopropyl) (perfluoroheptyl)ammonium]⁺--pentafluoronaphthyl-- [(trifluoroindenyl(pentafluoronaphthyl) (perfluoronapthyl) borate]⁻/tetrabenzyl hafnium; [(perfluoroisopropyl) (isohexyl)ammonium]⁺--perfluoroindenyl--[(2,3,5-trifluorophenyl(2,3,4-trifluorophenyl) (perfluorobiphenyl) borate]⁻/tetrabenzyl hafnium; [(octyl) (2,3,4,5-tetrafluorophenyl) phosphonium]⁺--2,3,5-trifluorophenyl-- [bis(perfluorobiphenyl) (perfluorophenyl)gallinate]⁻/ tetrabenzyl hafnium; [(pentyl) (perfluoroheptyl) ammonium]⁺--perfluorophenyl--[(peruoronapthyl (pentafluorofluorenyl) (3,4-difluorophenyl)gallinate]⁻/ tetrabenzyl hafnium; [(perfluorohexyl) (heptyl)arsonium]⁺-- perfluoropyrenyl--[(perfluoroindenyl(perfluoropyrenyl) (pentafluorofluorenyl)gallinate]⁻/tetrabenzyl hafnium;

[(ethyl(trimethylsilyl)) (heptyl)ammonium]⁺-- perfluoroindenyl--[(perfluorobiphenyl(perfluorophenyl) (pentafluoronaphthyl)aluminate]⁻/tetrabenzyl titanium; [(isopentyl) (phenyl) phosphonium]⁺-- pentafluorofluorenyl--[(perfluorobiphenyl(perfluoronapthyl) (perfluorofluorenyl)aluminate]⁻/tetrabenzyl titanium; [(hexyl) (perfluoroheptyl) phosphonium]⁺-- perfluoronapthyl--[(perfluoronapthyl(perfluorophenyl) (2,3, 5-trifluorophenyl)borate]⁻/tetrabenzyl titanium; [(isohexyl) (propyl)arsonium]⁺--2,3,4-trifluorophenyl-- [(perfluorophenyl(2,3,4-trifluorophenyl)

(pentafluorofluorenyl)borate]⁻/tetrabenzyl titanium; [(perfluoroethyl) (ethyl(triethylsilyl))ammonium]⁺--2,4-difluorophenyl--[(perfluorophenyl(3,4-difluorophenyl) (pentafluorofluorenyl)borate]⁻/tetrabenzyl titanium; [(perfluorohexyl) (perfluoropropyl)ammonium]⁺--perfluorophenyl--[(perfluoroindenyl(perfluorobiphenyl) (perfluorofluorenyl)borate]⁻/tetrabenzyl titanium; [(perfluoropropyl) (isopropyl)ammonium]⁺--perfluoronapthyl--[bis(pentafluorofluorenyl) (perfluoroindenyl)borate]⁻/tetrabenzyl titanium; [(perfluoro-t-butyl) (isohexyl)ammonium]⁺--perfluorobiphenyl--[(perfluorophenyl(perfluoroindenyl) (pentafluoronaphthyl)borate]⁻/tetrabenzyl titanium; [(perfluoro-t-butyl) (methyl)ammonium]⁺--perfluorofluorenyl--[(perfluorobiphenyl (tetrafluoronaphthyl) (perfluoronapthyl)borate]⁻/tetrabenzyl titanium; [(1,6-difluorohexyl) (2,3,4,5-tetrafluorophenyl) phosphonium]⁺--perfluorophenyl--[(pentafluorofluorenyl (perfluorofluorenyl) (3,4-difluorophenyl)aluminate]⁻/tetrabenzyl zirconium; [(heptyl) (2,3,4,5-tetrafluorophenyl) ammonium]⁺--perfluorofluorenyl--[bis(perfluorobiphenyl) (perfluoroindenyl)aluminate]⁻/tetrabenzyl zirconium; (bis(methyl)ammonium]⁺--2,3,5-trifluorophenyl--[bis(perfluoropyrenyl) (perfluorophenyl)aluminate]⁻/tetrabenzyl zirconium; [(perfluorobutyl) (propyl)ammonium]⁺--perfluorofluorenyl--[(perfluoroindenyl (tetrafluoroindenyl) (2,3,4-trifluorophenyl)aluminate]⁻/tetrabenzyl zirconium; [(perfluoromethyl) ((methyl(triethylsilyl)))ammonium]⁺--2,4-difluorophenyl--[(2,4-difluorophenyl(perfluoroindenyl) (perfluoronapthyl) aluminate]⁻/tetrabenzyl zirconium; [((methyl(triethylsilyl))) (isohexyl) phosphonium]⁺--2,3-difluorophenyl--[(perfluoronapthyl(tetrafluoroindenyl) (perfluorophenyl) borate]⁻/tetrabenzyl zirconium; [(ethyl) (perfluorohexyl) ammonium]⁺--perfluoroindenyl--[(2,5-difluorophenyl (perfluorofluorenyl) (perfluoroindenyl)borate]⁻/tetrabenzyl zirconium; [(ethyl(triethylsilyl)) ((methyl(triethylsilyl))) phosphonium]⁺--perfluorofluorenyl--[(trifluoroindenyl (pentafluoronaphthyl) (2,5-difluorophenyl)borate]⁻/tetrabenzyl zirconium; [(methyl(trimethylsilyl)) (1,6-difluorohexyl)ammonium]⁺--perfluorophenyl--[(pentafluorofluorenyl(perfluorobiphenyl) (perfluorofluorenyl)borate]⁻/tetrabenzyl zirconium; [(perfluorobutyl) (2,3,4,5-tetrafluorophenyl)ammonium]⁺--pentafluorofluorenyl--[(perfluorophenyl (tetrafluoronaphthyl) (2,3,5-trifluorophenyl)borate]⁻/tetrabenzyl zirconium; [(perfluoromethyl) (isohexyl)ammonium]⁺--pentafluorofluorenyl--[(perfluorophenyl (3r4-difluorophenyl) (perfluorobiphenyl)borate]⁻/tetrabenzyl zirconium; [(methyl(trimethylsilyl)) (t-butyl)ammonium]⁺--perfluorofluorenyl--[(3,4-difluorophenyl (perfluoropyrenyl) (perfluoroindenyl)gallinate]⁻/tetrabenzyl zirconium; [(pentyl) (methyl(triethylsilyl))ammonium]⁺--perfluorobiphenyl--[(pentafluorofluorenyl (perfluorofluorenyl) (3,4-difluorophenyl)gallinate]⁻/tetrabenzyl zirconium; [(butyl) (perfluoro-t-butyl) ammonium]⁺--perfluoronapthyl--[(2,3-difluorophenyl(2,4-difluorophenyl) (perfluorofluorenyl)aluminate]⁻tris(trimethyl silyl methyl) niobium dichloride; [(ethyl (triethylsilyl)) (3-methylpentyl)ammonium]⁺--perfluoronapthyl--[tris(perfluorobiphenyl)aluminate]⁻/tris(trimethyl silyl methyl) niobium dichloride; (bis(ethyl (triethylsilyl))ammonium]⁺--perfluorofluorenyl--[(perfluorobiphenyl(perfluorophenyl) (2,3,5-trifluorophenyl)aluminate]⁻/tris(trimethyl silyl methyl) niobium dichloride; [(3-methylpentyl) (propyl)ammonium]⁺--2,5-difluorophenyl--[(perfluoroindenyl(2,3,5-trifluorophenyl) (perfluorobiphenyl)borate]⁻/tris(trimethyl silyl methyl) niobium dichloride; [(ethyl (triethylsilyl)) (hexyl)ammonium]⁺--perfluorobiphenyl--[(perfluoronapthyl(tetrafluoroindenyl) (2,5-difluorophenyl) borate]⁻/tris(trimethyl silyl methyl) niobium dichloride; [(ethyl(triethylsilyl)) (perfluorooctyl)ammonium]⁺--perfluorophenyl--[bis(perfluoroindenyl) (perfluorofluorenyl)borate]⁻/tris(trimethyl silyl methyl) niobium dichloride; [(ethyl(triethylsilyl)) (methyl (trimethylsilyl))ammonium]⁺--perfluoronapthyl--[(perfluorofluorenyl(perfluoroindenyl) (perfluorobiphenyl) borate]⁻/tris(trimethyl silyl methyl) niobium dichloride; [(isohexyl) (perfluoroisopropyl)ammonium]⁺--perfluorobiphenyl--[(perfluoroindenyl(2,3,4-trifluorophenyl) (perfluoronapthyl)borate]⁻/tris(trimethyl silyl methyl) niobium dichloride; [(perfluorobutyl) (2,3,4,5-tetrafluorophenyl)ammonium]⁺--perfluoroindenyl--[(perfluorophenyl(2,5-difluorophenyl) (perfluorobiphenyl) borate]⁻/tris(trimethyl silyl methyl) niobium dichloride; [(perfluoroethyl) (perfluorophenyl) phosphonium]⁺--perfluoronapthyl--[bis(perfluorofluorenyl) (perfluorobiphenyl)borate]⁻/tris(trimethyl silyl methyl) niobium dichloride; [(perfluoroheptyl) (ethyl(trimethylsilyl)) arsonium]⁺--perfluoroindenyl--[bis(perfluorophenyl) (perfluoronapthyl)borate]⁻/tris(trimethyl silyl methyl) niobium dichloride; [(perfluoromethyl) (octyl)ammonium]⁺--pentafluoronaphthyl--[(perfluorophenyl (pentafluoronaphthyl) (perfluorofluorenyl)borate]⁻/tris(trimethyl silyl methyl) niobium dichloride; [(phenyl) (t-butyl)ammonium]⁺--perfluorobiphenyl--[bis(perfluorophenyl) (perfluorofluorenyl)borate]⁻/tris(trimethyl silyl methyl) niobium dichloride; [(methyl (triethylsilyl)) (isohexyl)ammonium]⁺--tetrafluoronaphthyl--[(perfluorobiphenyl (pentafluoronaphthyl) (perfluoronapthyl)gallinate]⁻/tris(trimethyl silyl methyl) niobium dichloride; [(3-methylpentyl) (perfluorohexyl)ammonium]⁺--perfluoroindenyl--[(perfluorophenyl(2,3,5-trifluorophenyl) (perfluoronapthyl)aluminate]⁻/tris(trimethylsilylmethyl) tantalum dichloride; [(perfluoroisopropyl) (perfluorooctyl) phosphonium]⁺--2,3,4-trifluorophenyl--[bis(perfluorobiphenyl) (3,4-difluorophenyl)aluminate]⁻/tris(trimethylsilylmethyl) tantalum dichloride; [(1,6-difluorohexyl) (perfluoroheptyl)ammonium]⁺--perfluorofluorenyl--[(perfluorofluorenyl(2,3,4-trifluorophenyl) (tetrafluoronaphthyl)borate]⁻/tris(trimethylsilylmethyl) tantalum dichloride; [(ethyl (triethylsilyl)) ((methyl(triethylsilyl)))ammonium]⁺--trifluoroindenyl--[(perfluorofluorenyl(2,4-difluorophenyl) (tetrafluoroindenyl)borate]⁻/tris(trimethylsilylmethyl) tantalum dichloride; [(hexyl) (methyl(trimethylsilyl)) ammonium]⁺--perfluorofluorenyl--[(pentafluoronaphthyl (perfluorobiphenyl) (3,4-difluorophenyl)borate]⁻/tris(trimethylsilylmethyl) tantalum dichloride; [(isohexyl) (ethyl(trimethylsilyl)) phosphonium]⁺--perfluoronapthyl--[bis(perfluoronapthyl) (tetrafluoronaphthyl)borate]⁻/tris(trimethylsilylmethyl) tantalum dichloride; [(isohexyl) (ethyl(trimethylsilyl))ammonium]⁺--perfluorobiphenyl--[(2,3,4-trifluorophenyl(perfluorofluorenyl) (tetrafluoroindenyl) borate]⁻/tris(trimethylsilylmethyl) tantalum dichloride; [(perfluoromethyl) (methyl(trimethylsilyl))ammonium]⁺--perfluoroindenyl--[(tetrafluoroindenyl(tetrafluoronaphthyl) (perfluorofluorenyl)borate]⁻/tris(trimethylsilylmethyl) tantalum dichloride; [(perfluoro-t-butyl) (perfluoroisopentyl) arsonium]⁺--tetrafluoronaphthyl--[(tetrafluoroindenyl(2,5-difluorophenyl) (2,3,4-trifluorophenyl)borate]⁻/tris(trimethylsilylmethyl) tantalum dichloride.

EXAMPLES

The following examples are presented to illustrate the foregoing discussion. All parts, proportions, and percentages are by weight unless otherwise indicated. Where necessary, the examples were carried out in dry, oxygen-free environments and solvents. Although the examples may be directed to certain embodiments of the present invention, they do not limit the invention in any specific respect. Certain abbreviations are used to facilitate the description. These include standard chemical abbreviations for the elements and certain commonly accepted abbreviations, such as: Me=methyl, Et=ethyl, n-Pr=normal-propyl, t-Bu=tertiary-butyl, Ph=phenyl, pfp=pentafluorophenyl, Cp=cyclopentadienyl, Ind=indenyl, Flu=fluorenyl, TMS=trimethylsilyl, TES=triethylsilyl and THF (or thf)=tetrahydrofuran.

All molecular weights are weight average molecular weight unless other-wise noted. Molecular weights (weight average molecular weight (Mw)) and number average molecular weight (Mn) were measured by Gel Permeation Chromatography (GPC) using a Waters 150 Gel Permeation Chromatograph equipped with a differential refractive index (DRI) and low angle light scattering (LS) detectors. The GPC instrument was calibrated using polystyrene standards. Samples were run in 1,2,4-trichlorobenzene (135° C.) using three Polymer Laboratories PC Gel mixed B columns in series. This general technique is discussed in "Liquid Chromatography of Polymers and Related Materials III'"J. Cazes Ed., Marcel Decker, 1981, page 207. No corrections for column spreading were employed; but data on generally accepted standards, e.g. National Institute of Standards and Technology Polyethylene 1475, demonstrated a precision with 0.2 units for Mw/Mn as calculated from elution times.

Synthesis of $BrC_6F_4$—$N(CH_2CH_2)_2$: Two grams of pyrrolidine were added to a solution of pentafluorobromobenzene (9 grams) in DMSO. The reaction mixture was stirred and warmed to 55° C. for 1 hour. The reaction vessel contents of the reaction were added to a mixture of water, ice and 5% $NaHSO_4$. Two hundred milliliters of diethyl ether were added to this mixture. The layers were separated. Then, the aqueous layer was extracted once more with 100 milliliters of diethyl ether. All organic layers were combined and dried with $MgSO_4$. $MgSO_4$ was filtered off and the solvent was removed. This procedure left a white crystalline product. Diethyl ether recrystallization gave pure product: yield= 5.25 grams, 63%. $^{19}$F NMR ($CDCl_3$, 25° C.) δ –136.9 (m, 2F), –153.6 (m, 2F). $^1$H NMR (Toluene-$d_8$, 25° C.) δ 3.12 (m, 4H), 1.33 (m, 4H).

Synthesis of $[Li(Et_2O)_2][(C_6F_5)_3BC_6F_4$—$N(CH_2CH_2)_2]$: One equivalent of BuLi (2.0 milliliters, 2M) was added to a cold (–78° C.) solution of $BrC_6F_4N(CH_2CH_2)_2$ (0.954 grams) in diethyl ether. The reaction was stirred for 30 minutes. A 50:50 toluene:diethyl ether solution of $(C_6F_5)_3B$ (1.638 grams) was added. The reaction was allowed to reach room temperature. Trituration with pentane gave an off-white solid. The $^{19}$F NMR indicated a small amount of impurity. This impurity is likely residual $(C_6F_5)_3B$. These solids were used without further purification. The impurity was removed in a latter step (see next example): yield=71%. $^1$H NMR ($CDCl_3$, 25° C.) δ 3.70 (q, 8H), 3.58 (bs, 4H), 2.03 (bs, 4H), 1.26 (t, 12H). $^{19}$F NMR ($CDCl_3$, 25° C.) δ 132.8 (m, 2F), –133.8 (m, 2F), –134.6 (m, 4F), –158.4 (m, 2F), –167.6 (t, 3F), –166.5 (m, 2F), –167.0 (m, 4F).

Synthesis of $(C_6F_5)_3BC_6F_4$—$N(CH_2CH_2)_2(H)$-Method A: Anhydrous HCl gas was added to a methylene chloride solution of $[Li(Et_2O)_2][(C_6F_5)_3BC_6F_4$—$N(CH_2CH_2)_2]$. The HCl was prepared in situ by adding concentrated sulfuric acid to sodium chloride and transferring the gas via cannula. The solution turned yellow during HCl addition. Precipitated LiCl was filtered and the solvent was removed. The product was suspended in a methylene chloride/pentane mixture, and then this suspension was filtered. The product was a white powder: yield=33%. $^{19}$F NMR ($CDCl_3$, 25° C.) δ 12.9 (m, 2F), 31 128.9 (m, 4F), –129.5 (m, 2F), –147.5 (m, 2F), –155.8 (t, 3F). –162.9 (m, 4F), –163.5 (m, 2F).

Method B: An excess of concentrated, aqueous HCl was added to an aqueous solution of $[Li(Et_2O)_2][(C_6F_5)_3BC_6F_4$—$N(CH_2CH_2)_2]$. A precipitate formed immediately. This precipitate was collected and washed thoroughly with hexanes and dried under high vacuum ($10^{-4}$ torr, 80° C., 16 hours). The product was washed with very cold methylene chloride to yield a white crystalline product: yield=46 %.

Synthesis of $LiC_6H_4$—$N(CH_3)_2$: BuLi was added to a 1:1 pentane:diethyl ether solution of 4-bromo-N,N-dimethylaniline. The reaction was stirred over night (16 hours). White precipitate formed. This precipitate was filtered and washed with cold pentane. The residual pentane was removed under vacuum. The solid was characterized by $^1$H NMR. 8.8 (d, 2H), 6.82 (d, 2H), 2.75 (s, 6H): yield=61%.

Synthesis of $[Li(Et_2O)_2][(C_6F_5)_3BC_6H_4$—$N(CH_3)_2]$: A pentane solution of $(C_6F_5)_3B$ was added to a pentane suspension of $LiC_6H_4$—$N(CH_3)_2$. The product appeared as a white precipitate. The reaction was stirred over two and one half days. The product was filtered and washed with pentane. The product was characterized by H, B, and F NMR.

Synthesis of $(C_6F_5)_3BC_6H_4$—$N(CH_3)_2(H)$: Method A (see above) was used to make this zwitterion.

Polymerization reactions: The copolymerization of ethylene and propylene were carried out in a 2-liter, continuous reactor operating at 100° C. Bis(triethylsilyl-4-phenyl-1) methylene(2,7-(di-t-butyl)fluorenyl)cyclopentadienyl) hafnium dimethyl was the catalyst. In all cases, the polymerization solvent was hexanes, while the activation solvent was toluene. Standard runs using $[B(C_6F_5)_4][C_6H_5NMe_2H]$ as the activating cocatalyst were carried out prior to each experiment to test reactor reproducibility. Standard run results are not given. For each experiment, two collections were taken. The grouping is as follows:

| EXPERIMENT | RUN (TABLE 1) | ACTIVATOR |
|---|---|---|
| 1 | 1, 2 | $(C_6F_5)_3BC_6F_4$—$N(CH_2CH_2)_2(H)$ |
| 2 | 3, 4 | $(C_6F_5)_3BC_6F_4$—$N(CH_2CH_2)_2(H)$ |
| 3 | 5, 6 | $(C_6F_5)_3BC_6H_4$—$N(CH_3)_2(H)$ |

Trioctylaluminum was used as the scavenger in all runs (25% wt). The scavenger-catalyst mole ratios for these two reactions were less than 10. The polymers were precipitated with isopropyl alcohol and dried in a vacuum oven at 75° C. The ethylene percentages in the samples were determined by FTIR (calibrated to NMR), while the molecular weights were measured by GPC.

TABLE 1

Ethylene/propylene copolymerizations

| Run | Activity (g/g) | % $C_2$ = in polymer | % $C_2$ = converted | Mn | Mw |
|---|---|---|---|---|---|
| 1 | 10667 | 77.5 | 60.6 | | |
| 2 | 7529 | 78.5 | 43.2 | 242800 | 454500 |
| 3 | 7445 | 57.5 | 45.2 | | |
| 4 | 6240 | 58.5 | 40.8 | 187207 | 333962 |

TABLE 1-continued

Ethylene/propylene copolymerizations

| Run | Activity (g/g) | % $C_2$ = in polymer | % $C_2$ = converted | Mn | Mw |
|---|---|---|---|---|---|
| 5 | 9166 | 56.1 | 37.6 | | |
| 6 | 8403 | 57.2 | 35.1 | 208446 | 399600 |

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

What is claimed is:

1. A catalyst system comprising a catalyst precursor that comprises a metal, and a cocatalyst compound that comprises:
   (a) a Group-13 anionic portion;
   (b) a cationic portion capable of activating the catalyst precursor; and
   (c) a spacing group, comprising two ends and a middle part wherein the middle part comprises a fluorinated ring moiety, connected to the Group-13 anionic portion on one end and connected to the cationic portion on the other end.

2. The catalyst system of claim 1 wherein the Group-13 anionic portion comprises a Group-13 central atom with a multiplicity of the same or different fluorinated aryl ligands.

3. The catalyst system of claim 2 wherein the Group-13 central atom is boron.

4. The catalyst system of claim 2 wherein the Group-13 central atom is aluminum.

5. The catalyst system of claim 2 wherein the aryl portion of at least one fluorinated aryl ligand is phenyl, naphthyl, biphenyl, fluorenyl, or anthracenyl.

6. The catalyst system of claim 5 wherein the aryl portion of at least one fluorinated aryl ligand is phenyl, naphthyl, or biphenyl.

7. The catalyst system of claim 2 wherein the aryl portion of at least one fluorinated aryl ligand is substantially fluorinated.

8. The catalyst system of claim 7 wherein the aryl portion of at least one fluorinated aryl ligand is perfluorinated.

9. The catalyst system of claim 1 wherein the ring moiety comprises a fluorinated homocyclic or heterocyclic aromatic, multi-, or fused-ring moiety.

10. The catalyst system of claim 9 wherein the ring moiety is fluorinated phenyl, naphthyl, or biphenyl.

11. The catalyst system of claim 9 wherein the ring moiety is perfluorinated.

12. The catalyst system of claim 1 wherein the cationic portion is —$PnR_2H^+$ wherein each R is the same or different alkyl and Pn is N, P, or As.

13. The catalyst system of claim 12 wherein Pn is N or P.

14. The catalyst system of claim 13 wherein Pn is N.

15. The catalyst system of claim 14 wherein the distal end of one R connects to the distal end of the other R to form a ring.

16. The catalyst system of claim 1 wherein the cationic portion is selected from the group consisting of silylium, trityl carbenium, Group-12 metal, anilinium, ammonium, phosphonium, and arsonium cations, and anilinium, ammonium, phosphonium, and arsonium cationic derivatives wherein the cationic derivatives contain $C_1$–$C_8$ hydrocarbyl, hydrocarbylsilyl, or hydrocarbyl-amine substituents for one or more cation hydrogen atoms.

17. The catalyst system of claim 16 wherein the cationic portion is selected from the group consisting of anilinium and ammonium cations; and anilinium and ammonium cationic derivatives containing $C_1$–$C_8$ hydrocarbyl, hydrocarbylsilyl, or hydrocarbyl-amine substituents on one or more cation hydrogen atoms.

18. The catalyst system of claim 1 wherein the catalyst precursor is a metallocene catalyst precursor, a bisamide catalyst precursor, an amine bisamide catalyst precursor, or a pyridine bisamide catalyst precursor.

19. An olefin polymerization method comprising:
   (a) providing the catalyst system of claims 1–18;
   (b) combining the catalyst precursor with the cocatalyst to form an activated catalyst and a non-coordinating anion; and
   (c) supplying polymerizable olefin to the activated catalyst.

20. A polyolefin prepared using the catalyst system of claims 1–18.

21. An article of manufacture prepared using a polyolefin prepared using the catalyst system of claims 1–18.

22. A method of preparing the cocatalyst compound of claims 1–18 comprising:
   (a) combining a secondary amine or phosphine with a fluorobromoarene;
   (b) reducing the product of step (a); followed by
   (c) adding tris(fluoroaryl)Tr (Tr=B or Al) to the reduced product; and
   (d) adding hydrogen chloride gas to the mixture.

23. The method of claim 22 wherein Tr is boron.

24. The method of claim 22 wherein the secondary amine is a heterocyclic amine.

25. The method of claim 24 wherein the heterocyclic amine is pyrrolidine.

26. The method of claim 22 wherein the fluorobromoarene is a $C_6$–$C_{12}$ aromatic compound.

27. The method of claim 22 wherein the aryl portion of the fluorobromoarene is benzene, naphthalene, or biphenyl.

28. The method of claim 27 wherein the fluorobromoarene is pentafluorobromobenzene.

29. The method of claim 22 wherein the fluorobromoarene is a perfluorinated bromoarene.

30. The method of claim 23 wherein the aryl groups of the tris(fluoroaryl)borane are independently fluorine-substituted phenyl, naphthyl, or biphenyl groups.

31. The method of claim 30 wherein the aryl groups of the tris(fluoroaryl)borane are perfluorinated.

32. The method of claim 31 wherein the tris(fluoroaryl)borane is tris(pentafluorophenyl)borane.

33. A method of prepolymerizing a catalyst system comprising:
   (a) providing the catalyst system of claims 1–18;
   (b) combining the catalyst precursor and the cocatalyst to form an activated catalyst and a non-coordinating ion;
   (c) supplying a controlled amount of olefin monomer(s) to the activated catalyst; and
   (d) collecting a prepolymerized catalyst.

* * * * *